(12) United States Patent
Robl et al.

(10) Patent No.: US 8,318,941 B2
(45) Date of Patent: Nov. 27, 2012

(54) PYRIDONE/HYDROXYPYRIDINE 11-BETA HYDROXYSTEROID DEHYDROGENASE TYPE I INHIBITORS

(75) Inventors: Jeffrey A. Robl, Newton, PA (US); Shung C. Wu, Princeton, NJ (US); David S. Yoon, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 654 days.

(21) Appl. No.: 12/307,424

(22) PCT Filed: Jul. 2, 2007

(86) PCT No.: PCT/US2007/072626
§ 371 (c)(1),
(2), (4) Date: Sep. 11, 2009

(87) PCT Pub. No.: WO2008/005910
PCT Pub. Date: Jan. 10, 2008

(65) Prior Publication Data
US 2010/0009960 A1  Jan. 14, 2010

Related U.S. Application Data

(60) Provisional application No. 60/818,913, filed on Jul. 6, 2006, provisional application No. 60/946,742, filed on Jun. 28, 2007.

(51) Int. Cl.
C07D 217/24 (2006.01)
A61K 31/4725 (2006.01)
A61K 31/472 (2006.01)

(52) U.S. Cl. ........................ 546/141; 514/309
(58) Field of Classification Search .................. 546/141; 514/309
See application file for complete search history.

(56) References Cited

U.S. PATENT DOCUMENTS

| | | | |
|---|---|---|---|
| 4,180,666 A | 12/1979 | Chorvat et al. | |
| 4,775,757 A | 10/1988 | Kanojia et al. | |
| 4,822,800 A * | 4/1989 | Falotico et al. | 514/309 |
| 5,811,432 A | 9/1998 | Marfat et al. | |
| 6,258,809 B1 | 7/2001 | Rajagopalan et al. | |
| 6,262,074 B1 | 7/2001 | Otten et al. | |
| 6,355,636 B1 | 3/2002 | Wissner et al. | |
| 6,635,633 B2 | 10/2003 | Cai et al. | |
| 6,903,118 B1 | 6/2005 | Biedermann et al. | |
| 2002/0099070 A1 | 7/2002 | Agrios | |
| 2003/0069266 A1 | 4/2003 | Wang et al. | |
| 2003/0207910 A1 | 11/2003 | Wang et al. | |
| 2004/0110785 A1 | 6/2004 | Wang et al. | |
| 2005/0054670 A1 | 3/2005 | Tegley et al. | |
| 2005/0090522 A1 | 4/2005 | Wang et al. | |
| 2005/0176754 A1 | 8/2005 | Xie et al. | |
| 2005/0215571 A1 | 9/2005 | Romano | |
| 2005/0256074 A1 | 11/2005 | Crompton | |

FOREIGN PATENT DOCUMENTS

| | | |
|---|---|---|
| CA | 2271937 | 6/1998 |
| DE | 3725357 | 3/1988 |
| DE | 3827253 | 3/1989 |
| DE | 4029466 | 3/1991 |
| GB | 1394700 | 5/1975 |
| GB | 1394701 | 5/1975 |
| GB | 1394702 | 5/1975 |
| GB | 2208862 | 4/1989 |
| WO | WO 96/03379 | 2/1996 |
| WO | WO 97/47601 | 12/1997 |
| WO | WO 98/26127 | 6/1998 |
| WO | WO 99/20298 | 4/1999 |
| WO | WO 02/076963 | 10/2002 |
| WO | WO 2004/080464 | 9/2004 |
| WO | WO 2005/097781 | 10/2005 |
| WO | WO 2006/000371 | 1/2006 |
| WO | WO 2006/024628 | 3/2006 |
| WO | WO 2006/034804 | 4/2006 |
| WO | WO 2007/017078 | 2/2007 |

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
West, Anthony R., Solid State Chemistry and its Applications, Wiley, New York, 1988, pp. 358 & 365.*
Bydal et. al. "Inhibition of type 2 17b-hydroxysteroid dehydrogenase by estradiol derivatives bearing a lactone on the D-ring: structure-activity relationships" Steroids 2004, 69, 325-342.*
Messinger, J. et. al. "New inhibitors of 17b-hydroxysteroid dehydrogenase type 1" Molecular and Cellular Endocrinology 2006, 248, 192-198.*
Webster et. al. "Discovery and biological evaluation of adamantly amide 11b-HSD1 inhibitors" Bioorganic & Medicinal Chemistry Letters 17 (2007) 2838-2843.*
Roche et. al. "Discovery and structure—activity relationships of pentanedioic acid diamides as potent inhibitors of 11b-hydroxysteroid dehydrogenase type I" Bioorganic & Medicinal Chemistry Letters 19 (2009) 2674-2678.*

(Continued)

Primary Examiner — David K O'Dell
(74) Attorney, Agent, or Firm — Terence J. Bogie

(57) ABSTRACT

Novel compounds are provided which are 11-beta-hydroxysteroid dehydrogenase type I inhibitors. 11-beta-hydroxysteroid dehydrogenase type I inhibitors are useful in treating, preventing, or slowing the progression of diseases requiring 11-beta-hydroxysteroid dehydrogenase type I inhibitor therapy. These novel compounds have the structure formula (I) enantiomers, diastereomers, solvates, salts, tautomers or prodrugs thereof wherein, A, W, X, Y and $R_1$ are defined herein.

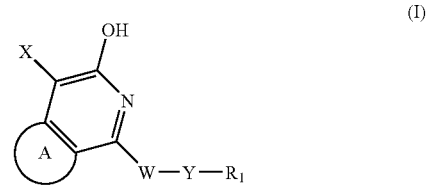

5 Claims, No Drawings

OTHER PUBLICATIONS

Xiang et. al. "Synthesis and biological evaluation of sulfonamidooxazoles and _-keto sulfones: selective inhibitors of 11_-hydroxysteroid dehydrogenase type I" Bioorganic & Medicinal Chemistry Letters 2005, 15, 2865-2869.*

Luis Castedo, Ramón J. Estévez, José M. Saá, Rafael Suau Journal of Heterocyclic Chemistry 1982 19, 6, 1469-1472.*

Shalaby "Reactivity of the Methylene Group and Cleavage of S-alkyl Groups in I-Alkylmercapto-3(4 H)-isoquinolone Derivatives" Journal für praktische Chemie 1971, 1039-1050.*

Odermatt "Diazepane—acetamide derivatives as selective 11b-hydroxysteroid dehydrogenase type 1 inhibitors" Expert Opinion on Therapeutic Patents 2009, 19(10), 1477-1484.*

Walker et. al. "11.beta.-Hydroxysteroid dehydrogenase type 1 as a novel therapeutic target in metabolic and neurodegenerative disease." Expert Opinion on Therapeutic Targets, 2003 7(6), 771-783.*

Grant R. Zimmermann "Multi-target therapeutics: when the whole is greater than the sum of the parts." Drug Discovery Today 2007, 12, 34-42.*

Borisy et. al. "Systematic discovery of multicomponent therapeutics" PNAS 2003, 100, 7977-7982.*

Sauter, F. et al., Monatshefte Fuer Chemie, Springer Verlag, Vienna, AT, vol. 126, No. 8-9, pp. 945-952 (1995).

Paronikian, Y.G. et al., Armyanskii, Khimicheskii Zhurnal/ Aikakan Himiakan Amsagir/ Armenian Chemical Journal, vol. 42, No. 8, pp. 505-509 (1989).

Kaiho, T. et al., J. Med. Chem., vol. 32, No. 2, pp. 351-357 (1989).

Ouchi, Hidekazu et al., Journal of Tohoku Pharmaceutical University, vol. 50, pp. 75-79 (2003).

Ducker, J. and Maxwell, J.G., Australian Journal of Chemistry, vol. 28, No. 3, pp. 581-590 (1975).

Kasturi and Lalitha Krishnan, T. R., Proceedings of the Indian Academy of Sciences, vol. 90, No. 4, pp. 281-290 (1981).

Kasturi T.R. et al., J. of Chemical Society, No. 1 pp. 63-68 (1982).

Abdou S. et al., Monatshefte Fur Chemie, vol. 113(8-9), pp. 985-991 (1982).

Gewald, K. et al., Journal Fuer Praktische Chemie, vol. 324, No. 6, pp. 933-941 (1982).

Victory, P. et al., J. of the Chem. Society, No. 12, pp. 2269-2272 (1989).

Van Der Baan, J. et al., J. of the Chem. Society, No. 6, pp. 326-327 (1970).

Ya Uritskaya, M. et al., Chemistry of Heterocyclic Compounds, vol. 10, pp. 1185-1187 (1973).

Row, T. N. G. et al., J. of the Chem. Society, No. 14, pp. 1597-1600 (1975).

El-Khawaga. A. M. et al., Phosphorus, Sulfur and Silicon and the related Elements, vol. 44, No. 3-4, pp. 203-207 (1989).

Paronikyan, E. G. et al., Chemistry of Heterocyclic Compounds, vol. 39, No. 3, pp. 374-378 (2003).

Paronikyan, E. G. et al., Chemistry of Heterocyclic Compounds, vol. 8, pp. 953-958 (1989).

Azimov, V.A. et al., Chemistry of Heterocyclic Compounds, vol. 2, pp. 155-159 (1981).

Kasturi, T. R. et al., Tetrahedron, vol. 29, pp. 4103-4109 (1973).

Rosowsky, A. et al., J. Med. Chem., vol. 17, No. 12, pp. 1272-1276 (1974).

Van Der Baan, J.L. et al., Tetrahedron, vol. 30, pp. 2447-2453 (1974).

Kasturi, T.R. et al., Tetrahedron, vol. 31, pp. 527-531 (1975).

Van Der Baan, J.L. et al., Tetrahedron, vol. 33, No. 10, pp. 1377-1378 (1992).

* cited by examiner

PYRIDONE/HYDROXYPYRIDINE 11-BETA HYDROXYSTEROID DEHYDROGENASE TYPE I INHIBITORS

BACKGROUND OF THE INVENTION

The steroid hormone cortisol is a key regulator of many physiological processes. However, an excess of cortisol, as occurs in Cushing's Disease, provokes severe metabolic abnormalities including: type 2 diabetes, cardiovascular disease, obesity, and osteoporosis. Many patients with these diseases, however, do not show significant increases in plasma cortisol levels. In addition to plasma cortisol, individual tissues can regulate their glucocorticoid tone via the in situ conversion of inactive cortisone to the active hormone cortisol. Indeed, the normally high plasma concentration of cortisone provides a ready supply of precursor for conversion to cortisol via the intracellular enzyme 11-beta-hydroxysteroid dehydrogenase type I (11beta-HSD1).

11beta-HSD1 is a member of the short chain dehydrogenase superfamily of enzymes. By catalyzing the conversion of cortisone to cortisol, 11beta-HSD1 controls the intracellular glucocorticoid tone according to its expression and activity levels. In this manner, 11beta-HSD1 can determine the overall metabolic status of the organ. 11beta-HSD1 is expressed at high levels in the liver and at lower levels in many metabolically active tissues including the adipose, the CNS, the pancreas, and the pituitary. Taking the example of the liver, it is predicted that high levels of 11beta-HSD1 activity will stimulate gluconeogenesis and overall glucose output. Conversely, reduction of 11beta-HSD1 activity will downregulate gluconeogenesis resulting in lower plasma glucose levels.

Various studies have been conducted that support this hypothesis. For example, transgenic mice expressing 2× the normal level of 11beta-HSD1 in only the adipose tissue show abdominal obesity, hyperglycemia, and insulin resistance. (H. Masuzaki, J. Paterson, H. Shinyama, N. M. Morton, J. J. Mullins, J. R. Seckl, J. S. Flier, "A Transgenic Model of Visceral Obesity and the Metabolic Syndrome", Science, 294:2166-2170 (2001). Conversely, when the 11beta-HSD1 gene is ablated by homologous recombination, the resulting mice are resistant to diet induced obesity and the accompanying dysregulation of glucose metabolism (N. M. Morton, J. M. Paterson, H. Masuzaki, M. C. Holmes, B. Staels, C. Fievet, B. R. Walker, J. S. Flier, J. J. Mullings, J. R. Seckl, "Novel Adipose Tissue-Mediated Resistance to Diet-induced Visceral Obesity in 11β-Hydroxysteroid Dehydrogenase Type 1-Deficient Mice", Diabetes, 53: 931-938 (2004). In addition, treatment of genetic mouse models of obesity and diabetes (ob/ob, db/db and KKAy mice) with a specific inhibitor of 11beta-HSD1 causes a decrease in glucose output from the liver and an overall increase in insulin sensitivity (P. Alberts, C. Nilsson, G. Selen, L. O. M. Engblom, N. H. M. Edling, S. Norling, G. Klingstrom, C. Larsson, M. Forsgren, M. Ashkzari, C. E. Nilsson, M. Fiedler, E. Bergqvist, B. Ohman, E. Bjorkstrand, L. B. Abrahamsen, "Selective Inhibition of 11β-Hydroxysteroid Dehydrogenase Type I Improves Hepatic Insuling Sensuitivity in Hyperglycemic Mice Strains", Endocrinology, 144:4755-4762 (2003)). Furthermore, inhibitors of 11beta-HSD1 have been shown to be effective in treating metabolic syndrome and atherosclerosis in high fat fed mice (Hermanowoki-Vosetka et al., J. Eg. Med., 202(4):517-527 (2002)). Based in part on these studies, it is believed that local control of cortisol levels is important in metabolic diseases in these model systems. In addition, the results of these studies also suggest that inhibition of 11beta-HSD1 will be a viable strategy for treating metabolic diseases such as type 2 diabetes, obesity, and the metabolic syndrome.

Lending further support to this idea are the results of a series of preliminary clinical studies. For example, several reports have shown that adipose tissue from obese individuals has elevated levels of 11beta-HSD1 activity. In addition, studies with carbenoxolone, a natural product derived from licorice that inhibits both 11beta-HSD1 and 11beta-HSD2 (converts cortisol to cortisone in kidney) have shown promising results. A seven day, double blind, placebo controlled, cross over study with carbenoxolone in mildly overweight individuals with type 2 diabetes showed that patients treated with the inhibitor, but not the placebo group, displayed a decrease in hepatic glucose production (R. C. Andrews, O. Rooyackers, B. R. Walker, J. Clin. Endocrinol. Metab., 88:285-291 (2003)). This observation is consistent with the inhibition of 11beta-HSD1 in the liver. The results of these preclinical and early clinical studies strongly support the concept that treatment with a potent and selective inhibitor of 11beta-HSD1 will be an efficacious therapy in patients afflicted with type 2 diabetes, obesity, and the metabolic syndrome.

SUMMARY OF THE INVENTION

In accordance with the present invention, aryl and heteroaryl and related compounds are provided that have the general structure of formula I:

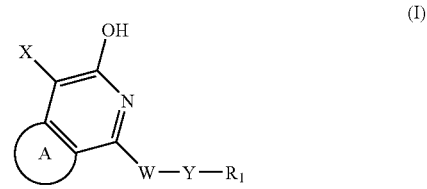

wherein A, X, W, Y and $R_1$ are defined below.

The compounds of the present invention inhibit the activity of the enzyme 11-beta-hydroxysteroid dehydrogenase type I. Consequently, the compounds of the present invention may be used in the treatment of multiple diseases or disorders associated with 11-beta-hydroxysteroid dehydrogenase type I, such as diabetes and related conditions, microvascular complications associated with diabetes, the macrovascular complications associated with diabetes, cardiovascular diseases, Metabolic Syndrome and its component conditions, inflammatory diseases and other maladies. Examples of diseases or disorders associated with the activity of the enzyme 11-beta-hydroxysteroid dehydrogenase type I that can be prevented, inhibited, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae (acute coronary syndrome, myocardial infarction, angina pectoris, peripheral vascular disease, intermitant claudication), abnormal heart function, myocardial ischemia, stroke, Metabolic Syndrome, hypertension, obesity, dislipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, glaucoma and inflammatory diseases, such as, rheumatoid arthritis, Cushing's Disease, Alzheimer's Disease and osteoarthritis.

The present invention provides for compounds of formula I, pharmaceutical compositions employing such compounds, and for methods of using such compounds. In particular, the present invention provides a pharmaceutical composition comprising a therapeutically effective amount of a compound of formula I, alone or in combination with a pharmaceutically acceptable carrier.

Further, in accordance with the present invention, a method is provided for preventing, inhibiting, or treating the progression or onset of diseases or disorders associated with the activity of the enzyme 11-beta-hydroxysteroid dehydrogenase type I, such as defined above and hereinafter, wherein a therapeutically effective amount of a compound of formula I is administered to a mammalian, i.e., human, patient in need of treatment.

The compounds of the invention can be used alone, in combination with other compounds of the present invention, or in combination with one or more other agent(s).

Further, the present invention provides a method for preventing, inhibiting, or treating the diseases as defined above and hereinafter, wherein a therapeutically effective amount of a combination of a compound of formula I and another compound of formula I and/or at least one other type of therapeutic agent, is administered to a mammalian, i.e., human, patient in need of treatment.

DESCRIPTION OF THE INVENTION

In accordance with the present invention, compounds of formula I are provided

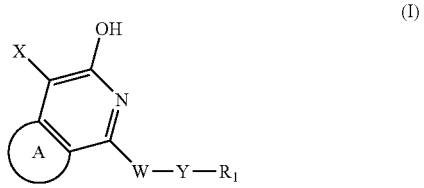

enantiomers, diastereomers, solvates, salts, tautomers or prodrugs thereof wherein:

A is a 4- to 15-membered mono-, bi- or tricyclic aliphatic or aromatic ring, wherein said ring may be optionally substituted or fused with one or more $R_4$'s; or A is a 4- to 15-membered mono-, bi- or tricyclic heterocyclyl ring wherein the heterocyclyl ring contains 1-4 heteroatoms selected from N, O, and S, and said ring may be optionally substituted or fused with one or more $R_4$'s;

X is halo, cyano, haloalkyl, —C(=O)$R_9$, —C(=O)O$R_9$, —C(=O)N$R_9R_9$, aryl or —NO$_2$;

W is a bond, alkyl, O, S, SO, N$R_9$ or SO$_2$;

Y is a bond, an alkylene or cycloalkyl, wherein the alkylene or cycloalkyl, may be optionally substituted with one or more substitutents selected from halo, haloalkyl, =O, alkyl, alkoxy, aryl, aryloxy, aryl(aryl), arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol or arylthio; provided that W and Y are not both a bond;

$R_1$ is alkyl, heteroaryl, aryl, heterocyclyl, other than heteroaryl, or cycloalkyl, all of which may be optionally substituted with one or more $R_{4a}$'s; provided that —Y—$R_1$ taken together is not methyl, ethyl, phenylcarbonylmethylenyl, 4-chlorophenylcarbonylmethylenyl or 4-bromophenylcarbonylmethylenyl;

$R_4$, at each occurrence, is independently selected from alkyl, aryl, alkenyl, alkynyl, cycloalkyl, heteroaryl, heterocyclyl, halo, =O, —NH$_2$, —CN, —NO$_2$, —C(=O)OH, —C(=O)O$R_{10}$, —O$R_{10}$, —OH, —SH, —S$R_{10}$, —S(O)$_3R_9$, —P(O)(O$R_9$)$_2$, —C(=O)N$R_9R_9$, —N$R_9R_9$, —S(O)$_2$N$R_9R_9$, —N$R_9$S(O)$_2$CF$_3$, —C(=O)N$R_9$S(O)$_2R_9$, —S(O)$_2$N$R_9$C(=O)O$R_9$, —S(O)$_2$N$R_9$C(=O)N$R_9R_9$, —C(=O)N$R_9$S(O)$_2$CF$_3$, —C(=O)$R_{10}$, —N$R_9$C(=O)H, N$R_9$C(=O)$R_{10}$, —OC(=O)$R_{10}$, —C(=N$R_{14}$)N$R_9R_9$, —NHC(=N$R_{14}$)N$R_{14}R_{14}$, —S(=O)$R_{10}$, —S(O)$_2R_{10}$, —N$R_9$C(=O)O$R_8$, —N$R_9$S(O$_2$)$R_8$, —OC(=O)N$R_9R_9$ or —N$R_9$C(=O)N$R_9R_9$, wherein the alkyl, aryl, alkenyl, alkynyl, cycloalkyl, heteroaryl or heterocyclyl may be optionally substituted with one or more $R_5$'s;

$R_{4a}$, at each occurrence, is independently selected from alkyl, aryl, alkenyl, alkynyl, cycloalkyl, heteroaryl, heterocyclyl, halo, =O, —NH$_2$, —CN, —NO$_2$, —C(=O)OH, —C(=O)O$R_{10}$, —O$R_{10}$, —OH, —SH, —S$R_{10}$, —S(O)$_3R_9$, —P(O)(O$R_9$)$_2$, —C(=O)N$R_9R_9$, —N$R_9R_9$, —S(O)$_2$N$R_9R_9$, —N$R_9$S(O)$_2$CF$_3$, —C(=O)N$R_9$S(O)$_2R_9$, —S(O)$_2$N$R_9$C(=O)O$R_9$, —S(O)$_2$N$R_9$C(=O)N$R_9R_9$, —C(=O)N$R_9$S(O)$_2$CF$_3$, —C(=O)$R_{10}$, —N$R_9$C(=O)H, —N$R_9$C(=O)$R_{10}$, —OC(=O)$R_{10}$, —C(=N$R_{14}$)N$R_9R_9$, —NHC(=N$R_{14}$)N$R_{14}R_{14}$, —S(=O)$R_{10}$, —S(O)$_2R_{10}$, —N$R_9$C(=O)O$R_8$, —N$R_9$S(O$_2$)$R_8$, —OC(=O)N$R_9R_9$ or —N$R_9$C(=O)N$R_9R_9$, wherein the alkyl, aryl, alkenyl, alkynyl, cycloalkyl, heteroaryl or heterocyclyl may be optionally substituted with one or more $R_5$'s;

$R_5$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O$R_{10}$, —OCF$_3$, —O$R_{10}$, —OH, —SH, —S$R_{10}$, —S(O)$_3R_9$, —P(O)(O$R_9$)$_2$, —C(=O)N$R_9R_9$, —N$R_9R_9$, —S(O)$_2$N$R_9R_9$, —N$R_9$S(O)$_2$CF$_3$, —C(=O)N$R_9$S(O)$_2R_9$, —S(O)$_2$N$R_9$C(=O)O$R_9$, —S(O)$_2$N$R_9$C(=O)N$R_9R_9$, —C(=O)N$R_9$S(O)$_2$CF$_3$, —C(=O)$R_{10}$, —N$R_9$C(=O)H, —N$R_9$C(=O)$R_{10}$, —OC(=O)$R_{10}$, —C(=N$R_{14}$)N$R_9R_9$, —S(=O)$R_{10}$, —S(O)$_2R_{10}$, —N$R_9$C(=O)O$R_8$ or —N$R_9$S(O$_2$)$R_8$;

$R_8$, at each occurrence, is independently alkyl, cycloalkyl or aryl;

$R_9$, at each occurrence, is independently hydrogen, alkyl, cycloalkyl, aryl, arylalkyl, heteroaryl, heteroarylalkyl, heterocyclyl or heterocyclylalkyl, wherein the cycloalkyl, aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S; or two $R_9$'s are taken together with the nitrogen to which both are attached to form a 3- to 9-membered ring, which may optionally contain 1-4 heteroatoms selected from N, O, and S and be optionally substituted with 0-5 $R_{9a}$;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O$R_{14}$, —OCF$_3$, —O$R_{14}$, —OH, —SH, —S$R_{14}$, —S(O)$_3R_9$, —P(O)(O$R_9$)$_2$, —C(=O)N$R_{14}R_{14}$, —N$R_{14}R_{14}$, —S(O)$_2$N$R_{14}R_{14}$, —N$R_{14}$S(O)$_2$CF$_3$, —C(=O)N$R_{14}$S(O)$_2R_{10}$, —S(O)$_2$N$R_{14}$C(=O)O$R_{10}$, —S(O)$_2$N$R_{14}$C(=O)N$R_{14}R_{14}$, —C(=O)N$R_{14}$S(O)$_2$CF$_3$, —C(=O)$R_{14}$, —N$R_{14}$C(=O)H, —N$R_{14}$C(=O)$R_{14}$, —OC(=O)$R_{14}$, —C(=N$R_{14}$)N$R_{14}R_{14}$, —NHC(=N$R_{14}$)N$R_{14}R_{14}$, —S(=O)$R_{14}$, —S(O)$_2R_{14}$, —N$R_{14}$C(=O)O$R_8$, —N$R_{14}$S(O$_2$)$R_8$ or arylalkyl;

$R_{10}$, at each occurrence, is independently selected from alkyl, alkenyl, alkynyl, aryl, arylalkyl, heterocyclyl or heterocyclylalkyl, wherein the alkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$R$_9$, —P(O)(OR$_9$)$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl; and $R_{14}$, at each occurrence, is independently selected from hydrogen, alkyl, cycloalkyl or aryl.

In another embodiment, compounds of formula I are those in which:

A is a 4- to 12-membered mono-, bi- or tricyclic aliphatic or aromatic ring, wherein said ring may be optionally substituted or fused with one or more $R_4$'s; or A is a 4- to 12-membered mono-, bi- or tricyclic heterocyclyl ring wherein the heterocyclyl ring contains 1-4 heteroatoms selected from N, O, and S, and said ring may be optionally substituted or fused with one or more $R_4$'s;

X is halo, cyano, haloalkyl, —C(=O)R$_9$, —C(=O)OR$_9$, —C(=O)NR$_9$R$_9$, or aryl;

W is alkyl, O, S, SO, NR$_9$ or SO$_2$;

Y is a bond, an alkylene or cycloalkyl, wherein the alkylene or cycloalkyl, may be optionally substituted with one or more substitutents selected from halo, haloalkyl, =O, alkyl, alkoxy, aryl, aryloxy, aryl(aryl), arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol or arylthio;

$R_1$ is alkyl, heteroaryl, aryl, heterocyclyl, other than heteroaryl, or cycloalkyl, all of which may be optionally substituted with one or more $R_{4a}$'s;

$R_4$, at each occurrence, is independently selected from alkyl, aryl, alkenyl, alkynyl, cycloalkyl, heteroaryl, heterocyclyl, halo, =O, —NH$_2$, —CN, —NO$_2$, —C(=O)OH, —C(=O)OR$_{10}$, —OR$_{10}$, —OH, —SH, —SR$_{10}$, —S(O)$_3$R$_9$, —P(O)(OR$_9$)$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$, —NR$_9$S(O$_2$)R$_8$, —OC(=O)NR$_9$R$_9$ or —NR$_9$C(=O)NR$_9$R$_9$, wherein the alkyl, aryl, alkenyl, alkynyl, cycloalkyl, heteroaryl or heterocyclyl may be optionally substituted with one or more $R_5$'s;

$R_{4a}$, at each occurrence, is independently selected from alkyl, aryl, alkenyl, alkynyl, cycloalkyl, heteroaryl, heterocyclyl, halo, =O, —NH$_2$, —CN, —NO$_2$, —C(=O)OH, —C(=O)OR$_{10}$, —OR$_{10}$, —OH, —SH, —SR$_{10}$, —S(O)$_3$R$_9$, —P(O)(OR$_9$)$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$, —NR$_9$S(O$_2$)R$_8$, —OC(=O)NR$_9$R$_9$ or —NR$_9$C(=O)NR$_9$R$_9$, wherein the alkyl, aryl, alkenyl, alkynyl, cycloalkyl, heteroaryl or heterocyclyl may be optionally substituted with one or more $R_5$'s;

$R_5$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$R$_9$, —P(O)(OR$_9$)$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —S(=O)R$_{10}$, —S(O)$_2$R$_{10}$, —NR$_9$C(=O)OR$_8$ or —NR$_9$S(O$_2$)R$_8$;

$R_8$, at each occurrence, is independently alkyl, cycloalkyl or aryl;

$R_9$, at each occurrence, is independently hydrogen, alkyl, cycloalkyl, aryl, arylalkyl, heteroaryl, heteroarylalkyl, heterocyclyl or heterocyclylalkyl, wherein the cycloalkyl, aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S; or two $R_9$'s are taken together with the nitrogen to which both are attached to form a 3- to 9-membered ring, which may optionally contain 1-4 heteroatoms selected from N, O, and S and be optionally substituted with 0-5 $R_{9a}$;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)OR$_4$, —OCF$_3$, —OR$_{14}$, —OH, —SH, —SR$_{14}$, —S(O)$_3$R$_9$, —P(O)(OR$_9$)$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NRK$_4$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

$R_{10}$, at each occurrence, is independently selected from alkyl, alkenyl, alkynyl, aryl, arylalkyl, heterocyclyl or heterocyclylalkyl, wherein the alkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)OR$_4$, —OCF$_3$, —OR$_{14}$, —OH, —SH, —SR$_{14}$, —S(O)$_3$R$_9$, —P(O)(OR$_9$)$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NRK$_4$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl; and $R_{14}$, at each occurrence, is independently selected from hydrogen, alkyl, cycloalkyl or aryl.

In another embodiment, compounds of formula I are those in which:

A is a 4- to 10-membered mono-, bi- or tricyclic aliphatic or aromatic ring, wherein said ring may be optionally substituted or fused with one or more $R_4$'s; or A is a 4- to 10-membered mono-, bi- or tricylic heterocyclyl ring wherein the heterocyclyl ring contains 1-4 heteroatoms selected from N, O, and S, and said ring may be optionally substituted or fused with one or more $R_4$'s;

X is halo, cyano, haloalkyl, —C(=O)$R_9$, —C(=O)O$R_9$, —C(=O)N$R_9R_9$, or aryl;

W is alkyl, O, S, N$R_9$ or $SO_2$;

Y is a bond, an alkylene or cycloalkyl, wherein the alkylene or cycloalkyl, may be optionally substituted with one or more substitutents selected from halo, haloalkyl, =O, alkyl, alkoxy, aryl, aryloxy, aryl(aryl), arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol or arylthio;

$R_1$ is alkyl, heteroaryl, aryl, heterocyclyl, other than heteroaryl, or cycloalkyl, all of which may be optionally substituted with one or more $R_{4a}$'s;

$R_4$, at each occurrence, is independently selected from alkyl, aryl, alkenyl, alkynyl, cycloalkyl, heteroaryl, heterocyclyl, halo, =O, —$NH_2$, —CN, —$NO_2$, —C(=O)OH, —C(=O)O$R_{10}$, —O$R_{10}$, —OH, —SH, —S$R_{10}$, —S(O)$_3R_9$, —P(O)(O$R_9$)$_2$, —C(=O)N$R_9R_9$, —N$R_9R_9$, —S(O)$_2$N$R_9R_9$, —N$R_9$S(O)$_2$CF$_3$, —C(=O)N$R_9$S(O)$_2R_9$, —S(O)$_2$N$R_9$C(=O)O$R_9$, —S(O)$_2$N$R_9$C(=O)N$R_9R_9$, —C(=O)N$R_9$S(O)$_2$CF$_3$, —C(=O)$R_{10}$, —N$R_9$C(=O)H, —N$R_9$C(=O)$R_{10}$, —OC(=O)$R_{10}$, —C(=N$R_{14}$)N$R_9R_9$, —NHC(=N$R_{14}$)N$R_{14}R_{14}$, —S(=O)$R_{10}$, —S(O)$_2R_{10}$, —N$R_9$C(=O)O$R_8$, —N$R_9$S(O$_2$)$R_8$, —OC(=O)N$R_9R_9$ or —N$R_9$C(=O)N$R_9R_9$, wherein the alkyl, aryl, alkenyl, alkynyl, cycloalkyl, heteroaryl or heterocyclyl may be optionally substituted with one or more $R_5$'s;

$R_{4a}$, at each occurrence, is independently selected from alkyl, aryl, alkenyl, alkynyl, cycloalkyl, heteroaryl, heterocyclyl, halo, =O, —$NH_2$, —CN, —$NO_2$, —C(=O)OH, —C(=O)O$R_{10}$, —O$R_{10}$, —OH, —SH, —S$R_{10}$, —S(O)$_3R_9$, —P(O)(O$R_9$)$_2$, —C(=O)N$R_9R_9$, N$R_9R_9$, —S(O)$_2$N$R_9R_9$, —N$R_9$S(O)$_2$CF$_3$, —C(=O)N$R_9$S(O)$_2R_9$, —S(O)$_2$N$R_9$C(=O)O$R_9$, —S(O)$_2$N$R_9$C(=O)N$R_9R_9$, —C(=O)N$R_9$S(O)$_2$CF$_3$, —C(=O)$R_{10}$, —N$R_9$C(=O)H, —N$R_9$C(=O)$R_{10}$, —OC(=O)$R_{10}$, —C(=N$R_{14}$)N$R_9R_9$, —NHC(=N$R_{14}$)N$R_{14}R_{14}$, —S(=O)$R_{10}$, —S(O)$_2R_{10}$, —N$R_9$C(=O)O$R_8$, —N$R_9$S(O$_2$)$R_8$, —OC(=O)N$R_9R_9$ or —N$R_9$C(=O)N$R_9R_9$, wherein the alkyl, aryl, alkenyl, alkynyl, cycloalkyl, heteroaryl or heterocyclyl may be optionally substituted with one or more $R_5$'s;

$R_5$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O$R_{10}$, —OCF$_3$, —O$R_{10}$, —OH, —SH, —S$R_{10}$, —S(O)$_3R_9$, —P(O)(O$R_9$)$_2$, —C(=O)N$R_9R_9$, —N$R_9R_9$, —S(O)$_2$N$R_9R_9$, —N$R_9$S(O)$_2$CF$_3$, —C(=O)N$R_9$S(O)$_2R_9$, —S(O)$_2$N$R_9$C(=O)O$R_9$, —S(O)$_2$N$R_9$C(=O)N$R_9R_9$, —C(=O)N$R_9$S(O)$_2$CF$_3$, —C(=O)$R_{10}$, —N$R_9$C(=O)H, —N$R_9$C(=O)$R_{10}$, —OC(=O)$R_{10}$, —C(=N$R_{14}$)N$R_9R_9$, —S(=O)$R_{10}$, —S(O)$_2R_{10}$, —N$R_9$C(=O)O$R_8$ or —N$R_9$S(O$_2$)$R_8$;

$R_8$, at each occurrence, is independently alkyl, cycloalkyl or aryl;

$R_9$, at each occurrence, is independently hydrogen, alkyl, cycloalkyl, aryl, arylalkyl, heteroaryl, heteroarylalkyl, heterocyclyl or heterocyclylalkyl, wherein the cylcoalkyl, aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S; or two $R_9$'s are taken together with the nitrogen to which both are attached to form a 3- to 9-membered ring, which may optionally contain 1-4 heteroatoms selected from N, O, and S and be optionally substituted with 0-5 $R_{9a}$;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O$R_{14}$, —OCF$_3$, —O$R_{14}$, —OH, —SH, —S$R_{14}$, —S(O)$_3R_9$, —P(O)(O$R_9$)$_2$, —C(=O)N$R_{14}R_{14}$, —N$R_{14}R_{14}$, —S(O)$_2$N$R_{14}R_{14}$, —N$R_{14}$S(O)$_2$CF$_3$, —C(=O)N$R_{14}$S(O)$_2R_{10}$, —S(O)$_2$N$R_{14}$C(=O)O$R_{10}$, —S(O)$_2$N$R_{14}$C(=O)N$R_{14}R_{14}$, —C(=O)N$R_{14}$S(O)$_2$CF$_3$, —C(=O)$R_{14}$, —N$R_{14}$C(=O)H, —N$R_{14}$C(=O)$R_{14}$, —OC(=O)$R_{14}$, —C(=N$R_{14}$)N$R_{14}R_{14}$, —NHC(=N$R_{14}$)N$R_{14}R_{14}$, —S(=O)$R_{14}$, —S(O)$_2R_{14}$, —N$R_{14}$C(=O)O$R_8$, —N$R_{14}$S(O$_2$)$R_8$ or arylalkyl;

$R_{10}$, at each occurrence, is independently selected from alkyl, alkenyl, alkynyl, aryl, arylalkyl, heterocyclyl or heterocyclylalkyl, wherein the alkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O$R_{14}$, —OCF$_3$, —O$R_{14}$, —OH, —SH, —S$R_{14}$, —S(O)$_3R_9$, —P(O)(O$R_9$)$_2$, —C(=O)N$R_{14}R_{14}$, —N$R_{14}R_{14}$, —S(O)$_2$N$R_{14}R_{14}$, —N$R_{14}$S(O)$_2$CF$_3$, —C(=O)N$R_{14}$S(O)$_2R_9$, —S(O)$_2$N$R_{14}$C(=O)O$R_9$, —S(O)$_2$N$R_{14}$C(=O)N$R_{14}R_{14}$, —C(=O)N$R_{14}$S(O)$_2$CF$_3$, —C(=O)$R_{14}$, —N$R_{14}$C(=O)H, —N$R_{14}$C(=O)$R_{14}$, —OC(=O)$R_{14}$, —C(=N$R_{14}$)N$R_{14}R_{14}$, —NHC(=N$R_{14}$)N$R_{14}R_{14}$, —S(=O)$R_{14}$, —S(O)$_2R_{14}$, —N$R_{14}$C(=O)O$R_8$, —N$R_{14}$S(O$_2$)$R_8$ or arylalkyl; and $R_{14}$, at each occurrence, is independently selected from hydrogen, alkyl, cycloalkyl or aryl.

In yet another embodiment, compounds of formula I are those in which:

A is a 4- to 10-membered mono-, bi- or tricylic aliphatic or aromatic ring, wherein said ring may be optionally substituted or fused with one or more $R_4$'s; or A is a 4- to 10-membered mono-, bi- or tricylic heterocyclyl ring wherein the heterocyclyl ring contains 1-4 heteroatoms selected from N, O, and S, and said ring may be optionally substituted or fused with one or more $R_4$'s;

X is halo, cyano, haloalkyl, —C(=O)$R_9$, —C(=O)O$R_9$, —C(=O)N$R_9R_9$ or aryl;

W is alkyl, O, S, N$R_9$ or $SO_2$;

Y is a bond or an alkylene, wherein the alkylene may be optionally substituted with one or more substitutents selected from halo, haloalkyl, =O, alkyl, alkoxy, aryl, aryloxy, aryl (aryl), arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol or arylthio;

$R_1$ is alkyl, heteroaryl, aryl, heterocyclyl, other than heteroaryl, or cycloalkyl, all of which may be optionally substituted with one or more $R_{4a}$'s;

$R_4$, at each occurrence, is independently selected from alkyl, aryl, alkenyl, alkynyl, cycloalkyl, heteroaryl, heterocyclyl, halo, =O, —$NH_2$, —CN, —$NO_2$, —C(=O)OH, —C(=O)O$R_{10}$, —O$R_{10}$, —OH, —SH, —S$R_{10}$, —S(O)$_3R_9$, —P(O)(O$R_9$)$_2$, —C(=O)N$R_9R_9$, —N$R_9R_9$, —S(O)$_2$N$R_9R_9$, —N$R_9$S(O)$_2$CF$_3$, —C(=O)N$R_9$S(O)$_2R_9$, —S(O)$_2$N$R_9$C(=O)O$R_9$, —S(O)$_2$N$R_9$C(=O)N$R_9R_9$, —C(=O)

$-NR_9S(O)_2CF_3$, $-C(=O)R_{10}$, $-NR_9C(=O)H$, $-NR_9C(=O)R_{10}$, $-OC(=O)R_{10}$, $-C(=NR_{14})NR_9R_9$, $-NHC(=NR_{14})NR_{14}R_{14}$, $-S(=O)R_{10}$, $-S(O)_2R_{10}$, $-NR_9C(=O)ORs$ or $-NR_9S(O_2)R_8$, wherein the alkyl, aryl, alkenyl, alkynyl, cycloalkyl, heteroaryl or heterocyclyl may be optionally substituted with one or more $R_5$'s;

$R_{4a}$, at each occurrence, is independently selected from alkyl, aryl, alkenyl, alkynyl, cycloalkyl, heteroaryl, heterocyclyl, halo, =O, $-NH_2$, $-CN$, $-NO_2$, $-C(=O)OH$, $-C(=O)OR_{10}$, $-OR_{10}$, $-OH$, $-SR_{10}$, $-S(O)_3R_9$, $-P(O)(OR_9)_2$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-C(=NR_{14})NR_9R_9$, $-NHC(=NR_{14})NR_{14}R_{14}$, $-S(=O)R_{10}$, $-S(O)_2R_{10}$, $-NR_9C(=O)OR_8$ or $-NR_9S(O_2)R_8$, wherein the alkyl, aryl, alkenyl, alkynyl, cycloalkyl, heteroaryl or heterocyclyl may be optionally substituted with one or more $R_5$'s;

$R_5$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-S(O)_3R_9$, $-P(O)(OR_9)_2$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-C(=NR_{14})NR_9R_9$, $-S(=O)R_{10}$, $-S(O)_2R_{10}$, $-NR_9C(=O)OR_8$ or $-NR_9S(O_2)R_8$;

$R_8$, at each occurrence, is independently alkyl, cycloalkyl or aryl;

$R_9$, at each occurrence, is independently hydrogen, alkyl, cycloalkyl, aryl, arylalkyl, heteroaryl, heteroarylalkyl, heterocyclyl or heterocyclylalkyl, wherein the cycloalkyl, aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

two $R_9$'s are taken together with the nitrogen to which both are attached to form a 3- to 9-membered ring, which may optionally contain 1-4 heteroatoms selected from N, O, and S and be optionally substituted with 0-5 $R_{9a}$;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3R_9$, $-P(O)(OR_9)_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_{10}$, $-S(O)_2NR_{14}C(=O)OR_{10}$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $-NR_{14}C(=O)OR_8$, $-NR_{14}S(O_2)R_8$ or arylalkyl;

$R_{10}$, at each occurrence, is independently selected from alkyl, alkenyl, alkynyl, aryl, arylalkyl, heterocyclyl or heterocyclylalkyl, wherein the alkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3R_9$, $-P(O)(OR_9)_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_9$, $-S(O)_2NR_{14}C(=O)OR_9$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $-NR_{14}C(=O)OR_8$, $-NR_{14}S(O_2)R_8$ or arylalkyl; and $R_{14}$, at each occurrence, is independently selected from hydrogen, alkyl, cycloalkyl or aryl.

In another embodiment, compounds of formula I are those in which:

A is a 4- to 10-membered mono-, bi- or tricylic aliphatic or aromatic ring, wherein said ring may be optionally substituted or fused with one or more $R_4$'s; or A is a 4- to 10-membered mono-, bi- or tricylic heterocyclyl ring wherein the heterocyclyl ring contains 1-4 heteroatoms selected from N, O, and S, and said ring may be optionally substituted or fused with one or more $R_4$'s;

X is halo, cyano, haloalkyl, $-C(=O)R_9$, $-C(=O)OR_9$ or $-C(=O)NR_9R_9$;

W is alkyl, O, S or $NR_9$;

Y is a bond or an alkylene, wherein the alkylene may be optionally substituted with one or more substitutents selected from halo, haloalkyl, =O, alkyl, alkoxy, aryl, aryloxy, aryl (aryl), arylalkyl, arylalkoxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol or arylthio;

$R_1$ is alkyl, heteroaryl, aryl, heterocyclyl, other than heteroaryl, or cycloalkyl, all of which may be optionally substituted with one or more $R_{4a}$'s;

$R_4$, at each occurrence, is independently selected from alkyl, aryl, cycloalkyl, heteroaryl, heterocyclyl, halo, =O, $-NH_2$, $-CN$, $-NO_2$, $-C(=O)OH$, $-C(=O)OR_{10}$, $-OR_{10}$, $-OH$, $-SR_{10}$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-C(=NR_{14})NR_9R_9$, $-NHC(=NR_{14})NR_{14}R_{14}$, $-S(=O)R_{10}$, $-S(O)_2R_{10}$, $-NR_9C(=O)OR_8$ or $-NR_9S(O_2)R_8$, wherein the alkyl, aryl, cycloalkyl, heteroaryl or heterocyclyl may be optionally substituted with one or more $R_5$'s;

$R_{4a}$, at each occurrence, is independently selected from alkyl, aryl, cycloalkyl, heteroaryl, heterocyclyl, halo, =O, $-NH_2$, $-CN$, $-NO_2$, $-C(=O)OH$, $-C(=O)OR_{10}$, $-OR_{10}$, $-OH$, $-SR_{10}$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-C(=NR_{14})NR_9R_9$, $-NHC(=NR_{14})NR_{14}R_{14}$, $-S(=O)R_{10}$, $-S(O)_2R_{10}$, $-NR_9C(=O)OR_8$ or $-NR_9S(O_2)R_8$, wherein the alkyl, aryl, cycloalkyl, heteroaryl or heterocyclyl may be optionally substituted with one or more $R_5$'s;

$R_5$, at each occurrence, is independently selected from alkyl, haloalkyl, aryl, cycloalkyl, cycloalkylalkyl, heteroaryl, heteroarylalkyl, heterocyclyl heterocyclylalkyl, halo, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-C(=NR_{14})NR_9R_9$, $-S(=O)R_{10}$, $-S(O)_2R_{10}$, $-NR_9C(=O)OR_8$ or $-NR_9S(O_2)R_8$;

$R_8$, at each occurrence, is independently alkyl, cycloalkyl or aryl;

$R_9$, at each occurrence, is independently hydrogen, alkyl, cycloalkyl, aryl, arylalkyl, heteroaryl, heteroarylalkyl or heterocyclyl, wherein the cycloalkyl, aryl, arylalkyl, heteroaryl, heteroarylalkyl or heterocyclyl may be optionally substituted with 0-5 $R_{9a}$, and the heteroaryl, heteroarylalkyl or heterocyclyl contain 1-4 heteroatoms selected from N, O, and S; or two $R_9$'s are taken together with the nitrogen to which both are attached to form a 3- to 9-membered ring, which may optionally contain 1-4 heteroatoms selected from N, O, and S and be optionally substituted with 0-5 $R_{9a}$;

$R_{9a}$, at each occurrence, is independently selected from alkyl, haloalkyl, aryl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

$R_{10}$, at each occurrence, is independently selected from alkyl, aryl, arylalkyl, heterocyclyl or heterocyclylalkyl, wherein the alkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl; and $R_{14}$, at each occurrence, is independently selected from hydrogen, alkyl or aryl.

In still yet another embodiment, compounds of formula I are those in which:

A is a 4- to 10-membered mono-, bi- or tricyclic aliphatic or aromatic ring, wherein said ring may be optionally substituted or fused with one or more $R_4$'s; or A is a 4- to 10-membered mono-, bi- or tricyclic heterocyclyl ring wherein the heterocyclyl ring contains 1-4 heteroatoms selected from N, O, and S, and said ring may be optionally substituted or fused with one or more $R_4$'s;

X is halo, cyano, haloalkyl, —C(=O)R$_9$, —C(=O)OR$_9$ or —C(=O)NR$_9$R$_9$;

W is alkyl, O or S;

Y is a bond or an alkylene, wherein the alkylene may be optionally substituted with one or more substitutents selected from halo, haloalkyl, =O, alkyl, alkoxy, aryl, aryloxy, aryl (aryl), arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol or arylthio;

$R_1$ is alkyl, aryl, heteroaryl or cycloalkyl, all of which may be optionally substituted with one or more $R_{4a}$'s;

$R_4$, at each occurrence, is independently selected from alkyl, aryl, cycloalkyl, heteroaryl, heterocyclyl, halo, =O, —NH$_2$, —CN, —NO$_2$, —C(=O)OH, —C(=O)OR$_{10}$, —OR$_{10}$, —OH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, —NR$_9$C(=O)OR$_8$ or —NR$_9$S(O$_2$)R$_8$, wherein the alkyl, aryl, cycloalkyl, heteroaryl or heterocyclyl may be optionally substituted with one or more $R_5$'s;

$R_{4a}$, at each occurrence, is independently selected from alkyl, aryl, cycloalkyl, heteroaryl, heterocyclyl, halo, =O, —NH$_2$, —CN, —NO$_2$, —C(=O)OH, —C(=O)OR$_{10}$, —OR$_{10}$, —OH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, —NR$_9$C(=O)OR$_8$ or —NR$_9$S(O$_2$)R$_8$, wherein the alkyl, aryl, cycloalkyl, heteroaryl or heterocyclyl may be optionally substituted with one or more $R_5$'s;

$R_5$, at each occurrence, is independently selected from alkyl, haloalkyl, aryl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, —NR$_9$C(=O)OR$_8$ or —NR$_9$S(O$_2$)R$_8$;

$R_8$, at each occurrence, is independently alkyl, cycloalkyl or aryl;

$R_9$, at each occurrence, is independently hydrogen, alkyl, cycloalkyl, aryl, arylalkyl, heteroaryl or heterocyclyl, wherein the cycloalkyl, aryl, arylalkyl, heteroaryl or heterocyclyl may be optionally substituted with 0-5 $R_{9a}$, and the heteroaryl or heterocyclyl contain 1-4 heteroatoms selected from N, O, and S; or two $R_9$'s are taken together with the nitrogen to which both are attached to form a 3- to 9-membered ring, which may optionally contain 1-4 heteroatoms selected from N, O, and S and be optionally substituted with 0-5 $R_{9a}$;

$R_{9a}$, at each occurrence, is independently selected from alkyl, haloalkyl, aryl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

$R_{10}$, at each occurrence, is independently selected from alkyl, aryl, arylalkyl, heterocyclyl, wherein the alkyl, aryl, arylalkyl or heterocyclyl may be optionally substituted with 0-3 $R_{10a}$, and the heterocyclyl contains 1-4 heteroatoms selected from N, O, and S;

$R_{10a}$, at each occurrence, is independently selected from alkyl, haloalkyl, aryl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)OR$_4$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl; and R$_{14}$, at each occurrence, is independently selected from hydrogen, alkyl or aryl.

In one embodiment, compounds of formula I are those in which:

A is a 4- to 10-membered mono- or bicyclic aliphatic or aromatic ring, wherein said ring may be optionally substituted or fused with one or more R$_4$'s; or A is a 4- to 10-membered mono- or bicyclic heterocyclyl ring wherein the heterocyclyl ring contains 1-4 heteroatoms selected from N, O, and S, and said ring may be optionally substituted or fused with one or more R$_4$'s;

X is halo, cyano, haloalkyl, —C(=O)R$_9$, —C(=O)OR$_9$ or —C(=O)NR$_9$R$_9$;

W is alkyl, O or S;

Y is a bond or an alkylene, wherein the alkylene may be optionally substituted with one or more substituents selected from halo, haloalkyl, =O, alkyl, alkoxy, aryl, aryloxy, aryl(aryl), arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol or arylthio;

R$_1$ is alkyl, aryl, heteroaryl or cycloalkyl, all of which may be optionally substituted with one or more R$_{4a}$'s;

R$_4$, at each occurrence, is independently selected from alkyl, aryl, cycloalkyl, heteroaryl, heterocyclyl, halo, =O, —NH$_2$, —CN, —NO$_2$, —C(=O)OH, —C(=O)OR$_{10}$, —OR$_{10}$, —OH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$ or —S(O)$_2$R$_{10}$, wherein the alkyl, aryl, cycloalkyl, heteroaryl or heterocyclyl may be optionally substituted with one or more R$_5$'s;

R$_{4a}$, at each occurrence, is independently selected from alkyl, aryl, cycloalkyl, heteroaryl, heterocyclyl, halo, =O, —NH$_2$, —CN, —NO$_2$, —C(=O)OH, —C(=O)OR$_{10}$, —OR$_{10}$, —OH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$ or —S(O)$_2$R$_{10}$, wherein the alkyl, aryl, cycloalkyl, heteroaryl or heterocyclyl may be optionally substituted with one or more R$_5$'s;

R$_5$, at each occurrence, is independently selected from alkyl, haloalkyl, aryl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$ or —S(O)$_2$R$_{10}$;

R$_9$, at each occurrence, is independently hydrogen, alkyl, cycloalkyl, aryl, heteroaryl or heterocyclyl, wherein the cycloalkyl, aryl, heteroaryl or heterocyclyl may be optionally substituted with 0-5 R$_{9a}$, and the heteroaryl or heterocyclyl contain 1-4 heteroatoms selected from N, O, and S; or two R$_9$'s are taken together with the nitrogen to which both are attached to form a 3- to 9-membered ring, which may optionally contain 1-4 heteroatoms selected from N, O, and S and be optionally substituted with 0-5 R$_{9a}$;

R$_{9a}$, at each occurrence, is independently selected from alkyl, haloalkyl, aryl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$ or arylalkyl;

R$_{10}$, at each occurrence, is independently selected from alkyl, aryl or heterocyclyl, wherein the alkyl, aryl or heterocyclyl may be optionally substituted with 0-3 R$_{10a}$, and the heterocyclyl contains 1-4 heteroatoms selected from N, O, and S;

R$_{10a}$, at each occurrence, is independently selected from alkyl, haloalkyl, aryl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)OR$_4$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$ or arylalkyl; and R$_{14}$, at each occurrence, is independently selected from hydrogen, alkyl or aryl.

In still yet another embodiment, compounds of formula I are those in which:

A is a 4- to 10-membered mono- or bicyclic aliphatic or aromatic ring, wherein said ring may be optionally substituted or fused with one or more R$_4$'s; or A is a 4- to 10-membered mono- or bicyclic heterocyclyl ring wherein the heterocyclyl ring contains 1-4 heteroatoms selected from N, O, and S, and said ring may be optionally substituted or fused with one or more R$_4$'s;

X is halo, cyano, haloalkyl, —C(=O)OR$_9$ or —C(=O)NR$_9$R$_9$;

W is alkyl, O or S;

Y is a bond or an alkylene;

R$_1$ is alkyl, aryl, heteroaryl or cycloalkyl, all of which may be optionally substituted with one or more R$_{4a}$'s;

R$_4$, at each occurrence, is independently selected from alkyl, aryl, heteroaryl, heterocyclyl, halo, =O, —CN, —NO$_2$, —C(=O)OH, —C(=O)OR$_{10}$, —OR$_{10}$, —OH, —SR$_{10}$, C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$ or —S(O)$_2$R$_{10}$, wherein the alkyl, aryl, heteroaryl or heterocyclyl may be optionally substituted with one or more R$_5$'s;

R$_{4a}$, at each occurrence, is independently selected from alkyl, aryl, heteroaryl, heterocyclyl, halo, =O, —CN, —NO$_2$, —C(=O)OH, —C(=O)OR$_{10}$, —OR$_{10}$, —OH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$ or —S(O)$_2$R$_{10}$, wherein the alkyl, aryl, heteroaryl or heterocyclyl may be optionally substituted with one or more R$_5$'s;

R$_5$, at each occurrence, is independently selected from alkyl, haloalkyl, aryl, cycloalkyl, heteroaryl, heterocyclyl, halo, —CN, —NO$_2$, —C(=O)OH, —C(=O)OR$_{10}$, —OR$_{10}$, —OH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$ or —S(O)$_2$R$_{10}$;

R$_9$, at each occurrence, is independently hydrogen, alkyl, cycloalkyl, aryl, heteroaryl or heterocyclyl, wherein the cycloalkyl, aryl, heteroaryl or heterocyclyl may be optionally substituted with 0-5 R$_{9a}$, and the heteroaryl or heterocyclyl contain 1-4 heteroatoms selected from N, O, and S; or two R$_9$'s are taken together with the nitrogen to which both are attached to form a 3- to 9-membered ring, which may optionally contain 1-4 heteroatoms selected from N, O, and S and be optionally substituted with 0-5 R$_{9a}$;

R$_{9a}$, at each occurrence, is independently selected from alkyl, haloalkyl, aryl, cycloalkyl, heteroaryl, heterocyclyl, halo, —CN, —NO$_2$, —C(=O)OH, —C(=O)OR$_{14}$, —OR$_{14}$, —OH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, or —S(O)$_2$R$_{14}$;

R$_{10}$, at each occurrence, is independently selected from alkyl, aryl or heterocyclyl, wherein the alkyl, aryl or heterocyclyl may be optionally substituted with 0-3 R$_{10a}$, and the heterocyclyl contains 1-4 heteroatoms selected from N, O, and S;

R$_{10a}$, at each occurrence, is independently selected from alkyl, haloalkyl, aryl, cycloalkyl, heteroaryl, heterocyclyl, halo, —CN, —NO$_2$, —C(=O)OH, —C(=O)OR$_{14}$, —OR$_{14}$, —OH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$ or —S(O)$_2$R$_{14}$; and R$_{14}$, at each occurrence, is independently selected from hydrogen, alkyl or aryl.

In another embodiment, compounds of formula I are those compounds in which:

A is a 4- to 10-membered mono- or bicyclic aliphatic or aromatic ring, wherein said ring may be optionally substituted or fused with one or more R$_4$'s; or A is a 4- to 10-membered mono- or bicyclic heterocyclyl ring wherein the heterocyclyl ring contains 1-4 heteroatoms selected from N, O, and S, and said ring may be optionally substituted or fused with one or more R$_4$'s;

X is halo, cyano, haloalkyl or —C(=O)OR$_9$;

W is alkyl, O or S;

Y is a bond or an alkylene;

R$_1$ is alkyl, aryl, heteroaryl or cycloalkyl, all of which may be optionally substituted with one or more R$_4$'s;

R$_4$, at each occurrence, is independently selected from alkyl, aryl, heteroaryl, halo, =O, —CN, —NO$_2$, —C(=O)OH, —C(=O)OR$_{10}$, —OR$_{10}$, —OH, —SR$_{10}$, —C(=O)NR$_9$R$_9$, —NR$_9$R$_9$, —S(O)$_2$NR$_9$R$_9$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)R$_{10}$, —NR$_9$C(=O)R$_{10}$, —OC(=O)R$_{10}$, —S(=O)R$_{10}$ or —S(O)$_2$R$_{10}$, wherein the alkyl, aryl or heteroaryl may be optionally substituted with one or more R$_5$'s;

R$_{4a}$, at each occurrence, is independently selected from alkyl, aryl, heteroaryl, halo, =O, —CN, —NO$_2$, —C(=O)OH, —C(=O)OR$_{10}$, —OR$_{10}$, —OH, —SR$_{10}$, —C(=O)NR$_9$R$_9$, —NR$_9$R$_9$, —S(O)$_2$NR$_9$R$_9$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)R$_{10}$, —NR$_9$C(=O)R$_{10}$, —OC(=O)R$_{10}$, —S(=O)R$_{10}$ or —S(O)$_2$R$_{10}$, wherein the alkyl, aryl or heteroaryl may be optionally substituted with one or more R$_5$'s;

R$_5$, at each occurrence, is independently selected from alkyl, haloalkyl, aryl, heteroaryl, heterocyclyl, halo, —CN, —C(=O)OH, —C(=O)OR$_{10}$, —OR$_{10}$, —OH, —SR$_{10}$, —C(=O)NR$_9$R$_9$, —NR$_9$R$_9$, —S(O)$_2$NR$_9$R$_9$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)R$_{10}$, —NR$_9$C(=O)R$_{10}$, —OC(=O)R$_{10}$, —S(=O)R$_{10}$ or —S(O)$_2$R$_{10}$;

R$_9$, at each occurrence, is independently hydrogen, alkyl, aryl, heteroaryl or heterocyclyl, wherein the aryl, heteroaryl or heterocyclyl may be optionally substituted with 0-5 R$_{9a}$, and the heteroaryl or heterocyclyl contain 1-4 heteroatoms selected from N, O, and S; or two R$_9$'s are taken together with the nitrogen to which both are attached to form a 3- to 9-membered ring, which may optionally contain 1-4 heteroatoms selected from N, O, and S and be optionally substituted with 0-5 R$_{9a}$;

R$_{9a}$, at each occurrence, is independently selected from alkyl, haloalkyl, aryl, cycloalkyl, heteroaryl, heterocyclyl, halo, —CN, —NO$_2$, —C(=O)OH, —C(=O)OR$_{14}$, —OR$_{14}$, —OH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, or —S(O)$_2$R$_{14}$;

R$_{10}$, at each occurrence, is independently selected from alkyl or aryl, wherein the alkyl or aryl may be optionally substituted with 0-3 R$_{10a}$;

R$_{10a}$, at each occurrence, is independently selected from alkyl, haloalkyl, aryl, cycloalkyl, heteroaryl, heterocyclyl, halo, —CN, —NO$_2$, —C(=O)OH, —C(=O)OR$_{14}$, —OR$_{14}$, —OH, —SR$_{14}$, —C(=O)NR$_{14}$R$_{14}$, —NR$_{14}$R$_{14}$, —S(O)$_2$NR$_{14}$R$_{14}$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —NR$_{14}$C(=O)R$_{14}$, —OC(=O)R$_{14}$, —S(=O)R$_{14}$ or —S(O)$_2$R$_{14}$; and R$_{14}$, at each occurrence, is independently selected from hydrogen, alkyl or aryl.

In another embodiment, compounds of formula I are those compounds in which:

A is a 4- to 10-membered mono- or bicyclic aliphatic or aromatic ring, wherein said ring may be optionally substituted or fused with one or more R$_4$'s; or A is a 4- to 10-membered mono- or bicyclic heterocyclyl ring wherein the heterocyclyl ring contains 1-4 heteroatoms selected from N, O, and S, and said ring may be optionally substituted or fused with one or more R$_4$'s;

X is halo, cyano or haloalkyl;

W is alkyl, O or S;

Y is a bond or an alkylene;

R$_1$ is alkyl, aryl, heteroaryl or cycloalkyl, all of which may be optionally substituted with one or more R$_{4a}$'s;

R$_4$, at each occurrence, is independently selected from alkyl, aryl, heteroaryl, halo, =O, —CN, —NO$_2$, —C(=O)OH, —C(=O)OR$_{10}$, —OR$_{10}$, —OH, —SR$_{10}$, —C(=O)NR$_9$R$_9$, —NR$_9$R$_9$, —S(O)$_2$NR$_9$R$_9$, —C(=O)R$_{10}$, —NR$_9$C(=O)R$_{10}$, —OC(=O)R$_{10}$, —S(=O)R$_{10}$ or —S(O)$_2$R$_{10}$, wherein the alkyl, aryl or heteroaryl may be optionally substituted with one or more R$_5$'s;

R$_{4a}$, at each occurrence, is independently selected from alkyl, aryl, heteroaryl, halo, =O, —CN, —NO$_2$, —C(=O)OH, —C(=O)OR$_{10}$, —OR$_{10}$, —OH, —SR$_{10}$, —C(=O)

NR$_9$R$_9$, —NR$_9$R$_9$, —S(O)$_2$NR$_9$R$_9$, —C(=O)R$_{10}$, —NR$_9$C(=O)R$_{10}$, —OC(=O)R$_{10}$, —S(=O)R$_{10}$ or —S(O)$_2$R$_{10}$, wherein the alkyl, aryl or heteroaryl may be optionally substituted with one or more R$_5$'s;

R$_5$, at each occurrence, is independently selected from alkyl, aryl, heteroaryl, heterocyclyl, halo, —CN, —C(=O)OH, —C(=O)OR$_{10}$, —OR$_{10}$, —OH, —SR$_{10}$, —C(=O)NR$_9$R$_9$, —NR$_9$R$_9$, —S(O)$_2$NR$_9$R$_9$, —C(=O)R$_{10}$, —NR$_9$C(=O)R$_{10}$, —OC(=O)R$_{10}$, —S(=O)R$_{10}$ or —S(O)$_2$R$_{10}$;

R$_9$, at each occurrence, is independently hydrogen, alkyl, aryl, heteroaryl or heterocyclyl, wherein the heteroaryl or heterocyclyl contain 1-4 heteroatoms selected from N, O, and S;

R$_{10}$, at each occurrence, is independently selected from alkyl or aryl, wherein the alkyl or aryl may be optionally substituted with 0-3 R$_{10a}$;

R$_{10a}$, at each occurrence, is independently selected from alkyl, aryl, heteroaryl, heterocyclyl, halo, —C(=O)OH, —C(=O)OR$_{14}$, —OR$_{14}$, —SR$_{14}$, —C(=O)NR$_{14}$R$_{14}$, —NR$_{14}$R$_{14}$, —S(O)$_2$NR$_{14}$R$_{14}$, —NR$_{14}$C(=O)R$_{14}$, —OC(=O)R$_{14}$, —S(=O)R$_{14}$ or —S(O)$_2$R$_{14}$; and R$_{14}$, at each occurrence, is independently selected from hydrogen, alkyl or aryl.

In another embodiment, compounds of formula I are those compounds in which:

A is a 4- to 10-membered mono- or bicyclic aliphatic or aromatic ring, wherein said ring may be optionally substituted with one or more R$_4$'s; or A is a 4- to 10-membered mono- or bicyclic heterocyclyl ring wherein the heterocyclyl ring contains 1-4 heteroatoms selected from N, O, and S, and said ring may be optionally substituted with one or more R$_4$'s;

X is halo, cyano or haloalkyl;

W is O or S;

Y is a bond or an alkylene;

R$_1$ is aryl, heteroaryl or cycloalkyl, all of which may be optionally substituted with one or more R$_{4a}$'s;

R$_4$, at each occurrence, is independently selected from alkyl, aryl, halo, =O, —CN, —NO$_2$, —C(=O)OH, —C(=O)OR$_{10}$, —OR$_{10}$, —OH, —SR$_{10}$, —C(=O)NR$_9$R$_9$, —NR$_9$R$_9$, —S(O)$_2$NR$_9$R$_9$, —C(=O)R$_{10}$, —OC(=O)R$_{10}$, —S(=O)R$_{10}$ or —S(O)$_2$R$_{10}$, wherein the alkyl or aryl may be optionally substituted with one or more R$_5$'s;

R$_{4a}$, at each occurrence, is independently selected from alkyl, aryl, halo, =O, —CN, —NO$_2$, —C(=O)OH, —C(=O)OR$_{10}$, —OR$_{10}$, —OH, —SR$_{10}$, —C(=O)NR$_9$R$_9$, —NR$_9$R$_9$, —S(O)$_2$NR$_9$R$_9$, —C(=O)R$_{10}$, —OC(=O)R$_{10}$, —S(=O)R$_{10}$ or —S(O)$_2$R$_{10}$, wherein the alkyl or aryl may be optionally substituted with one or more R$_5$'s;

R$_5$, at each occurrence, is independently selected from alkyl, aryl, heteroaryl, halo, —CN, —C(=O)OH, —C(=O)OR$_{10}$, —OR$_{10}$, —SR$_{10}$, —C(=O)NR$_9$R$_9$, —NR$_9$R$_9$, —S(O)$_2$NR$_9$R$_9$, —C(=O)R$_{10}$, —OC(=O)R$_{10}$, —S(=O)R$_{10}$ or —S(O)$_2$R$_{10}$;

R$_9$, at each occurrence, is independently hydrogen, alkyl, aryl or heteroaryl, wherein the heteroaryl contains 1-4 heteroatoms selected from N, O, and S;

R$_{10}$, at each occurrence, is independently selected from alkyl or aryl, wherein the alkyl or aryl may be optionally substituted with 0-3 R$_{10a}$;

R$_{10a}$, at each occurrence, is independently selected from alkyl, aryl, heteroaryl, halo, —C(=O)OH, —C(=O)OR$_{14}$, —OR$_{14}$, —SR$_{14}$, —C(=O)NR$_{14}$R$_{14}$, —NR$_{14}$R$_{14}$, —S(O)$_2$NR$_{14}$R$_{14}$, —OC(=O)R$_{14}$ or —S(O)$_2$R$_{14}$; and R$_{14}$, at each occurrence, is independently selected from hydrogen, alkyl or aryl.

In another embodiment, compounds of formula I are those compounds in which:

A is a 4- to 9-membered mono- or bicyclic aliphatic or aromatic ring, wherein said ring may be optionally substituted with one or more R$_4$'s; or A is a 4- to 9-membered mono- or bicyclic heterocyclyl ring wherein the heterocyclyl ring contains 1-4 heteroatoms selected from N, O, and S, and said ring may be optionally substituted with one or more R$_4$'s;

X is halo or cyano;

W is O or S;

Y is a bond or an alkylene;

R$_1$ is aryl, heteroaryl or cycloalkyl, all of which may be optionally substituted with one or more R$_{4a}$'s;

R$_4$, at each occurrence, is independently selected from alkyl, aryl, halo, =O, —CN, —NO$_2$, —C(=O)OH, —C(=O)OR$_{10}$, —OR$_{10}$, —OH, —SR$_{10}$, —C(=O)R$_{10}$ or —S(O)$_2$R$_{10}$, wherein the alkyl or aryl may be optionally substituted with one or more R$_5$'s;

R$_{4a}$, at each occurrence, is independently selected from alkyl, aryl, halo, =O, —CN, —NO$_2$, —C(=O)OH, —C(=O)OR$_{10}$, —OR$_{10}$, —OH, —SR$_{10}$, —C(=O)R$_{10}$ or —S(O)$_2$R$_{10}$, wherein the alkyl or aryl may be optionally substituted with one or more R$_5$'s;

R$_5$, at each occurrence, is independently selected from alkyl, aryl, halo, —CN, —C(=O)OH, —C(=O)OR$_{10}$, —OR$_{10}$, —SR$_{10}$, —C(=O)R$_{10}$ or —S(O)$_2$R$_{10}$;

R$_{10}$, at each occurrence, is independently selected from alkyl or aryl, wherein the alkyl or aryl may be optionally substituted with 0-3 R$_{10a}$;

R$_{10a}$, at each occurrence, is independently selected from alkyl, aryl, halo, —C(=O)OH, —C(=O)OR$_{14}$, —OR$_{14}$, —SR$_{14}$ or —S(O)$_2$R$_{14}$; and R$_{14}$, at each occurrence, is independently selected from hydrogen or alkyl.

In another embodiment, compounds of formula I are provided wherein the compound may be optionally substituted with one or more R$_4$'s and said compound is a compound of formula Ia, Ib, Ic, Id, Ie, If, Ig, Ih, Ii, Ij or Ik:

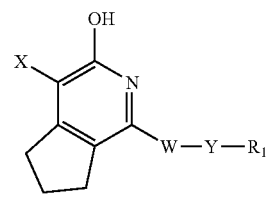

Ia

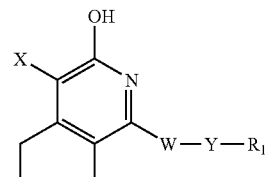

Ib

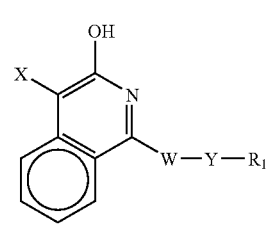

Ic

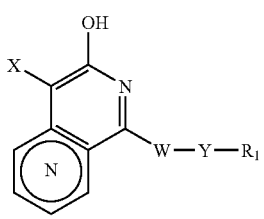

Id

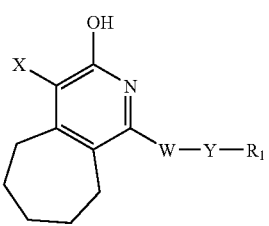

Ie

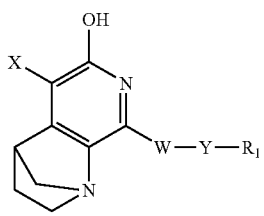

If

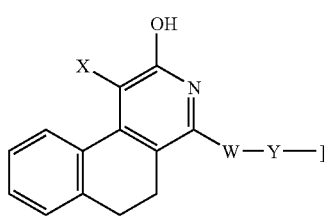

Ig

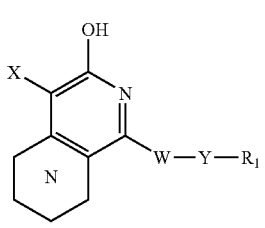

Ih

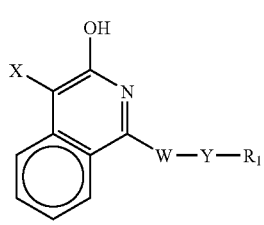

Ii

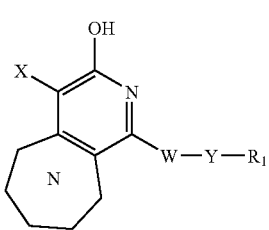

Ij

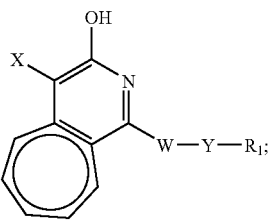

Ik wherein, the N or O inside the A ring indicates that a nitrogen or oxygen atom replaces at least one of the carbon atoms on said A ring.

In one embodiment, compounds of formula I are provided wherein said compound may be optionally substituted with one or more $R_4$'s and the compound is a compound of formula Ia, Ib, Ic or Id as set forth above.

In another embodiment, compounds of formula I are provided wherein said compound may be optionally substituted with one or more $R_4$'s and the compound is a compound of formula Ia, Ib or Ic as set forth above.

In another embodiment, compounds of the present invention are selected from the compounds exemplified in the examples.

In another embodiment, the present invention relates to pharmaceutical compositions comprised of a therapeutically effective amount of a compound of the present invention, alone or, optionally, in combination with a pharmaceutically acceptable carrier and/or one or more other agent(s).

In another embodiment, the present invention relates to methods of inhibiting the activity of the enzyme 11-beta-hydroxysteroid dehydrogenase type I comprising administering to a mammalian patient, for example, a human patient, in need thereof a therapeutically effective amount of a compound of the present invention, alone, or optionally, in combination with another compound of the present invention and/or at least one other type of therapeutic agent.

In another embodiment, the present invention relates to a method for preventing, inhibiting, or treating the progression or onset of diseases or disorders associated with the activity of the enzyme 11-beta-hydroxysteroid dehydrogenase type I comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

Examples of diseases or disorders associated with the activity of the enzyme 11-beta-hydroxysteroid dehydrogenase type I that can be prevented, inhibited, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis, acute coronary syndrome, myocardial infarction, angina pectoris, peripheral vascular disease, intermitant claudication, abnormal heart function, myocardial ischemia, stroke, Metabolic Syndrome, hypertension, obesity, dislipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, glaucoma, rheumatoid arthritis, Cushing's Disease, Alzheimer's Disease and osteoarthritis.

In another embodiment, the present invention relates to a method for preventing, inhibiting, or treating the progression or onset of diabetes, hyperglycemia, obesity, dislipidemia, hypertension, cognitive impairment, rheumatoid arthritis, osteoarthritis, glaucoma, Cushing's Disease and Metabolic Syndrome comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In still another embodiment, the present invention relates to a method for preventing, inhibiting, or treating the progression or onset of diabetes, comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In yet still another embodiment, the present invention relates to a method for preventing, inhibiting, or treating the progression or onset of hyperglycemia comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of obesity comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In one embodiment, the present invention relates to a method for preventing, inhibiting, or treating the progression or onset of dislipidemia comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of hypertension comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of cognitive impairment comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of rheumatoid arthritis comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of osteoarthritis comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of Metabolic Syndrome comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of glaucoma comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of Cushing's Disease comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, $C=N$ double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I may display superior activity compared with the other. Thus, all of the stereochemistries are considered to be a part of the present invention. When required, separation of the racemic material can be achieved by HPLC using a chiral column or by a resolution using a resolving agent such as camphonic chloride as in Steven D. Young et al., *Antimicrobial Agents and Chemotheraphy,* 2602-2605 (1995).

To the extent that compounds of the formula I, and salts thereof, may exist in their tautomeric form, all such tautomeric forms are contemplated herein as part of the present invention.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substituent is keto (i.e., =O), then 2 hydrogens on the atom are replaced.

When any variable (e.g., $R_4$) occurs more than one time in any constituent or formula for a compound, its definition at each occurrence is independent of its definition at every other occurrence. Thus, for example, if a group is shown to be substituted with $(R_4)_m$ and m is 0-3, then said group may optionally be substituted with up to three $R_4$ groups and $R_4$ at each occurrence is selected independently from the definition of $R_4$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio.

Unless otherwise indicated, the term "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio, and/or any of the alkyl substituents set out herein.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 10 rings, preferably 1 to 3 rings, including monocyclic alkyl, bicyclic alkyl (or bicycloalkyl) and tricyclic alkyl, containing a total of 3 to 20 carbons forming the ring, preferably 3 to 15 carbons, more preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl, cyclododecyl, cyclohexenyl,

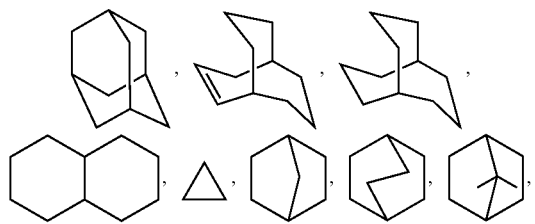

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2 v+1)).

Unless otherwise indicated, the term "aryl" as employed herein alone or as part of another group refers to monocyclic and bicyclic aromatic groups containing 6 to 10 carbons in the ring portion (such as phenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings
for example

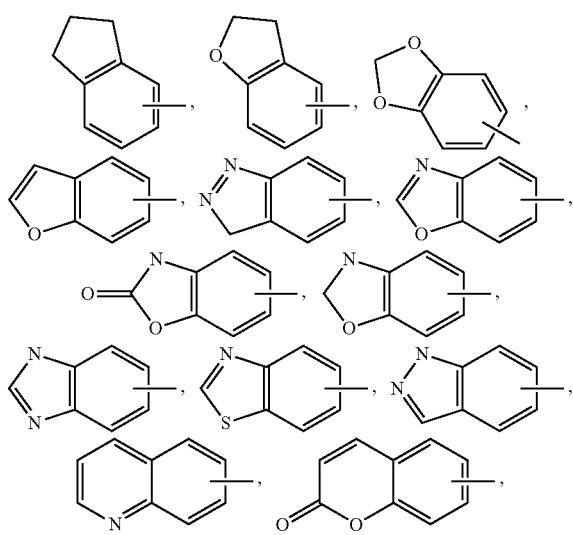

and may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl, and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, or thioalkyl. These substituents may be further substituted with a carboxylic acid and/or any of the $R^1$ groups or substituents for $R^1$ as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl, or hydroxy.

Unless otherwise indicated, the term "lower alkylthio," "alkylthio," "arylthio," or "aralkylthio" as employed herein alone or as part of another group includes any of the above alkyl, aralkyl, or aryl groups linked to a sulfur atom.

Unless otherwise indicated, the term "lower alkylamino," "alkylamino," "arylamino," or "arylalkylamino" as employed herein alone or as part of another group includes any of the above alkyl, aryl, or arylalkyl groups linked to a nitrogen atom.

As used herein, the term "heterocyclyl", "heterocyclic system" or "heterocyclic ring" is intended to mean a stable 3- to 14-membered monocyclic, bicyclic or tricyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom, which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S and is aromatic in nature.

Examples of heterocycles include, but are not limited to, 1H-indazole, 2-pyrrolidonyl, 2H,6H-1,5,2-dithiazinyl, 2H-pyrrolyl, 1H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl, tetrazolyl, and xanthenyl. In another aspect of the invention, the heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyrazolotriazinyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl.

The term "heterocyclylalkyl" or "heterocyclyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano" as used herein, refers to a —CN group.
The term "nitro" as used herein, refers to an —NO$_2$ group.
The term "hydroxy" as used herein, refers to an OH group.
The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., p. 1418, (1985), the disclosure of which is hereby incorporated by reference.

Any compound that can be converted in vivo to provide the bioactive agent (i.e., the compound of formula I) is a prodrug within the scope and spirit of the invention.

The term "prodrugs" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates, and the like.

Various forms of prodrugs are well known in the art and are described in:
a) *The Practice of Medicinal Chemistry*, Camille G. Wermuth et al., Ch. 31, (Academic Press, 1996);
b) *Design of Prodrugs*, edited by H. Bundgaard, (Elsevier, 1985);
c) *A Textbook of Drug Design and Development*, P. Krogsgaard-Larson and H. Bundgaard, eds. Ch. 5, pp. 113-191 (Harwood Academic Publishers, 1991); and
d) *Hydrolysis in Drug and Prodrug Metabolism*, Bernard Testa and Joachim M. Mayer, (Wiley-VCH, 2003).
Said references are incorporated herein by reference.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of formula I can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization. In addition, the compounds of formula I may exist in tautomeric form. For example, the compounds of the present invention may exist in the following form (formula I-t):

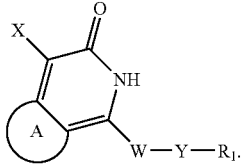

I-t

Such tautomeric forms of the formula I (formula I-t) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit MIP-1α or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis

Compounds of formula I of may be prepared as shown in the following reaction schemes and description thereof, as well as relevant literature procedures that may be used by one skilled in the art. Exemplary reagents and procedures for these reactions appear hereinafter and in the working Examples.

SCHEME I

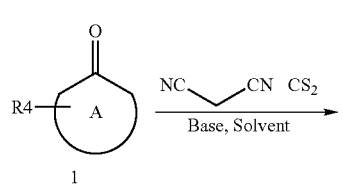

1

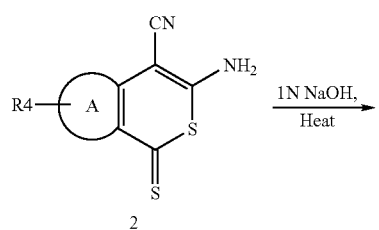

2

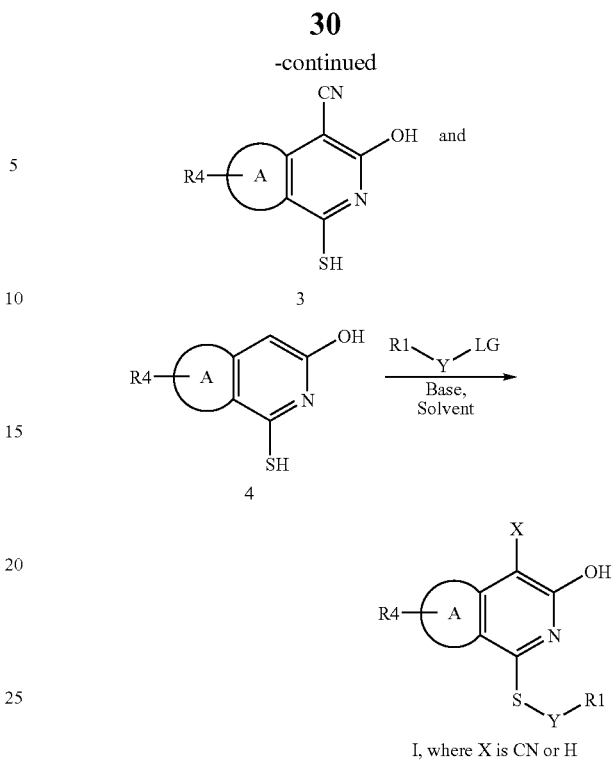

3

4

I, where X is CN or H

Scheme I describes a method for preparing intermediates 1 to 4 and compounds of formula I as described in the literature (Phosphour, Sulfur, and Silicon, 44:203-207 (1989)). A cyclic ketone intermediate 1 can be obtained commercially, prepared by methods known in the literature or other methods used by one skilled in the art. Formation of the thiopyran 2 can be obtained by treatment of ketone 1 with malononitrile, carbon disulfide, and an amine base, such as triethyl amine, solvent, such as methanol, and DMF. Subsequent treatment of the thiopyran 2 in refluxing aqueous NaOH gives the hydroxypyridine 3 and 4 as a mixture. Alkylation of the mixture of 3 and 4 with a appropriate electrophile, where LG is a leaving group such as Br, Cl, tosylate, or mesylate, can provide compounds of formula I, where X is CN or H.

SCHEME II

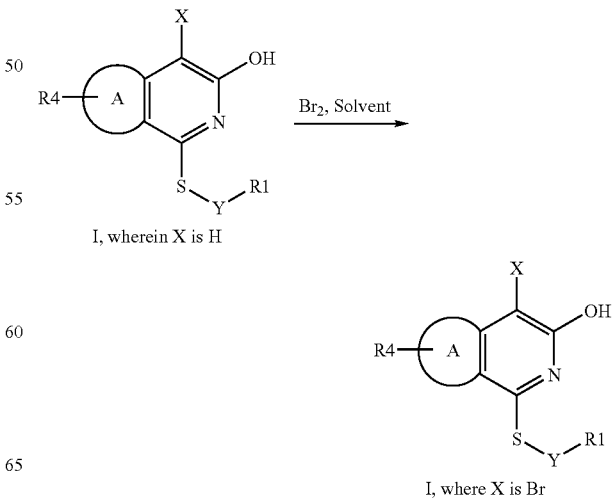

I, wherein X is H

I, where X is Br

-continued

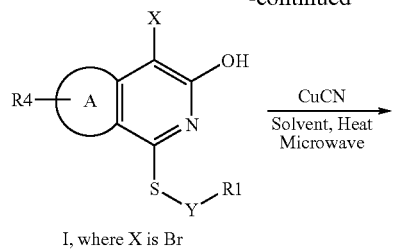

I, where X is Br

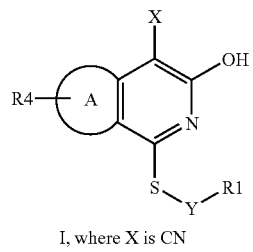

I, where X is CN

Scheme II describes another method for preparing compounds of formula I where X=Br or CN. A compound of formula I, where X is H, can be brominated with bromine to produce a compound of formula I, where X is bromine. The bromide compound of formula I can then be heated in the presence of CuCN at 200° C. with microwave irradiation to provide compounds of formula I, where X is CN.

SCHEME III

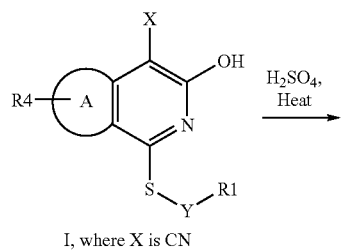

I, where X is CN

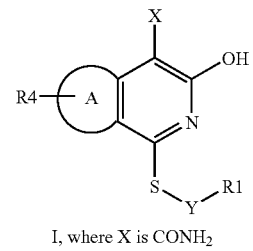

I, where X is CONH$_2$

Scheme III describes a method for preparing compounds of formula I, where X is CONH$_2$. Compounds of formula I, where X is CN, can be treated in 80% sulfuric acid with heat to provide compounds of formula I, where X is CONH$_2$.

SCHEME IV

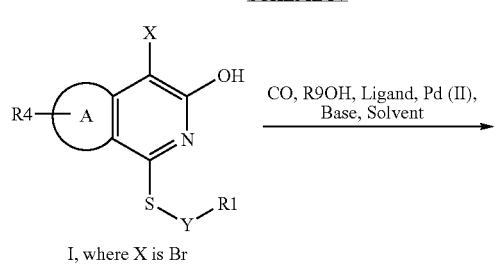

I, where X is Br

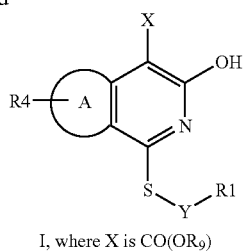

I, where X is CO(OR$_9$)

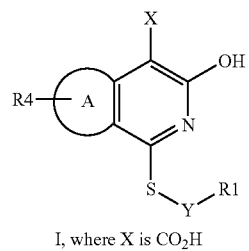

I, where X is CO$_2$H

Scheme IV describes a method for preparing compounds of formula I, where X is CO(ORG) or CO$_2$H. A compound of formula I, where X is Br, can be carbonylated with CO in the presence of a Pd catalyst, a base, an appropriate ligand and solvent, such as R$_9$OH, using conditions described in the art (*J. Org. Chem.*, 64: 120-125 (1999)) to provide a compound of formula I, where X is CO(OR$_9$). This compound can then be treated with NaOH in a solvent, such as methanol, to provide a compound of formula I, where X is CO$_2$H.

SCHEME V

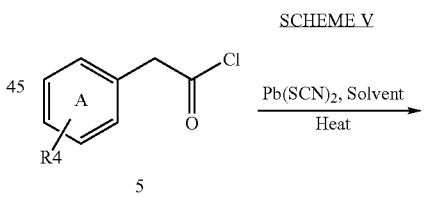

5

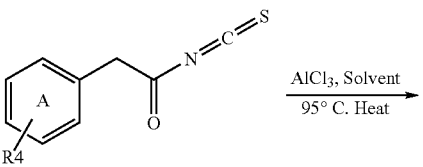

6

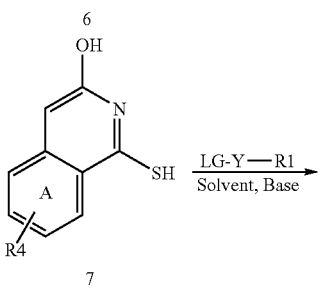

7

-continued

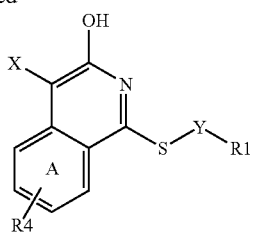

I, where X is H

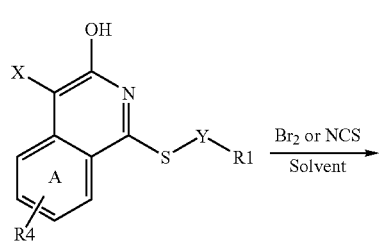

I, where X is H

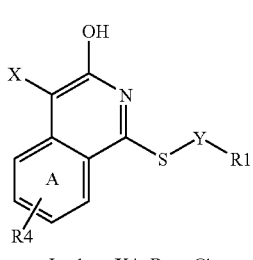

I, where X is Br or Cl

Scheme V describes a method for preparing intermediate 7 and compounds of formula I, where X is Cl or Br. Intermediate 6 can be prepared according to the conditions described in the art (*J. Org. Chem.*, 29(8):2261-2265 (1964)) starting with an acetylchloride (intermediate 5) and lead (II) thiocyanate. Cyclization of intermediate 6 under Friedel-Crafts acylation conditions can be used to produce intermediate 7. Intermediate 7 can then undergo alkylation using the appropriate electrophile, where LG is a leaving group such as Br, Cl, tosylate, or mesylate, to provide compounds of formula I, where X is H. Halogenation of this compound can then be conducted using the appropriate reagent to yield compounds of formula I, where X is Cl or Br.

SCHEME VI

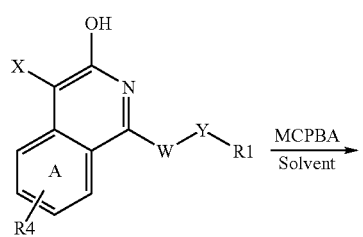

I, where W is S

-continued

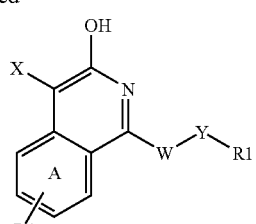

I, where W is SO or $SO_2$

Scheme VI describes a method for preparing compounds of formula I, where W is SO or $SO_2$. A compound of formula I, where W is S, can be treated with 1-3 equivalent of MCPBA in an appropriate solvent, such dichloromethane, to provide compounds of formula I, where W is SO or $SO_2$.

SCHEME VII

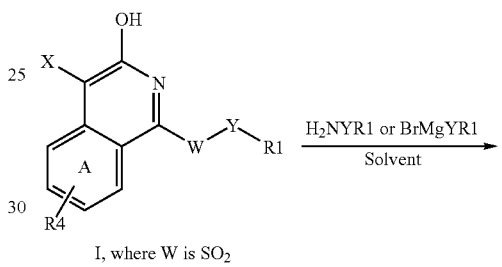

I, where W is $SO_2$

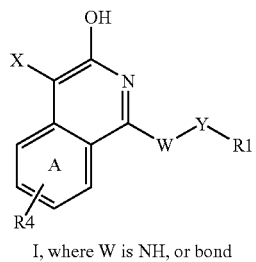

I, where W is NH, or bond

Scheme VII describes a method for preparing compounds of formula I, where W is NH or a bond. A compound of formula I, where W is $SO_2$, is treated with a nucleophile, such as $R1YNH_2$ or R1YMgBr, in a solvent, such as THF or DMF, gives compounds of formula I, where W is NH or bond.

SCHEME VIII

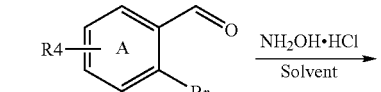

8

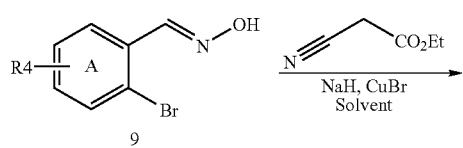

9

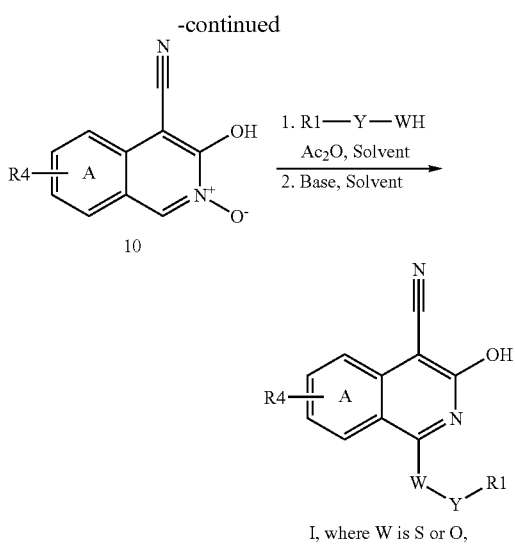

Scheme VIII describes a method for preparing intermediates 9 to 10 and compounds of formula I, where W is S or O. Intermediate 10 can be prepared according to the conditions described in the art (*Synthesis*, 760 (1977)) starting from the aldehyde 8. Intermediate 10 can then be reacted with the appropriate thiol or alcohol to provide compounds of formula I, where W is S or O.

EXAMPLES

The following working Examples serve to better illustrate, but not limit, some of the preferred embodiments of the present invention.

ABBREVIATIONS

The following abbreviations are employed in the Examples and elsewhere herein:
DMF=N,N-dimethylformamide
MeOH=methanol
EtOH=ethanol
Et$_3$N=triethylamine
RT=room temperature
h or hr=hour(s)
mL=milliliter
mmol=millimole(s)
N=normal
HCl=hydrochloric acid
g=gram(s)
min=minute(s)
HPLC=high performance liquid chromatography
NMR=nuclear magnetic resonance.
LC/MS=high performance liquid chromatography/mass spectrometry
K$_2$CO$_3$=potassium carbonate
Br$_2$=bromine
CuCN=copper cyanide
CD$_4$OD=deuterated methanol
ppm=parts per million
MHz=megahertz
Ar=argon
HOAc or AcOH=acetic acid
EtOAc=ethyl acetate
Na$_2$SO$_4$=sodium sulfate
MCPBA=meta-chloroperbenzoic acid
NaHCO$_3$=sodium bicarbonate
sat or sat'd=saturated
aq.=aqueous
Et$_2$O=diethyl ether
CuBr=copper bromide
NaH=sodium hydride
MeCN=acetonitrile
mg=milligram(s)
TFA=trifluoroacetic acid
CDCl$_3$=deuterated chloroform
DMSO-d$_6$=dimethylsulfoxide-d$_6$
DCM=dichloromethane
MgSO$_4$=magnesium sulfate
DPPP=1,3-bis(diphenylphosphino)propane
DBU=1,8 diazabicyclic[5,4,0]undec-7-ene
NaOH=sodium hydroxide
NMP=N-methylpyrrolidinon
HCN=hydrogen cyanide
Hz=hertz
J=coupling constant
Pd(AcO)$_2$=palladium acetate

Examples 1 and 2

1-(2-Chloro-benzylsulfanyl)-3-hydroxy-5,6,7,8-tetrahydro-isoquinoline-4-carbonitrile and 1-(2-Chloro-benzylsulfanyl)-5,6,7,8-tetrahydro-isoquinolin-3-ol, respectively

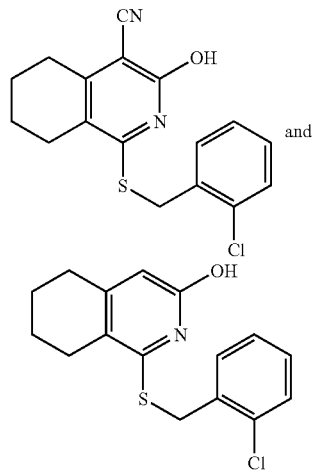

Step 1: Mixture of 3-hydroxy-1-mercapto-5,6,7,8-tetrahydro-isoquinoline-4-carbonitrile and 1-mercapto-5,6,7,8-tetrahydro-isoquinolin-3-ol

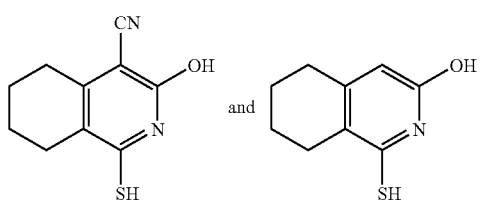

To a stirred solution of cyclohexanone (17 mmol) and malononitrile (17 mmol) in 5 mL of MeOH and 1 mL of DMF was added 3.3 mL carbon disulfide followed by the slow addition of 1 mL of Et₃N. Upon completion of addition, the solution was stirred at RT for 36 h. At the conclusion of this period, the resulting red precipitate was collected by filtration and then washed with MeOH. The red solid filter cake was then taken up in 50 mL of 1N NaOH. The resulting mixture was stirred at 150° C. for 7 h and then cooled to RT. Once at the prescribed temperature, the resulting red solution was acidified with 6 N HCl. The resulting yellow precipitate was collected by filtration, washed with water and then dried in vacuum to provide the title mixture (0.85 g, 1:1 mixture of 3-hydroxy-1-mercapto-5,6,7,8-tetrahydro-isoquinoline-4-carbonitrile (13%) and 1-mercapto-5,6,7,8-tetrahydro-isoquinolin-3-ol (14%). 3-Hydroxy-1-mercapto-5,6,7,8-tetrahydro-isoquinoline-4-carbonitrile LC/MS m/z 207 (M+H). 1-Mercapto-5,6,7,8-tetrahydro-isoquinolin-3-ol. LC/MS m/z 182 (M+H).

Step 2: Examples 1 and 2

To a mixture of the crude mixture of Step 1 above (3-hydroxy-1-mercapto-5,6,7,8-tetrahydro-isoquinoline-4-carbonitrile (0.12 mmol) and 1-mercapto-5,6,7,8-tetrahydro-isoquinolin-3-ol (0.14 mmol)) and K₂CO₃ (0.36 mmol) in 5 mL of EtOH was added 2-chlorobenzyl bromide (0.30 mmol). Upon completion of addition, the reaction mixture was stirred at RT for 1 h. After this time, the reaction mixture was filtered, and the filtrate was concentrated under reduced pressure to yield a residue. The residue was purified by preparative HPLC (Gradient Solvent System: From 30% A: 70% B to 0% A: 100% B; [A=10% MeOH/90% H₂O+0.1% TFA]; [B=90% MeOH/10% H₂O+0.1% TFA]; detection at 220 nm: 10 min gradient; Phenomenex Luna AXIA 30×100 mm) to provide Examples 1 (6 mg, 15%) and 2 (7 mg, 16%) as yellow solids. Example 1: ¹H NMR (400 MHz, CD₃OD) δ ppm 7.57 (s, 1H) 7.34-7.43 (m, 1H) 7.16-7.29 (m, 2H). 4.56 (s, 2H) 2.78 (s, 2H) 2.41 (s, 2H) 1.77 (s, 4H). LC/MS m/z 331 (M+H). Example 2: ¹H NMR (400 MHz, CD₃OD) δ ppm 7.30-7.44 (m, 1H) 7.07-7.29 (m, 3H) 6.35 (s, 1H) 4.34 (s, 2H) 2.65 (t, J=5.94 Hz, 2H) 2.35 (t, J=6.19 Hz, 2H) 1.49-1.70 (m, 4H). LC/MS m/z 306 (M+H).

Example 3

1-(2-Chlorobenzylthio)-3-hydroxy-5,6,7,8-tetrahydroisoquinoline-4-carboxamide

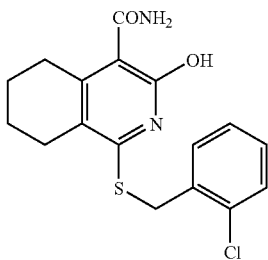

A mixture of Example 1 (0.03 mmol) in 5 mL of 80% H₂SO₄ was stirred for 30 min at 140° C. with microwave irradiation. The mixture was then purified via HPLC in the manner described in Step 2, Examples 1 and 2, to provide Example 3 (6 mg, 58%). ¹H NMR (400 MHz, CD₃OD) δ ppm 7.44 (d, J=7.15 Hz, 1H) 7.37 (d, J=7.70 Hz, 1H) 7.13-7.25 (m, 2H) 4.47 (s, 2H) 2.74 (s, 2H) 2.40 (s, 2H) 1.67 (s, 4H). LC/MS m/z 349 (M+H).

Example 4

4-Bromo-1-(2-chlorobenzylthio)-5,6,7,8-tetrahydroisoquinolin-ol

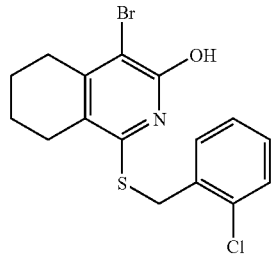

To a solution of Example 2 (1.5 mmol) in 10 mL of DCM was added Br₂. The solution was stirred for 2 h at RT and then concentrated to provide a residue. The residue was purified via HPLC in the manner described in Step 2, Examples 1 and 2, to provide Example 4 (125 mg, 33%). ¹H NMR (400 MHz, CD₃OD) δ ppm 7.36 (dd, J=7.83, 1.52 Hz, 1H) 7.21-7.25 (m, 1H) 7.19 (dd, J=5.05, 1.77 Hz, 1H) 7.14-7.18 (m, 1H) 4.37 (s, 2H) 2.66 (t, J=6.44 Hz, 3H) 2.36 (t, J=6.44 Hz, 3H) 1.63-1.71 (m, 2H) 1.56 (s, 2H). LC/MS m/z 385 (M+H).

Example 5

Methyl 1-(2-chlorobenzylthio)-3-hydroxy-5,6,7,8-tetrahydroisoquinoline-4-carboxylate

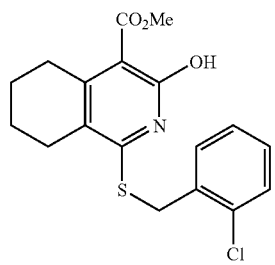

A mixture of Example 4 (0.39 mmol), Pd(OAc)₂ (0.19 mmol), DPPP (0.15 mmol) and DBU (0.46 mmoL) was stirred for 18 h at 85° C. under 25 psi of CO. After this time, the mixture was cooled to RT, filtered, and concentrated to provide a residue. The residue was purified by preparative HPLC (Gradient Solvent System: From 50% A: 50% B to 0% A: 100% B; [A=10% MeOH/90% H₂O+0.1% TFA]; [B=90% MeOH/10% H₂O+0.1% TFA]; detection at 220 nm: 10 min gradient; Phenomenex Luna AXIA 30×100 mm) over 10 min. to provide Example 5 (6 mg, 4%). ¹H NMR (400 MHz, CD₃OD) δ ppm 7.48-7.54 (m, 1H) 7.34-7.40 (m, 1H) 7.16-

7.24 (m, 2H) 4.51 (s, 2H) 3.88 (s, 3H) 2.73 (t, J=5.77 Hz, 2H) 2.38-2.46 (m, 2H) 1.63-1.73 (m, 4H). LC/MS m/z 364 (M+H).

Example 6

1-(2-Chlorobenzylthio)-3-hydroxy-5,6,7,8-tetrahydroisoquinoline-4-carboxylic acid

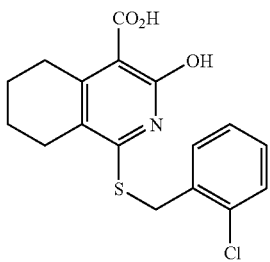

To a solution of Example 5 (0.08 mmol) in 5 mL of methanol was added 1N NaOH (0.8 mmol). The solution was stirred for 18 h at 90° C. and cooled to RT, and concentrated to provide a residue. The residue was purified by preparative HPLC (Gradient Solvent System: From 50% A: 50% B to 0% A: 100% B; [A=10% MeOH/90% $H_2O$+0.1% TFA]; [B=90% MeOH/10% $H_2O$+0.1% TFA]; detection at 220 nm: 10 min gradient; Phenomenex Luna AXIA 30×100 mm) to provide Example 6 (2 mg, 70%). $^1$H NMR (400 MHz, $CD_3OD$) δ ppm 7.39 (dd, J=7.58, 1.52 Hz, 2H) 7.17-7.27 (m, 2H) 4.48 (s, 2H) 3.10 (t, J=6.19 Hz, 2H) 2.45 (t, J=6.06 Hz, 2H) 1.64 (s, 4H). LC/MS m/z 350 (M+H).

Examples 7 to 96

Examples 7 to 96 in Table 1 can be prepared according to the procedures described in Examples 1 to 6 or by other similar methods known to one skilled in the art, with other appropriate reagent. NMR Spectra data are reported in δ ppm using a 400 MHz spectrometer and $CD_4OD$ as the solvent. In the structures set forth in Table 1, the "—O" attached to the carbon adjacent to the nitrogen in the bicyclic or tricyclic core is used to denote an "—OH" group as indicated in Formula I. Similarly, in the structures set forth in Table 1, the "N" adjacent to the carbon atom substituted with =O in the bicyclic or tricyclic core is used to denote an "NH" moiety as indicated in Formula I-t.

TABLE 1

| Example | Structure | MS (M + H) | $^1$H NMR | Purity |
| --- | --- | --- | --- | --- |
| 7 | 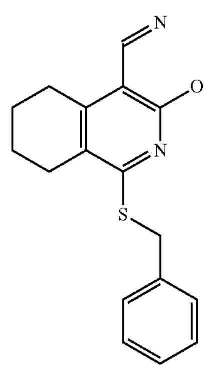 | 297 | 7.38 (d, J = 7.03 Hz, 2 H) 7.27 (t, J = 7.25 Hz, 2 H) 7.22 (d, J = 7.47 Hz, 1 H) 4.43 (s, 2 H) 2.78 (s, 2 H) 2.43 (s, 2 H) 1.77 (t, J = 3.30 Hz, 4 H) | 95 |
| 8 | 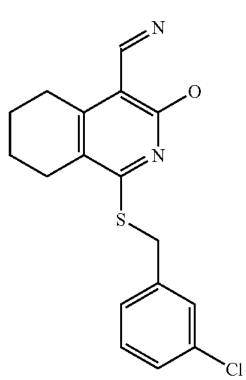 | 331 | 7.58 (s, 1 H) 7.35-7.45 (m, 1 H) 7.16-7.31 (m, 2 H) 4.57 (s, 2 H) 2.79 (s, 2 H) 2.42 (s, 2 H) 1.77 (s, 4 H) | 98 |

TABLE 1-continued

| Example | Structure | MS (M + H) | ¹H NMR | Purity |
|---|---|---|---|---|
| 9 | 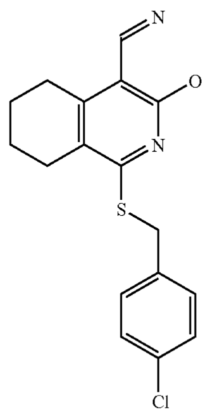 | 331 | 7.38 (d, J = 8.59 Hz, 2 H) 7.26 (d, J = 8.59 Hz, 2 H) 2.78 (s, 2 H) 2.39-2.48 (m, 2 H) 1.74-1.82 (m, 4 H) | 99 |
| 10 | 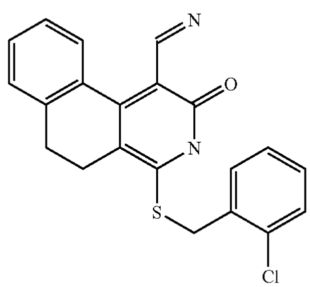 | 379 | 8.28 (d, J = 7.70 Hz, 1 H) 7.49-7.59 (m, 1 H) 7.28-7.46 (m, 4 H) 7.19-7.28 (m, 2 H) 4.58 (s, 2 H) 2.70 (s, 2 H) 2.54-2.65 (m, 2 H) | 98 |
| 11 | 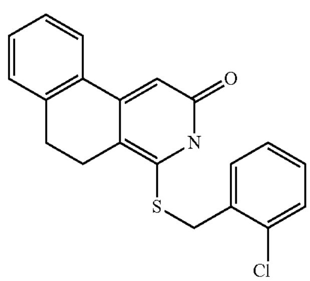 | 354 | 7.72-7.78 (m, 1 H) 7.36 (d, J = 7.15 Hz, 1 H) 7.31 (t, J = 2.75 Hz, 2 H) 7.16-7.22 (m, 3 H) 7.14 (d, J = 6.60 Hz, 1 H) 6.85 (s, 1 H) 4.32 (s, 1 H) 2.50 (s, 4 H) | 98 |
| 12 | 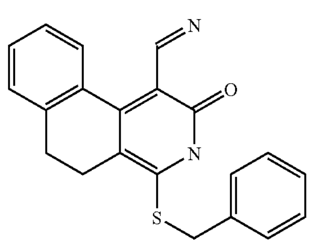 | 345 | 8.27 (d, J = 8.08 Hz, 1 H) 7.15-7.53 (m, 8 H) 4.44 (s, 2 H) 2.66-2.77 (m, 2 H) 2.55-2.65 (m, 2 H) | 98 |
| 13 | 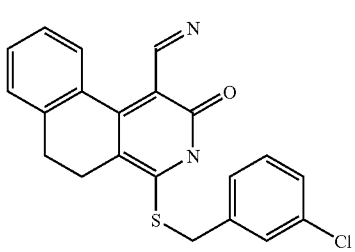 | 379 | 8.29 (d, J = 7.83 Hz, 1 H) 7.16-7.51 (m, 7 H) 4.46 (s, 2 H) 2.70-2.83 (m, 2 H) 2.58-2.70 (m, 2 H) | 98 |

TABLE 1-continued

| Example | Structure | MS (M + H) | $^1$H NMR | Purity |
|---|---|---|---|---|
| 14 | 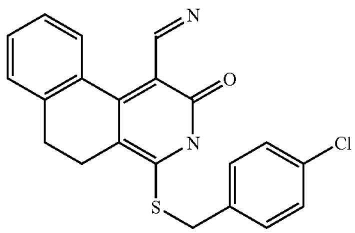 | 379 | 7.05-7.52 (m, 8 H) 4.44 (s, 2 H) 2.76 (d, J = 4.80 Hz, 2 H) 2.59-2.67 (m, 2 H) | 97 |
| 15 | 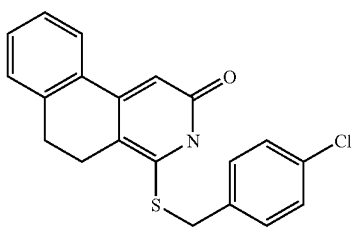 | 354 | 7.68-7.80 (m, 1 H) 7.25-7.39 (m, 3 H) 7.23 (s, 4 H) 6.83 (s, 1 H) 4.21 (s, 2 H) 2.53-2.70 (m, 4 H) | 97 |
| 16 | 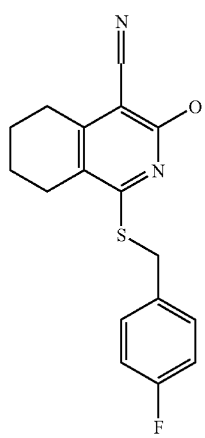 | 315 | 7.37-7.49 (m, 2 H) 7.00 (t, J = 8.79 Hz, 2 H) 4.37-4.52 (m, 2 H) 2.79 (s, 2 H) 2.43 (s, 2 H) 1.78 (s, 4 H) | 99 |
| 17 | 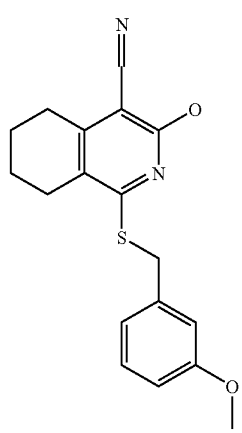 | 327 | 7.29 (d, J = 8.25 Hz, 2 H) 6.83 (d, J = 8.79 Hz, 2 H) 4.38 (s, 2 H) 3.75 (s, 3 H) 2.78 (s, 2 H) 2.42 (s, 2 H) 1.77 (s, 4 H) | 90 |

TABLE 1-continued

| Example | Structure | MS (M + H) | ¹H NMR | Purity |
|---|---|---|---|---|
| 18 | 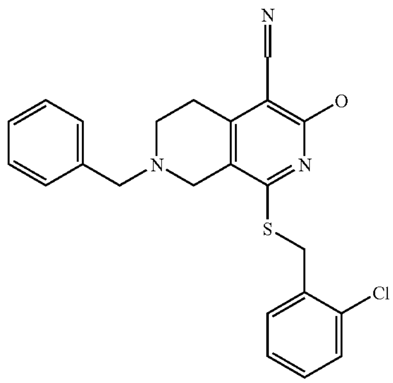 | 422 | 7.58 (dd, J = 7.47, 1.76 Hz, 1 H) 7.49 (s, 5 H) 7.40 (d, J = 9.23 Hz, 1 H) 7.19-7.29 (m, 2 H) 4.65 (s, 2 H) 4.41 (s, 2 H) 4.04 (s, 2 H) 3.50 (s, 2 H) 3.17 (t, J = 6.15 Hz, 2 H) | 95 |
| 19 | 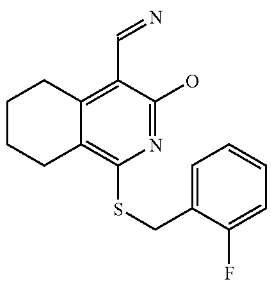 | 315 | 7.49 (s, 1 H) 7.21-7.32 (m, 1 H) 7.00-7.13 (m, 2 H) 4.48 (s, 2 H) 2.79 (s, 2 H) 2.42 (s, 2 H) 1.77 (s, 4 H) | 98 |
| 20 | 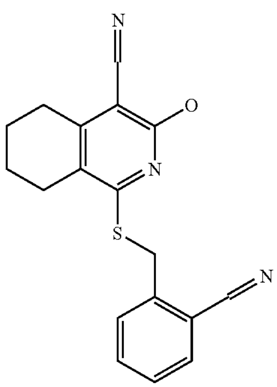 | 322 | 7.71 (d, J = 8.25 Hz, 2 H) 7.58 (t, J = 7.97 Hz, 1 H) 7.42 (t, J = 7.70 Hz, 1 H) 4.64 (s, 2 H) 2.80 (s, 2 H) 2.44 (s, 2 H) 1.78 (s, 5 H) | 99 |
| 21 | 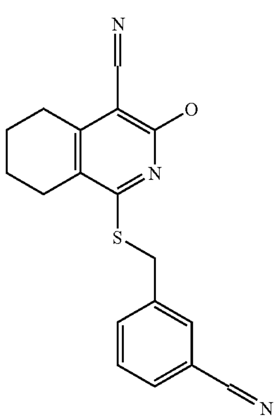 | 322 | 7.82 (s, 1 H) 7.74 (d, J = 7.15 Hz, 1 H) 7.58 (d, J = 7.70 Hz, 1 H) 4.49 (s, 2 H) 2.79 (t, J = 5.22 Hz, 2 H) 2.37-2.48 (m, 2 H) 1.78 (s, 4 H) | 99 |

TABLE 1-continued

| Example | Structure | MS (M + H) | ¹H NMR | Purity |
|---|---|---|---|---|
| 22 | 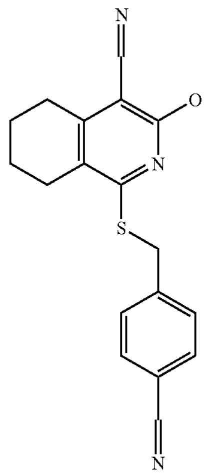 | 322 | 7.82 (s, 1 H) 7.74 (d, J = 7.15 Hz, 1 H) 7.58 (d, J = 7.70 Hz, 1 H) 4.49 (s, 2 H) 2.79 (t, J = 5.22 Hz, 2 H) 2.37-2.48 (m, 2 H) 1.78 (s, 4 H) | 99 |
| 23 | 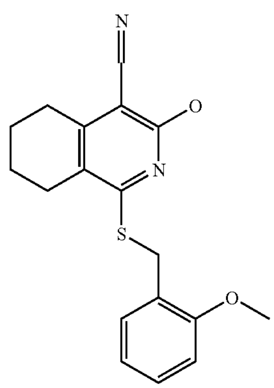 | 327 | 7.82 (s, 1 H) 7.74 (d, J = 7.15 Hz, 1 H) 7.58 (d, J = 7.70 Hz, 1 H) 4.49 (s, 2 H) 2.79 (t, J = 5.22 Hz, 2 H) 2.37-2.48 (m, 2 H) 1.78 (s, 4 H) | 98 |
| 24 | 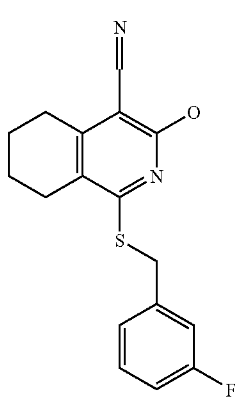 | 315 | 7.25-7.33 (m, 1 H) 7.11-7.22 (m, 2 H) 6.89-7.01 (m, 1 H) 4.45 (s, 2 H) 2.79 (s, 2 H) 2.44 (s, 2 H) 1.78 (s, 4 H) | 80 |

TABLE 1-continued
| Example | Structure | MS (M + H) | ¹H NMR | Purity |
|---|---|---|---|---|
| 25 | 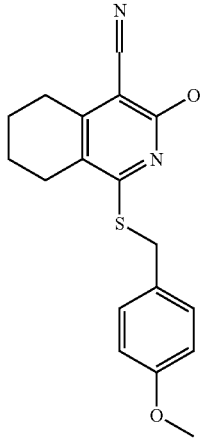 | 327 | 7.18 (t, J = 7.70 Hz, 1 H) 6.90-7.00 (m, 2 H) 6.75-6.81 (m, 1 H) 4.41 (s, 2 H) 3.75 (s, 3 H) 2.78 (s, 2 H) 2.43 (s, 2 H) 1.77 (s, 4 H) | 94 |
| 26 | 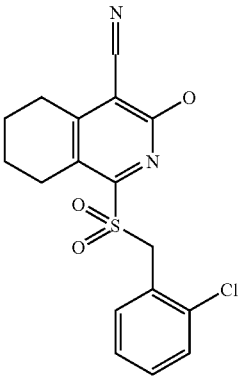 | 363 | 7.51 (d, J = 7.70 Hz, 1 H) 7.45 (d, J = 8.25 Hz, 1 H) 7.29-7.40 (m, J = 12.09, 6.05 Hz, 2 H) 5.04 (s, 2 H) 2.97 (t, J = 6.32 Hz, 2 H) 2.89 (t, J = 6.32 Hz, 2 H) 1.74-1.84 (m, 2 H) 1.65-1.74 (m, 2 H) | 98 |
| 27 | 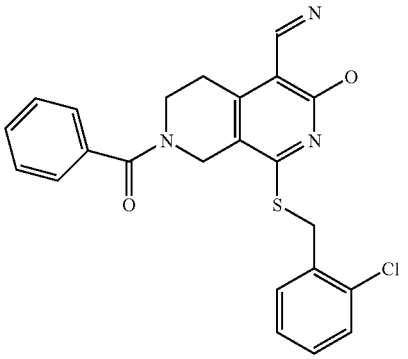 | 436 | 7.36-7.53 (m, J = 7.83 Hz, 7 H) 7.23 (s, 2 H) 4.57 (s, 2 H) 4.28-4.44 (m, 1 H) 3.97 (s, 1 H) 3.65 (s, 2 H) 2.97 (s, 2 H) | 98 |
| 28 | 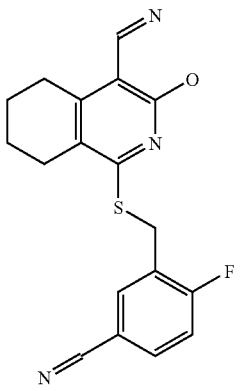 | 340 | 8.05 (d, J = 5.50 Hz, 1 H) 7.62-7.74 (m, 1 H) 7.22-7.35 (m, 1 H) 4.50 (s, 2 H) 2.80 (s, 2 H) 2.43 (s, 2 H) 1.79 (s, 4 H) | 98 |

TABLE 1-continued

| Example | Structure | MS (M + H) | ¹H NMR | Purity |
|---|---|---|---|---|
| 29 | 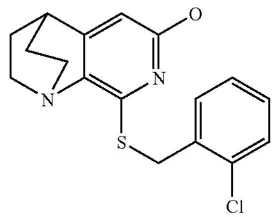 | 333 | 7.41 (d, J = 7.70 Hz, 1 H) 7.34 (d, J = 7.15 Hz, 1 H) 7.18-7.29 (m, 2 H) 6.55 (s, 1 H) 4.53 (s, 2 H) 3.55-3.66 (m, 2 H) 3.34-3.38 (m, 1 H) 2.73-2.86 (m, 2 H) 2.13-2.24 (m, 2 H) 1.73 (t, J = 10.44 Hz, 2 H) | 98 |
| 30 | 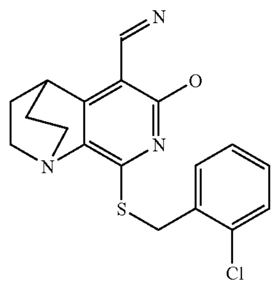 | 358 | 7.59 (dd, J = 7.15, 2.20 Hz, 1 H) 7.38 (d, J = 7.70 Hz, 1 H) 7.17-7.26 (m, 2 H) 3.42-3.52 (m, 2 H) 3.37-3.41 (m, 1 H) 2.84-2.97 (m, 2 H) 2.08-2.19 (m, 2 H) 1.65-1.76 (m, 2 H) | 98 |
| 31 | 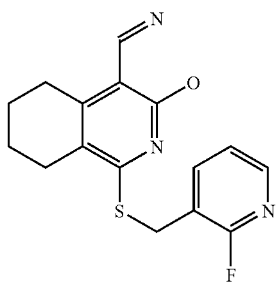 | 316 | 7.97-8.14 (m, 2 H) 7.21 (t, J = 5.50 Hz, 1 H) 4.47 (s, 2 H) 2.79 (t, J = 5.22 Hz, 2 H) 2.37-2.50 (m, 2 H) 1.79 (s, 4 H) | 98 |
| 32 | 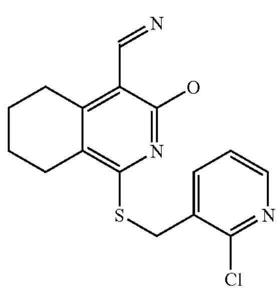 | 332 | 8.23 (dd, J = 4.83, 1.76 Hz, 1 H) 8.10 (d, J = 6.59 Hz, 1 H) 7.85 (s, 1 H) 7.30 (dd, J = 7.91, 4.83 Hz, 1 H) 4.55 (s, 2 H) 2.72-2.87 (m, 2 H) 2.37-2.50 (m, 2 H) 1.79 (d, J = 3.52 Hz, 4 H) | 98 |
| 33 | 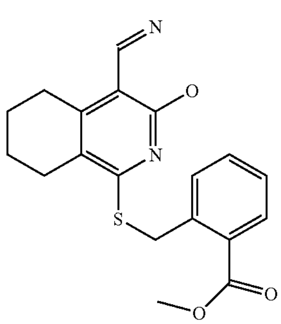 | 355 | 7.86-7.97 (m, 1 H) 7.62 (s, 1 H) 7.42-7.49 (m, 1 H) 7.30-7.37 (m, 1 H) 4.83 (s, 2 H) 3.85-3.91 (m, 3 H) 2.77 (s, 2 H) 2.34-2.41 (m, 2 H) 1.74 (s, 4 H) | 90 |

TABLE 1-continued

| Example | Structure | MS (M + H) | ¹H NMR | Purity |
|---|---|---|---|---|
| 34 | 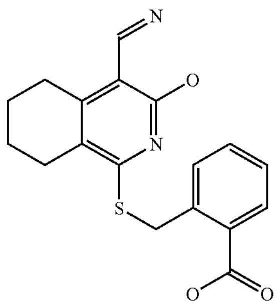 | 341 | 7.94 (d, J = 7.70 Hz, 1 H) 7.58 (d, J = 7.15 Hz, 1 H) 7.43 (t, J = 7.42 Hz, 1 H) 7.31 (t, J = 7.42 Hz, 1 H) 4.83 (s, 2 H) 2.76 (s, 2 H) 2.37 (s, 2 H) 1.73 (s, 4 H) | 95 |
| 35 | 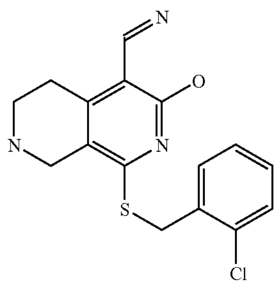 | 332 | 7.58-7.67 (m, 1 H) 7.14-7.33 (m, 2 H) 4.09 (s, 2 H) 3.50 (t, J = 6.32 Hz, 2 H) 3.14 (t, J = 6.32 Hz, 2 H) | 95 |
| 36 | 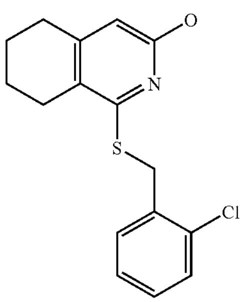 | 306 | | 97 |
| 37 | 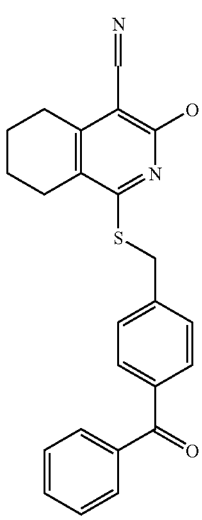 | 401 | | 53.9 |

TABLE 1-continued

| Example | Structure | MS (M + H) ¹H NMR | Purity |
|---------|-----------|-------------------|--------|
| 38 | 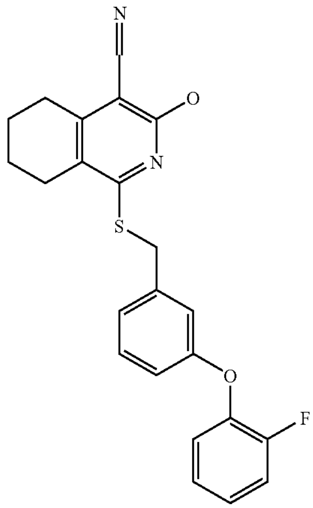 | 407 | 55.1 |
| 39 | 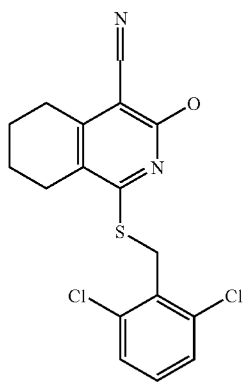 | 366 | 89.2 |
| 40 | 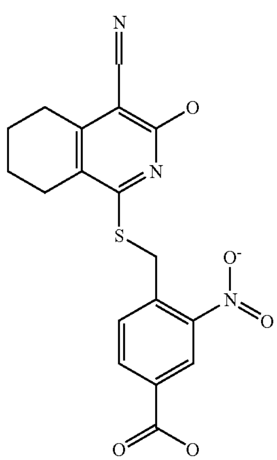 | 386 | 100.0 |

TABLE 1-continued

| Example | Structure | MS (M + H) | ¹H NMR | Purity |
|---|---|---|---|---|
| 41 | 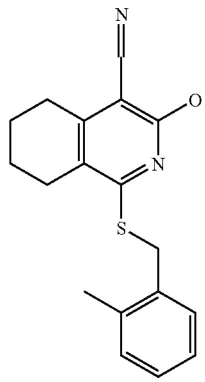 | 311 | | 100.0 |
| 42 | 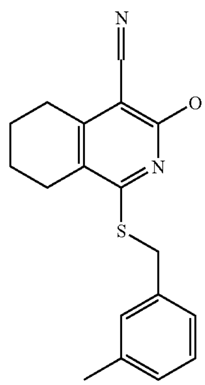 | 311 | | 100.0 |
| 43 | 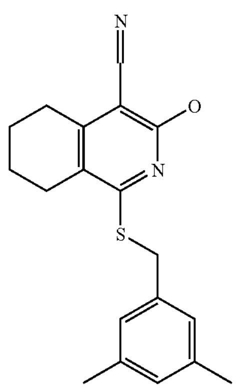 | 325 | | 100.0 |
| 44 | 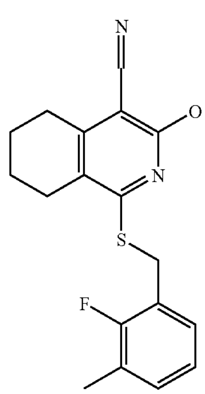 | 329 | | 100.0 |

TABLE 1-continued
| Example | Structure | MS (M + H) | ¹H NMR | Purity |
|---------|-----------|------------|--------|--------|
| 45 | 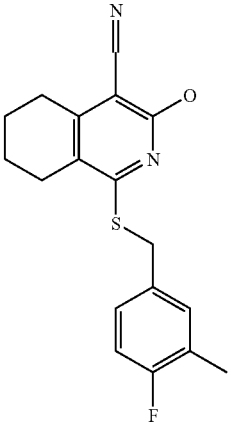 | 329 | | 100.0 |
| 46 | 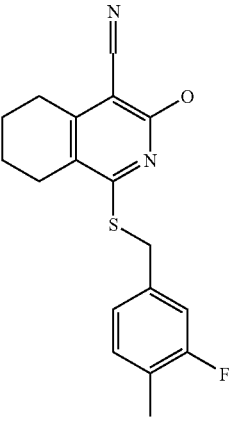 | 329 | | 100.0 |
| 47 | 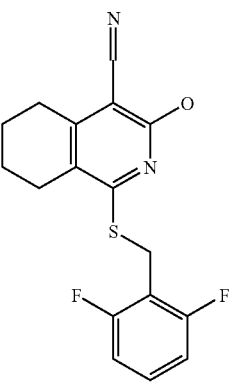 | 333 | | 97.4 |

TABLE 1-continued
| Example | Structure | MS (M + H) ¹H NMR | Purity |
|---|---|---|---|
| 48 | 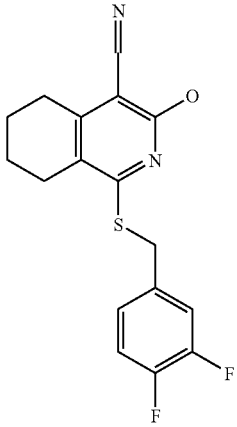 | 333 | 100.0 |
| 49 | 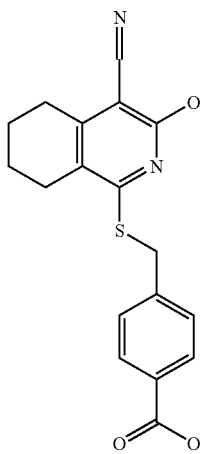 | 341 | 97.1 |
| 50 | 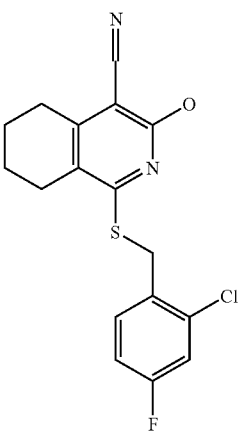 | 349 | 100.0 |

TABLE 1-continued

| Example | Structure | MS (M + H) ¹H NMR | Purity |
|---|---|---|---|
| 51 | 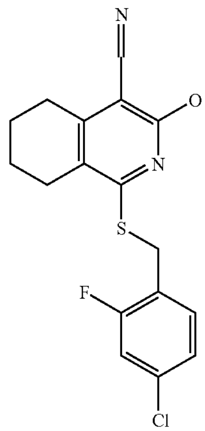 | 349 | 100.0 |
| 52 | 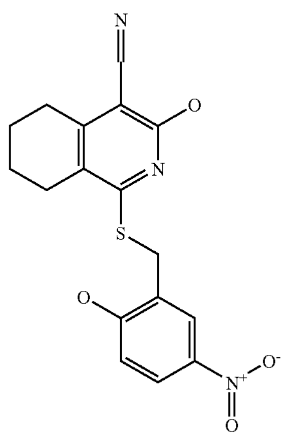 | 358 | 100.0 |
| 53 | 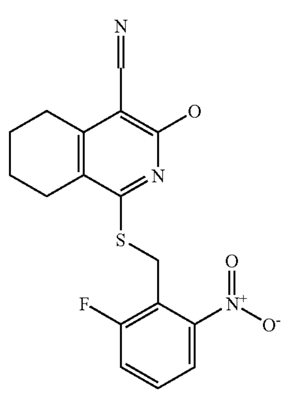 | 360 | 96.0 |

TABLE 1-continued

| Example | Structure | MS (M + H) | ¹H NMR | Purity |
|---------|-----------|------------|--------|--------|
| 54 | 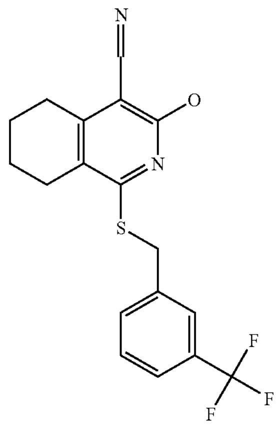 | 365 | | 100.0 |
| 55 | 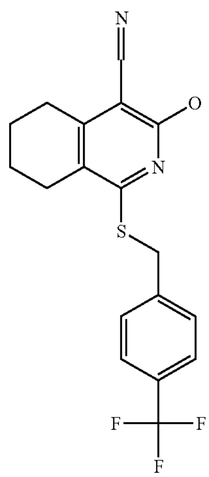 | 365 | | 100.0 |
| 56 | 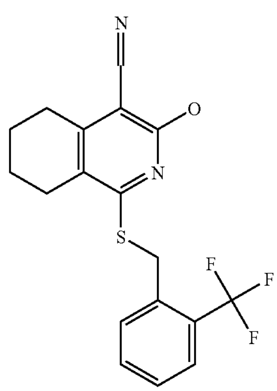 | 365 | | 100.0 |

TABLE 1-continued

| Example | Structure | MS (M + H) | ¹H NMR | Purity |
|---|---|---|---|---|
| 57 | 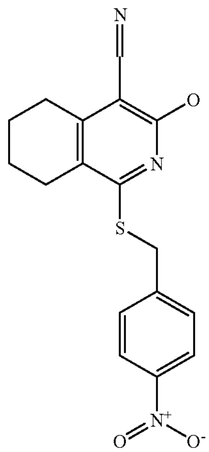 | 342 | | 53.6 |
| 58 | 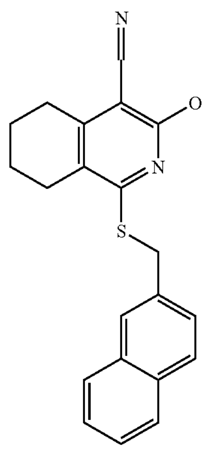 | 347 | | 54.7 |
| 59 | 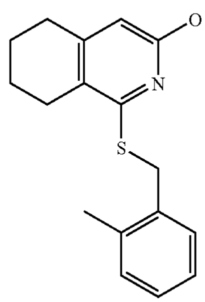 | 286 | | 100.0 |
| 60 | 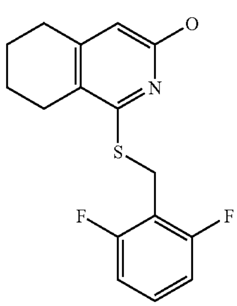 | 308 | | 100.0 |

TABLE 1-continued

| Example | Structure | MS (M + H) | ¹H NMR | Purity |
|---|---|---|---|---|
| 61 | 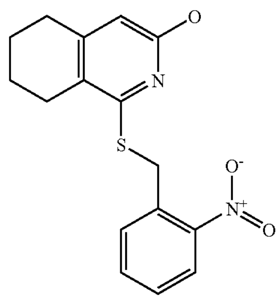 | 317 | | 100.0 |
| 62 | 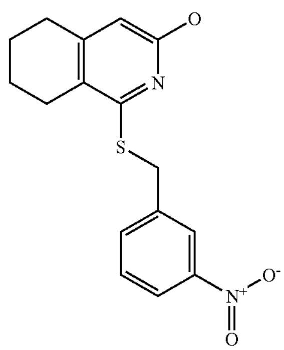 | 317 | | 100.0 |
| 63 | 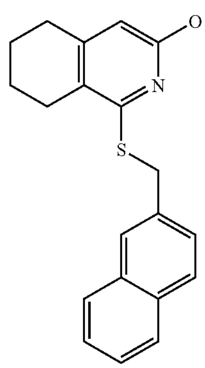 | 322 | | 100.0 |
| 64 | 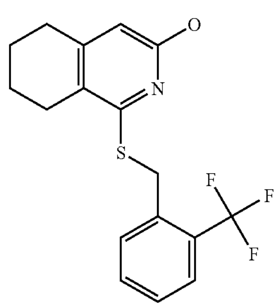 | 340 | | 100.0 |
| 65 | 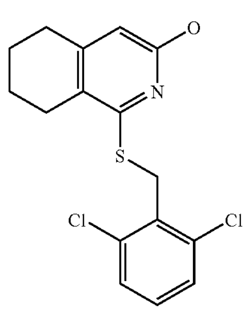 | 341 | | 100.0 |

TABLE 1-continued

| Example | Structure | MS (M + H) | ¹H NMR | Purity |
|---|---|---|---|---|
| 66 | 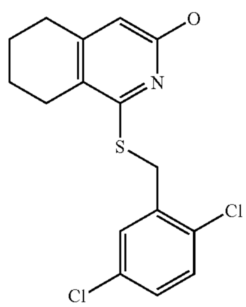 | 341 | | 100.0 |
| 67 | 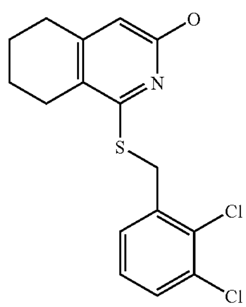 | 341 | | 100.0 |
| 68 | 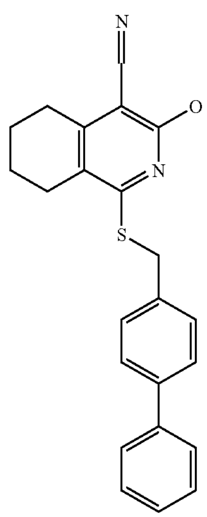 | 373 | | 100.0 |
| 69 | 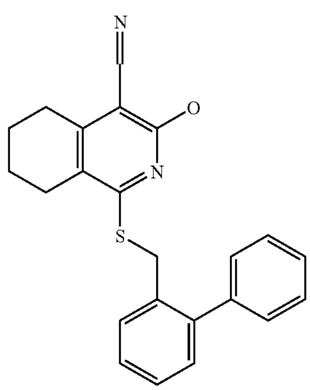 | 373 | | 100.0 |

TABLE 1-continued
| Example | Structure | MS (M + H) | ¹H NMR | Purity |
|---------|-----------|------------|--------|--------|
| 70 | 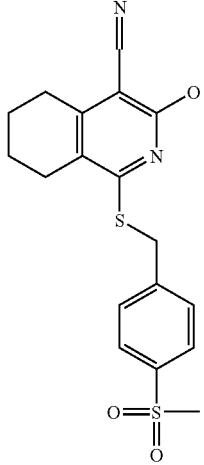 | 375 | | 91.5 |
| 71 | 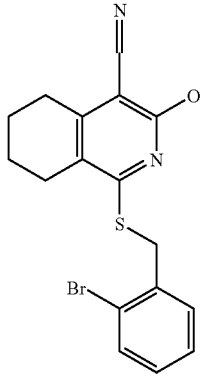 | 376 | | 100.0 |
| 72 | 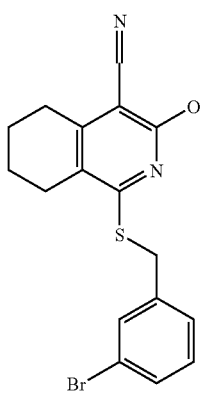 | 376 | | 100.0 |

TABLE 1-continued

| Example | Structure | MS (M + H) | ¹H NMR | Purity |
|---------|-----------|------------|--------|--------|
| 73 | 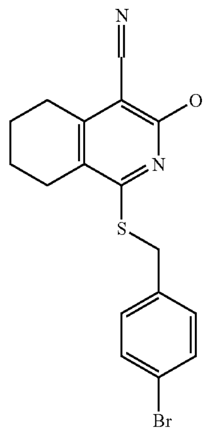 | 376 | | 100.0 |
| 74 | 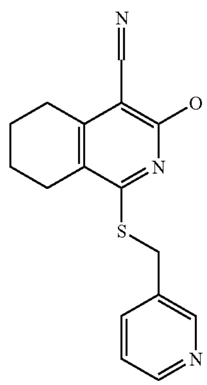 | 298 | | 100.0 |
| 75 | 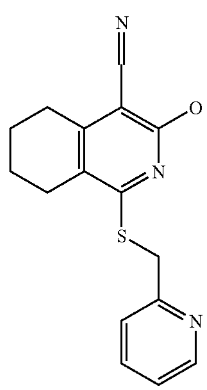 | 298 | | 100.0 |
| 76 | 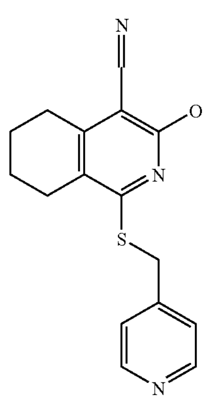 | 298 | | 100.0 |

TABLE 1-continued

| Example | Structure | MS (M + H) | ¹H NMR | Purity |
|---------|-----------|------------|--------|--------|
| 77 | 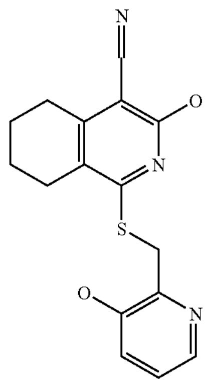 | 314 | | 100.0 |
| 78 | 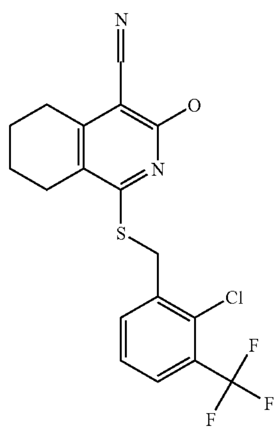 | 399 | | 100.0 |
| 79 | 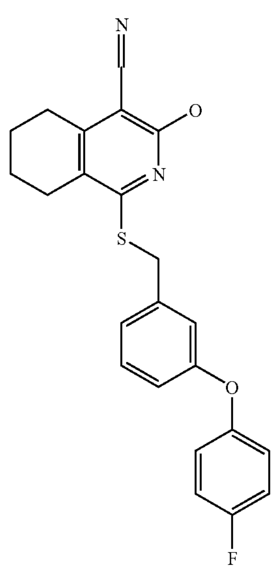 | 407 | | 100.0 |

TABLE 1-continued

| Example | Structure | MS (M + H) | ¹H NMR | Purity |
|---|---|---|---|---|
| 80 | 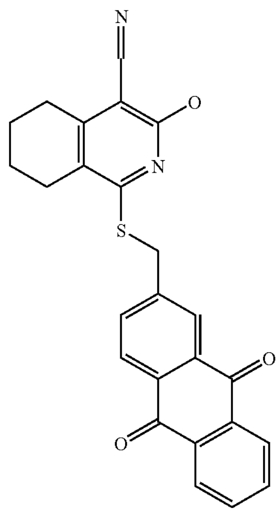 | 427 | | 100.0 |
| 81 | 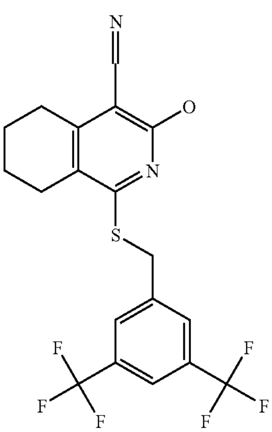 | 433 | | 100.0 |
| 82 | 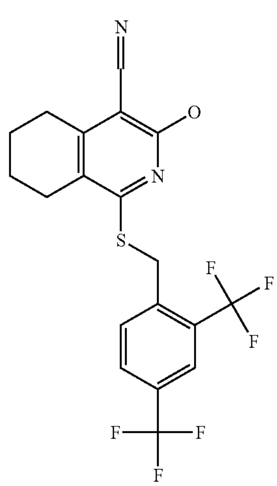 | 433 | | 95.0 |

TABLE 1-continued

| Example | Structure | MS (M + H) | ¹H NMR | Purity |
|---|---|---|---|---|
| 83 | 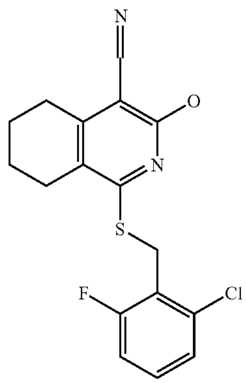 | 349 | | 100.0 |
| 84 | 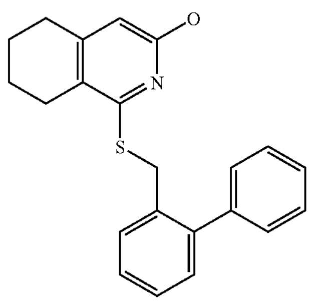 | 348 | | 100.0 |
| 85 | 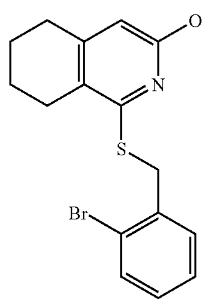 | 351 | | 100.0 |
| 86 | 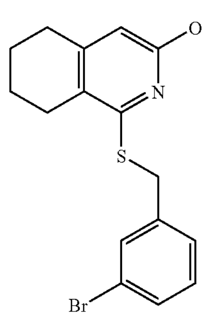 | 351 | | 100.0 |

TABLE 1-continued

| Example | Structure | MS (M + H) | ¹H NMR | Purity |
|---------|-----------|------------|--------|--------|
| 87 | 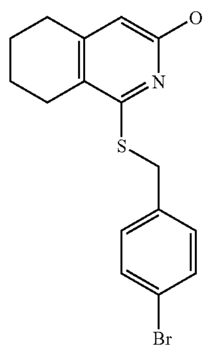 | 351 | | 100.0 |
| 88 | 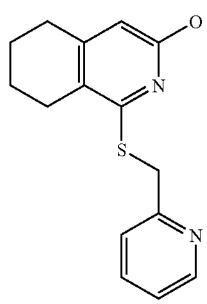 | 273 | | 97.8 |
| 89 | 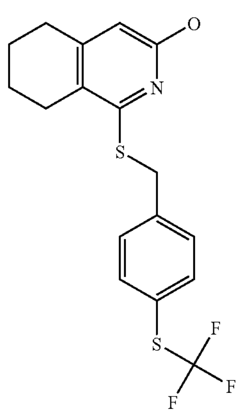 | 372 | | 100.0 |
| 90 | 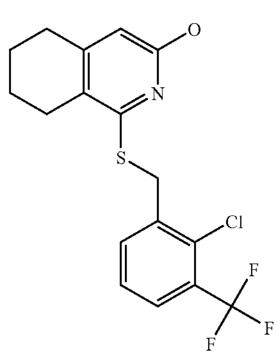 | 374 | | 100.0 |

TABLE 1-continued

| Example | Structure | MS (M + H) ¹H NMR | Purity |
|---|---|---|---|
| 91 | 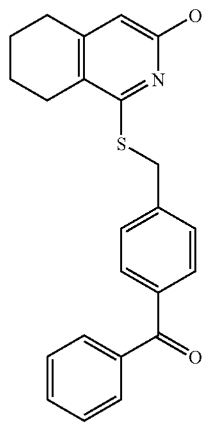 | 376 | 100.0 |
| 92 | 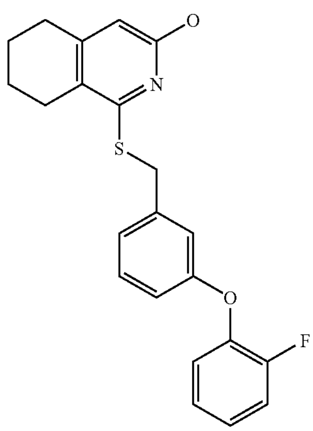 | 382 | 100.0 |
| 93 | 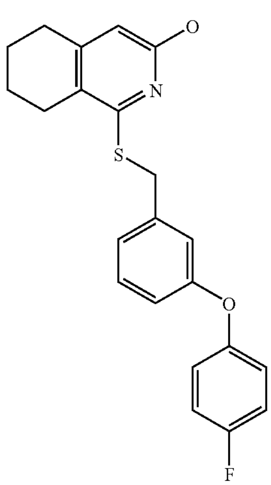 | 382 | 100.0 |

TABLE 1-continued

| Example | Structure | MS (M + H) | ¹H NMR | Purity |
|---|---|---|---|---|
| 94 | 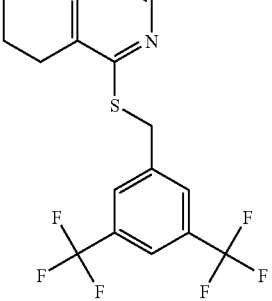 | 408 | | 100.0 |
| 95 | 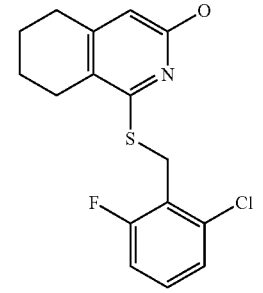 | 324 | | 100.0 |
| 96 | 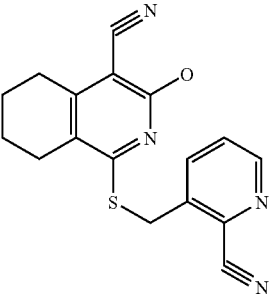 | 323 | 8.56 (d, J = 3.52 Hz, 1 H) 8.18 (d, J = 7.91 Hz, 1 H) 7.57 (dd, J = 7.91, 3.52 Hz, 1 H) 7.25 (s, 1 H) 4.66 (s, 2 H) 2.81 (s, 2 H) 2.45 (s, 2 H) 1.80 (d, J = 3.08 Hz, 4 H) | 99 |

Example 97

1-(2-Chloro-benzylsulfanyl)-6,7-dihydro-5H-[2]pyrindin-3-ol

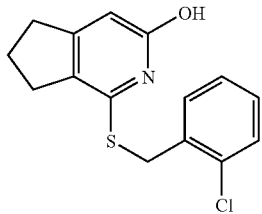

Step 1: 1-Mercapto-6,7-dihydro-5H-[2]pyrindin-3-ol

To a stirred solution of cyclopentanone (24 mmol) and malononitrile (24 mmol) in 7.5 mL of MeOH and 1.5 mL of DMF was added 5 mL carbon disulfide followed by the slow addition of 1.5 mL of Et₃N. Upon completion of addition, the resulting solution was stirred at RT for 36 h. After this time, the resulting red precipitate was collected by filtration and washed with MeOH. The red solid filter cake was taken up in 50 mL of 1N NaOH. The resulting mixture was stirred at 150° C. for 7 h and then cooled to RT. Once at the prescribed temperature, the resulting red solution was acidified with 6 N HCl. The resulting yellow precipitate was collected by filtration, washed with water and then dried in vacuum to provide the title compound as a red solid (0.35 g, 16%). LC/MS m/z 168 (M+H).

Step 2: Example 97

To a mixture of 1-mercapto-6,7-dihydro-5H-[2]pyrindin-3-ol (0.24 mmol) and K₂CO₃ (0.36 mmol) in 5 mL of EtOH was added 2-chlorobenzyl bromide (0.30 mmol). Upon completion of addition, the reaction mixture was stirred at RT for 1 h and then filtered. The filtrate was concentrated to provide a residue. The residue was purified by preparative HPLC (Gradient Solvent System: From 30% A: 70% B to 0% A: 100% B; [A=10% MeOH/90% H₂O+0.1% TFA]; [B=90% MeOH/10% H₂O+0.1% TFA]; detection at 220 nm: 10 min gradient; Phenomenex Luna AXIA 30×100 mm) to provide Example 97 as a yellow solid (15 mg, 21%). $^1$H NMR (400 MHz, CD$_3$OD) δ ppm 7.36 (d, J=7.83 Hz, 1H) 7.19-7.26 (m, 1H) 7.10-7.19 (m, 2H) 6.43 (s, 1H) 4.27 (s, 2H) 2.72-2.81 (m, 2H) 2.38 (t, J=7.33 Hz, 2H) 1.76-1.86 (m, 2H). LC/MS m/z 292 (M+H).

Example 98

4-Bromo-1-(2-chloro-benzylsulfanyl)-6,7-dihydro-5H-[2]pyrindin-3-ol

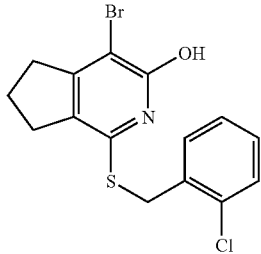

To a stirred solution of Example 97 (0.26 mmol) in 5 mL of DCM was added Br$_2$ (0.26 mmol) at RT. Upon completion of addition, the resulting solution was stirred for 1 h and then concentrated under reduced pressure to yield a residue. The residue was purified by preparative HPLC (Gradient Solvent System: From 30% A: 70% B to 0% A: 100% B; [A=10% MeOH/90% H$_2$O+0.1% TFA]; [B=90% MeOH/10% H$_2$O+ 0.1% TFA]; detection at 220 nm: 10 min gradient; Phenomenex Luna AXIA 30×100 mm) to provide Example 98 as an off-white solid (10 mg, 100%). $^1$H NMR (400 MHz, CD$_3$OD) δ ppm 7.36 (d, J=7.83 Hz, 1H) 7.23 (t, J=8.46 Hz, 1H) 7.11-7.20 (m, 2H) 4.25 (s, 2H) 2.74-2.85 (m, J=7.45, 7.45 Hz, 2H) 2.45 (s, 2H) 1.83 (s, 2H). LC/MS m/z 292 (M+H).

Example 99

1-(2-Chloro-benzylsulfanyl)-3-hydroxy-6,7-dihydro-5H-[2]pyrindine-4-carbonitrile

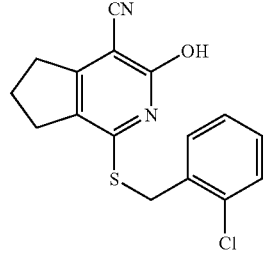

To a stirred solution of Example 98 (0.14 mmol) in 5 mL NMP was added CuCN (0.28 mmol) at RT. The reaction mixture was stirred at 150° C. for 2 h with microwave irradiation. After this time, the reaction mixture was filtered, and the filtrate was purified by preparative HPLC (Gradient Solvent System: From 30% A: 70% B to 0% A: 100% B; [A=10% MeOH/90% H$_2$O+0.1% TFA]; [B=90% MeOH/10% H$_2$O+ 0.1% TFA]; detection at 220 nm: 10 min gradient; Phenomenex Luna AXIA 30×100 mm) to provide Example 99 as an off-white solid (4 mg, 12%). $^1$H NMR (400 MHz, MeOD) 7.90 (d, J=8.34 Hz, 1H) 7.15-7.44 (m, 3H) 3.91 (s, 2H) 2.91-3.02 (m, 2H) 2.80-2.89 (m, 2H) 2.04-2.21 (m, 2H). LC/MS m/z 317 (M+H).

Examples 100 to 105

Examples 100 to 105 in Table 2 were prepared according to the procedures described in Examples 97, 98 and/or 99, or other similar methods used by one skilled in the art, utilizing other appropriate reagents. NMR spectra data are reported in δ ppm using a 400 MHz spectrometer and CD$_4$OD as the solvent.

TABLE 2

| Example | Structure | MS (M + H) | $^1$H NMR | % Purity |
|---|---|---|---|---|
| 100 | 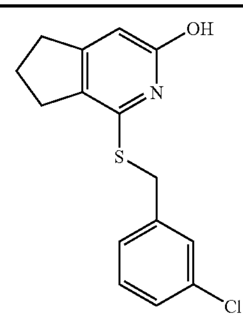 | 292 | 7.20-7.25 (m, 2 H) 7.18 (s, 1 H) 7.07-7.13 (m, 2 H) 6.40 (s, 1 H) 4.15 (s, 3 H) 2.76-2.84 (m, 2 H) 2.47 (t, J = 7.33 Hz, 2 H) 1.83-1.94 (m, 2 H) | 98 |
| 101 | 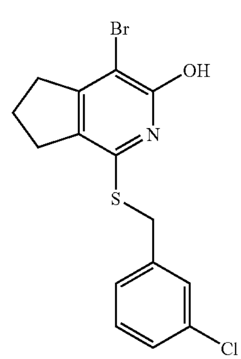 | 371 | 7.22 (d, J = 5.31 Hz, 2 H) 7.15-7.20 (m, 1 H) 7.07-7.15 (m, 1 H) 4.13 (s, 2 H) 2.82 (t, J = 7.58 Hz, 2 H) 2.50-2.60 (m, 2 H) 1.90 (s, 2 H) | 94 |

TABLE 2-continued

| Example | Structure | MS (M + H) | ¹H NMR | % Purity |
|---|---|---|---|---|
| 102 | 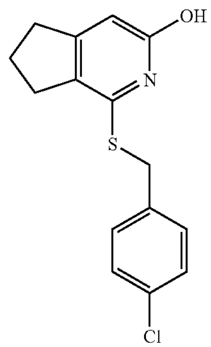 | 292 | 7.21-7.26 (m, 2 H) 7.14-7.19 (m, 2 H) 6.30 (s, 1 H) 4.14 (s, 2 H) 2.73-2.80 (m, 2 H) 2.46 (t, J = 7.33 Hz, 2 H) 1.80-1.92 (m, 2 H) | 94 |
| 103 | 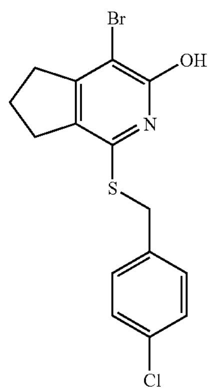 | 371 | 6.99-7.20 (m, 4 H) 4.12 (s, 2 H) 2.70 (t, J = 7.70 Hz, 2 H) 2.53 (t, J = 7.15 Hz, 2 H) 1.75-1.89 (m, 2 H) | 90 |
| 104 | 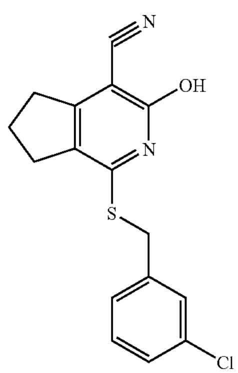 | 317 | 7.38 (s, 1 H) 7.20-7.32 (m, J = 4.95 Hz, 3 H) 4.38 (s, 1 H) 2.96 (s, 2 H) 2.09 (s, 2 H) | 98 |
| 105 | 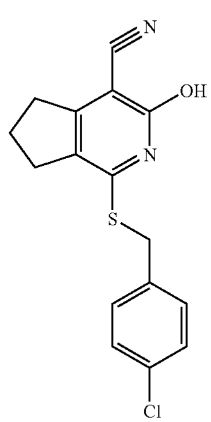 | 317 | 7.14-7.36 (m, 4 H) 4.21-4.45 (m, J = 2.75 Hz, 2 H) 2.94 (s, 2 H) 2.59-2.73 (m, J = 6.60 Hz, 2 H) 2.08 (s, 2 H) | 97 |

Example 106

4-(6-(3,3-Dimethylpiperidin-1-ylsulfonyl)pyridin-2-yl)benzonitrile

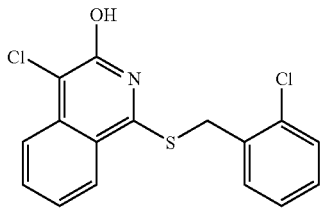

Step 1: Phenylacetyl isothiocyanate

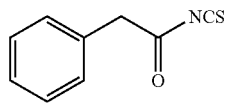

To a 250 mL round bottom flask was added phenylacetyl-chloride (15.0 g, 97.0 mmol) and toluene (70 mL) followed by lead (II) thiocyanate (25.7 g, 97.0 mmol). Upon completion of addition, the resulting suspension was stirred at 85° C. for 18 h. After this time, the resulting solids were separated by vacuum filtration, and the filtrate was concentrated by rotary evaporation to provide a residue. The residue was purified via silica gel chromatography (10% EtOAc:Hex) to yield the title compound as a pale yellow, non-viscous oil (12.2 g, 68.8 mmol, 71%). $^1$H NMR (400 MHz, CDCl$_3$): δ ppm 7.41-7.30 (m, 3H), 7.29-7.23 (m, 2H), 3.85 (s, 2H).

Step 2: 1-Thioxo-1,4-dihydro-2H-isoquinolin-3-one

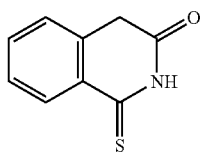

To a 250 mL round bottom flask was added anhydrous aluminum chloride powder (21.6 g, 162.2 mmol) and 1,1,2,2-tetrachloroethane (20 mL). The resulting solution was cooled to 0° C. under Ar and then a solution of phenylacetyl isothiocyanate (12.5 g, 70.5 mmol) in 1,1,2,2-tetrachloroethane (10 mL) was added dropwise via addition funnel over a period of 10 min. Upon completion of addition, the reaction mixture was stirred at 95° C. for 1 h during which time the slurry became a dark brown solution. The reaction mixture was then allowed to cool to RT. Once at the prescribed temperature, the reaction mixture was carefully quenched with a solution of cold HCl (250 mL, 2.4 N). The resultant beige precipitate was collected by vacuum filtration, air dried for 0.5 h and then recrystallized from glacial AcOH and decolorizing charcoal to yield the title compound as an orange crystalline solid (7.2 g, 40.6 mmol, 58%). $^1$H NMR (400 MHz, CDCl$_3$): δ ppm 3.29 (s, 1H), 11.78 (s, 1H), 8.57 (d, 1H, J=8.35 Hz), 7.59-LC/MS m/z [M+H].

Step 3: 1-(2-Chlorobenzylsulfanyl)isoquinolin-3-ol

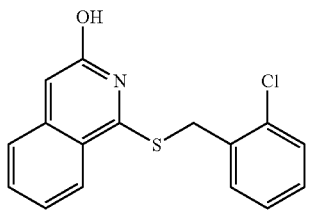

To a 50 mL round bottom flask was added 1-thioxo-1,4-dihydro-2H-isoquinolin-3-one (0.8 g, 4.51 mmol), K$_2$CO$_3$ (1.9 g, 13.5 mmol), and absolute EtOH (15 mL) followed by 1-(bromomethyl)-2-chlorobenzene (0.88 g, 4.29 mmol). Upon completion of addition, the reaction mixture was stirred for 18 h. At the conclusion of this period, the reaction mixture was acidified with a solution of citric acid (100 mL, 10% w/v), extracted with EtOAc (100 mL), washed with brine (75 mL) and then dried over Na$_2$SO$_4$. The solvent was removed under vacuum to yield a residue. The residue was purified via silica gel chromatography (20% EtOAc:Hex) to yield the title compound as a pale yellow solid (1.1 g, 3.64 mmol, 81%). $^1$H NMR (400 MHz, DMSO-d$_6$): δ ppm 8.05 (d, J=8.35 Hz, 1H), 7.59-7.64 (m, 1H), 7.50-7.57 (m, 2H), 7.37-7.42 (m, 1H), 7.31 (ddd, J=8.46, 6.92, 1.32 Hz, 1H), 7.16-7.23 (m, 2H), 6.71 (s, 1H), 5.92 (br. s., 1H), 4.67 (s, 2H). LC/MS m/z 302 [M+H].

Step 4: Example 106

To a solution of 1-(2-chlorobenzylsulfanyl)isoquinolin-3-ol (0.5 g, 1.66 mmol) in DCM (20 mL) was added N-chlorosuccinimide (0.24 g, 1.82 mmol). The reaction mixture was stirred at 40° C. for 18 h. After this time, the solvent was removed under vacuum to yield a residue. The residue was purified via silica gel chromatography (30% EtOAc:Hex) to provide Example 106 as a pale yellow solid (0.3 g, 0.89 mmol, 54%). $^1$H NMR (400 MHz, CDCl$_3$): δ ppm 8.08 (d, J=8.79 Hz, 1H), 8.03 (d, J=8.79 Hz, 1H), 7.70 (ddd, J=8.35, 7.03, 1.32 Hz, 1H), 7.55-7.60 (m, 1H), 7.37-7.44 (m, 2H), 7.17-7.24 (m, 2H), 6.28 (br. s., 1H), 4.68 (s, 2H). LC/MS m/z 337 [M+H].

Example 107

4-Chloro-1-(2-chlorobenzylsulfonyl)isoquinolin-3-ol

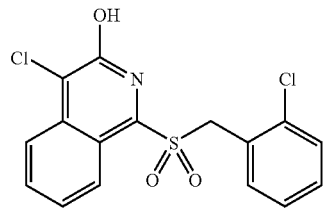

A mixture of Example 106 (90 mg, 0.268 mmol) and MCPBA (102 mg, 0.589 mmol) in DCM (20 mL) was stirred for 18 h. After this time, the solvent was removed under vacuum to yield a residue. The residue was purified by preparative HPLC (Gradient Solvent System: From 50% A: 50% B to 0% A: 100% B; [A=10% MeOH/90% H$_2$O+0.1% TFA]; [B=90% MeOH/10% H$_2$O+0.1% TFA]; detection at 220 nm: 10 min gradient; Phenomenex Luna AXIA 30×100 mm) to provide Example 107 as a yellow solid (11.3 mg, 0.0307 mmol, 11%). $^1$H NMR (400 MHz, CDCl$_3$): δ ppm 8.75 (d, J=8.79 Hz, 1H), 8.20 (d, J=8.79 Hz, 1H), 7.78 (dd, J=8.35, 7.03 Hz, 1H), 7.57-7.63 (m, 1H), 7.48 (ddd, J=8.35, 7.25, 1.10 Hz, 1H), 7.24-7.36 (m, 3H), 5.02 (s, 2H). LC/MS m/z 369 [M+H].

Example 108

4-Bromo-1-(2-chlorobenzylthio)isoquinolin-3-ol

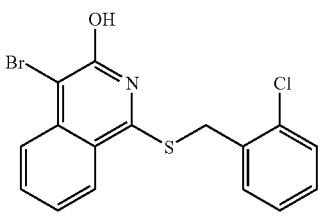

To a 50 mL round bottom flask containing 1-(2-chlorobenzylsulfanyl)isoquinolin-3-ol (0.330 g, 1.09 mmol), was added glacial AcOH (5 mL), followed by the dropwise addition of bromine (0.192 g, 1.20 mmol) in a solution of carbon tetrachloride (15 mL). Upon completion of addition, the reaction mixture was stirred for 2 h. At the conclusion of this period, the reaction mixture was neutralized with NaHCO$_3$ (100 mL, sat. aq.) and then extracted with EtOAc (100 mL). The organic layer was separated, washed with brine (75 mL) and then dried over Na$_2$SO$_4$. The solvent was removed under vacuum to yield a residue. The residue was purified by silica gel chromatography (20% EtOAc:Hex) to provide Example 108 as a pale yellow solid (0.296 g, 0.777 mmol, 71%). $^1$H NMR (400 MHz, CDCl$_3$): δ ppm 8.07 (d, J=8.35 Hz, 1H), 8.01 (d, J=8.35 Hz, 1H), 7.69 (ddd, J=8.35, 7.03, 1.32 Hz, 1H), 7.55-7.60 (m, 1H), 7.36-7.44 (m, 2H), 7.17-7.24 (m, 2H), 6.31 (s, 1H), 4.67 (s, 2H). LC/MS m/z 381 [M+H].

Example 109

4,7-Dichloro-1-(2-chlorobenzylthio)isoquinolin-3-ol

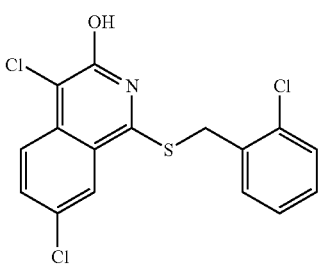

Step 1: (4-Chlorophenyl)acetyl isothiocyanate

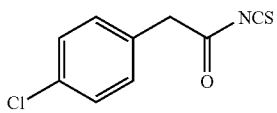

The title compound was prepared in a similar manner as described in Step 1, Example 106, utilizing the appropriate reagents. The pale yellow, non-viscous oil was carried onto subsequent steps without characterization.

Step 2: 7-Chloro-1-mercaptoisoquinolin-3-ol

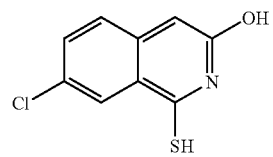

The title compound was prepared in a similar manner as described in Step 2, Example 106, utilizing (4-chlorophenyl)acetyl isothiocyanate and the other appropriate reagents to yield a brick red powder. LC/MS m/z 212 [M+H].

Step 3: 7-Chloro-1-(2-chlorobenzylsulfanyl)isoquinolin-3-ol

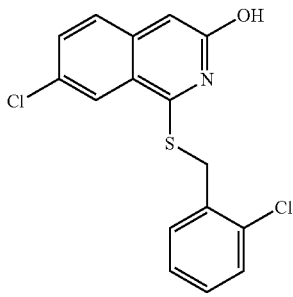

The title compound was prepared in a similar manner as described in Step 3, Example 106, utilizing 7-Chloro-1-mercaptoisoquinolin-3-ol and the other appropriate reagents to yield a tan solid. $^1$H NMR (400 MHz, CDCl$_3$): δ ppm 8.04 (d, J=1.76 Hz, 1H), 7.50-7.60 (m, 2H), 7.45-7.49 (m, 1H), 7.38-7.42 (m, 1H), 7.18-7.23 (m, 2H), 6.69 (s, 1H), 5.96 (br. s., 1H), 4.66 (s, 2H). LC/MS m/z 337 [M+H].

Step 4: Example 109

Example 109 was prepared in a similar manner similar as described in Step 4, Example 106, utilizing 7-chloro-1-(2-chlorobenzylsulfanyl)isoquinolin-3-ol and the other appropriate reagents to yield an off-white solid. $^1$H NMR (400 MHz, CDCl$_3$): δ ppm 8.06 (d, J=2.20 Hz, 1H), 7.97 (d, J=8.79 Hz, 1H), 7.62 (dd, J=9.01, 1.98 Hz, 1H), 7.51-7.59 (m, 1H), 7.35-7.44 (m, 1H), 7.18-7.24 (m, 2H), 6.30 (s, 1H), 4.66 (s, 2H). LC/MS m/z 371 [M+H].

Examples 110 to 139

Examples 110 to 139 in Table 3 were prepared in a similar manner as described in Examples 106 to 109 or other similar methods used by one skilled in the art, utilizing other appropriate reagents. NMR spectra data are reported in δ ppm using a 400 MHz spectrometer and $CD_4OD$ as the solvent. In the structures set forth in Table 3, the "—O" attached to the carbon adjacent to the nitrogen in the bicyclic core is used to denote an "—OH" group as indicated in Formula I.

TABLE 3

| Example | Structure | MS [M + H] | ¹H NMR | Purity |
|---|---|---|---|---|
| 110 | 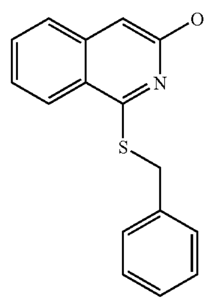 | 268.4 | 8.06 (d, J = 8.79 Hz, 1 H), 7.59-7.68 (m, 1 H), 7.54 (td, J = 7.47, 0.88 Hz, 1 H), 7.44 (d, J = 7.03 Hz, 2 H), 7.23-7.35 (m, 4 H), 6.72 (s, 1 H), 6.01 (br. s., 1 H), 4.56 (s, 2 H) | 99 |
| 111 | 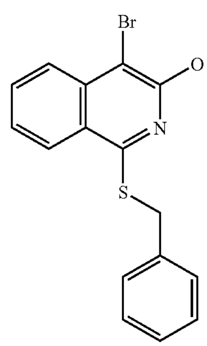 | 347.3 | 8.08 (d, J = 8.35 Hz, 1 H), 8.01 (d, J = 8.79 Hz, 1 H), 7.70 (ddd, J = 8.46, 7.14, 1.10 Hz, 1 H), 7.45 (d, J = 7.47 Hz, 2 H), 7.40 (ddd, J = 8.24, 6.92, 1.10 Hz, 1 H), 7.33 (t, J = 7.25 Hz, 2 H), 7.23-7.29 (m, 1 H), 6.28 (br. s., 1 H), 4.56 (s, 2 HH) | 99 |
| 112 | 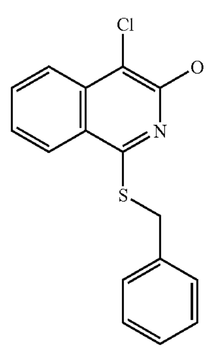 | 302.8 | 8.04 (d, J = 8.35 Hz, 1 H), 7.71 (ddd, J = 8.35, 7.03, 1.32 Hz, 1 H), 7.43-7.48 (m, 2 H), 7.37-7.43 (m, 1 H), 7.30-7.36 (m, 2 H), 7.24-7.29 (m, 1 H), 6.24 (br. s., 1 H), 4.56 (s, 2 H) | 99 |
| 113 | 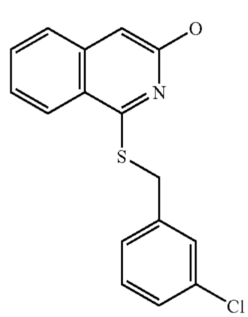 | 302.8 | 8.04 (d, J = 8.35 Hz, 1 H), 7.58-7.68 (m, 1 H), 7.54 (t, J = 7.47 Hz, 1 H), 7.42 (s, 1 H), 7.26-7.36 (m, 2 H), 7.16-7.27 (m, 2 H), 6.74 (s, 1 H), 6.28 (br. s., 1 H), 4.50 (s, 2 H) | 99 |

TABLE 3-continued

| Example | Structure | MS [M + H] | ¹H NMR | Purity |
|---|---|---|---|---|
| 114 | 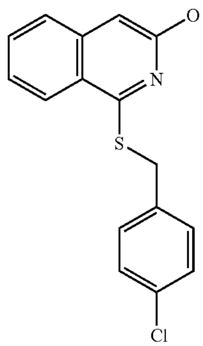 | 302.8 | 8.04 (d, J = 8.35 Hz, 1 H), 7.60-7.66 (m, 1 H), 7.52-7.58 (m, 1 H), 7.33-7.38 (m, 2 H), 7.31 (ddd, J = 8.35, 6.81, 1.10 Hz, 1 H), 7.24-7.28 (m, 2 H), 6.73 (s, 1 H), 6.19 (br s., 1 H), 4.50 (s, 2 H) | 99 |
| 115 | 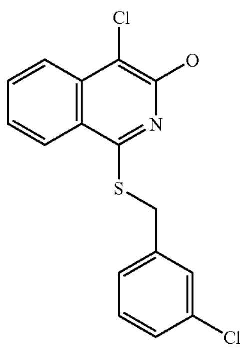 | 337.2 | 8.08 (d, J = 8.79 Hz, 1 H), 8.04 (d, J = 8.35 Hz, 1 H), 7.72 (ddd, J = 8.35, 7.03, 1.32 Hz, 1 H), 7.46 (s, 1 H), 7.42 (ddd, J = 8.35, 7.03, 1.32 Hz, 1 H), 7.32-7.36 (m, 1 H), 7.22-7.26 (m, 2 H), 6.20 (br. s., 1 H), 4.53 (s, 2 H) | 99 |
| 116 | 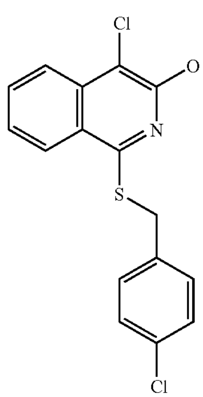 | 337.2 | 8.07 (d, J = 8.35 Hz, 1 H), 8.04 (d, J = 8.35 Hz, 1 H), 7.72 (ddd, J = 8.35, 7.03, 1.32 Hz, 1 H), 7.41-7.45 (m, 1 H), 7.39 (d, J = 8.79 Hz, 2 H), 7.28 (d, J = 8.35 Hz, 2 H), 6.23 (br s, 1 H), 4.52 (s, 2 H) | 99 |
| 117 | 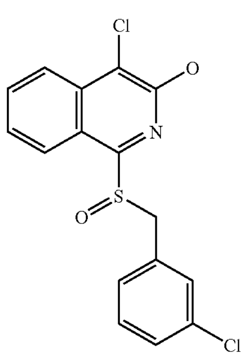 | 353.2 | 8.17 (dd, J = 10.33, 9.45 Hz, 2 H), 7.69-7.80 (m, 1 H), 7.39 (ddd, J = 8.35, 7.03, 0.88 Hz, 1 H), 7.15-7.21 (m, 1 H), 7.10 (t, J = 7.69 Hz, 1 H), 7.02 (s, 1 H), 6.92 (d, J = 7.47 Hz, 1 H), 4.30-4.45 (m, 2 H) | 99 |

TABLE 3-continued

| Example | Structure | MS [M + H] | ¹H NMR | Purity |
|---|---|---|---|---|
| 118 | 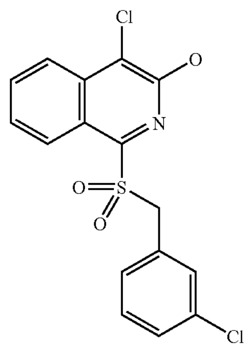 | 369.2 | 8.83 (d, J = 8.79 Hz, 1 H), 8.19 (d, J = 8.79 Hz, 1 H), 7.81 (t, J = 7.69 Hz, 1 H), 7.52-7.59 (m, 1 H), 7.40 (s, 1 H), 7.20-7.32 (m, 3 H), 6.77 (br s, 1 H), 4.83 (s, 2 H) | 99 |
| 119 | 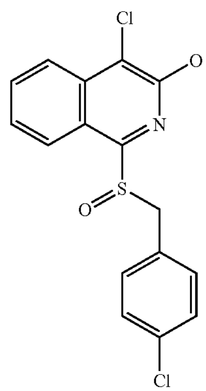 | 353.2 | 8.17 (dd, J = 11.27, 8.52 Hz, 2 H), 7.69-7.80 (m, 1 H), 7.34-7.43 (m, 1 H), 7.15 (d, J = 8.24 Hz, 2 H), 6.97 (d, J = 8.24 Hz, 2 H), 4.38 (s, 2 H) | 97 |
| 120 | 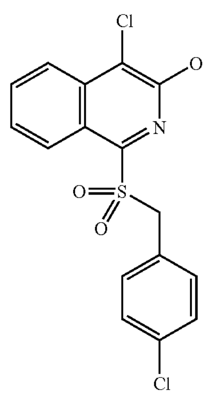 | 369.2 | 8.83 (d, J = 8.79 Hz, 1 H), 8.19 (d, J = 8.79 Hz, 1 H), 7.72-7.90 (m, 1 H), 7.48-7.61 (m, 1 H), 7.27-7.35 (m, 4 H), 6.68 (br. s., 1 H), 4.84 (s, 2 H) | 99 |
| 121 | 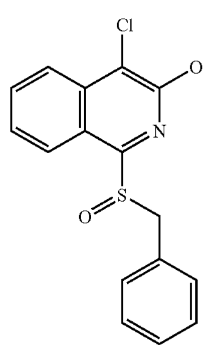 | 318.8 | 8.13 (d, J = 8.79 Hz, 1 H), 8.08 (d, J = 8.35 Hz, 1 H), 7.66-7.76 (m, 1 H), 7.29-7.36 (m, 1 H), 7.12-7.23 (m, 3 H), 7.01 (d, J = 6.59 Hz, 2 H), 4.34-4.52 (m, 2 H) | 98 |

TABLE 3-continued

| Example | Structure | MS [M + H] | ¹H NMR | Purity |
|---|---|---|---|---|
| 122 | 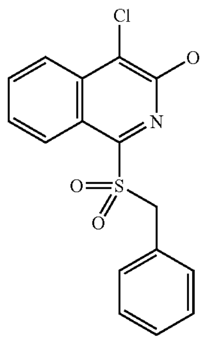 | 334.8 | 8.82 (d, J = 8.79 Hz, 1 H), 8.18 (d, J = 8.35 Hz, 1 H), 7.78 (ddd, J = 8.57, 7.03, 1.10 Hz, 1 H), 7.51 (ddd, J = 8.79, 6.81, 1.10 Hz, 1 H), 7.27-7.37 (m, 5 H), 6.89 (br. s., 1 H), 4.84 (s, 2 H) | 99 |
| 123 | 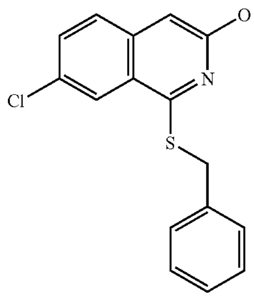 | 302.8 | 8.04 (d, J = 1.76 Hz, 1 H), 7.54-7.61 (m, 1 H), 7.42-7.49 (m, 3 H), 7.24-7.35 (m, 3 H), 6.70 (s, 1 H), 5.88 (br. s., 1 H), 4.55 (s, 2 H) | 99 |
| 124 | 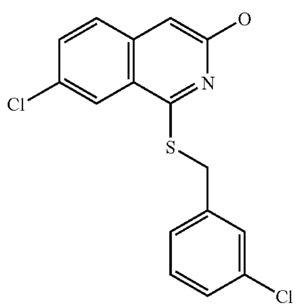 | 337.2 | 8.03 (d, J = 1.76 Hz, 1 H), 7.55-7.61 (m, 1 H), 7.46-7.52 (m, 1 H), 7.43 (s, 1 H), 7.28-7.34 (m, 1 H), 7.22-7.28 (m, 2 H), 6.71 (s, 1 H), 5.88 (br s, 1 H), 4.51 (s, 2 H) | 99 |
| 125 | 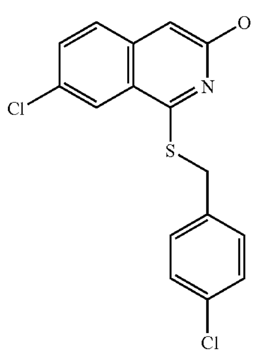 | 337.2 | 8.03 (d, J = 1.76 Hz, 1 H), 7.55-7.61 (m, 1 H), 7.46-7.51 (m, 1 H), 7.34-7.39 (m, 2 H), 7.26-7.30 (m, 2 H), 6.70 (s, 1 H), 5.81 (br. s., 1 H), 4.51 (s, 2 H) | 99 |

TABLE 3-continued

| Example | Structure | MS [M + H] | ¹H NMR | Purity |
|---|---|---|---|---|
| 126 | 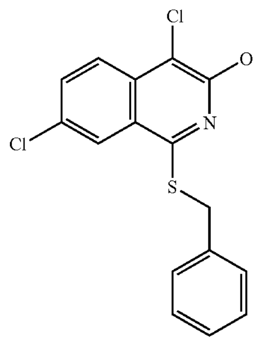 | 337.2 | 8.07 (d, J = 2.20 Hz, 1 H), 7.98 (d, J = 9.23 Hz, 1 H), 7.63 (dd, J = 9.01, 1.98 Hz, 1 H), 7.44 (d, J = 7.47 Hz, 2 H), 7.27-7.36 (m, 3 H), 6.24 (br. s., 1 H), 4.55 (s, 2 H) | 99 |
| 127 | 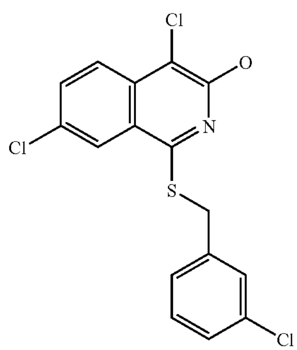 | 371.7 | 8.06 (d, J = 1.76 Hz, 1 H), 7.99 (d, J = 9.23 Hz, 1 H), 7.64 (dd, J = 9.01, 1.98 Hz, 1 H), 7.44 (s, 1 H), 7.31-7.35 (m, 1 H), 7.24-7.27 (m, 2 H), 6.22 (s, 1 H), 4.52 (s, 2 H) | 99 |
| 128 | 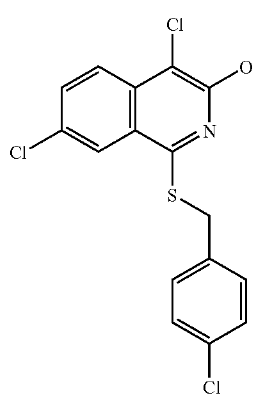 | 371.7 | 8.06 (d, J = 1.65 Hz, 1 H), 7.98 (d, J = 9.34 Hz, 1 H), 7.64 (dd, J = 9.07, 1.92 Hz, 1 H), 7.38 (d, J = 8.25 Hz, 2 H), 7.28 (d, J = 8.25 Hz, 2 H), 6.21 (br s, 1 H), 4.51 (s, 2 H) | 99 |
| 129 | 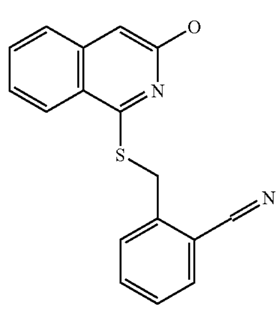 | 293.4 | 7.97 (d, J = 8.35 Hz, 1 H), 7.58-7.70 (m, 3 H), 7.50-7.58 (m, 2 H), 7.31 (q, J = 7.18 Hz, 2 H), 6.92 (br. s., 1 H), 6.70 (s, 1 H), 4.73 (s, 2 H) | 99 |

TABLE 3-continued

| Example | Structure | MS [M + H] | ¹H NMR | Purity |
|---|---|---|---|---|
| 130 | 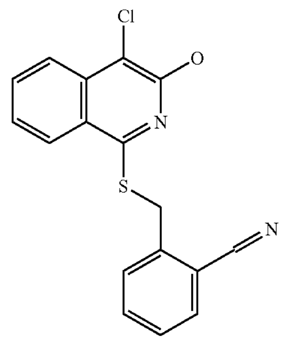 | 327.8 | 8.02 (dd, J = 12.74, 8.35 Hz, 2 H), 7.60-7.72 (m, 3 H), 7.52-7.59 (m, 1 H), 7.36-7.43 (m, 1 H), 7.29-7.35 (m, 1 H), 4.72 (s, 2 H) | 99 |
| 131 | 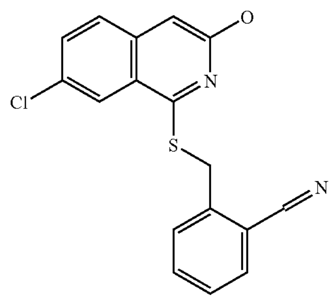 | 327.8 | 7.95 (d, J = 2.20 Hz, 1 H), 7.64-7.68 (m, 1 H), 7.62 (dd, J = 7.91, 0.88 Hz, 1 H), 7.57 (td, J = 7.69, 1.32 Hz, 1 H), 7.55 (d, J = 8.79 Hz, 1 H), 7.42-7.48 (m, 1 H), 7.33 (td, J = 7.58, 1.10 Hz, 1 H), 7.04 (s, 1 H), 6.68 (s, 1 H), 4.72 (s, 2 H) | 99 |
| 132 | 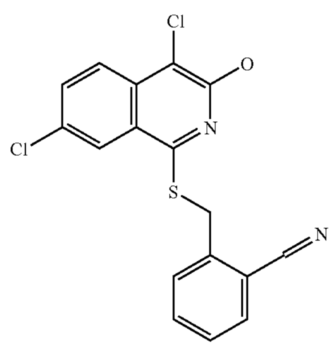 | 362.3 | 7.99 (d, J = 4.83 Hz, 1 H), 7.97 (d, J = 1.76 Hz, 1 H), 7.60-7.69 (m, 2 H), 7.54-7.60 (m, 2 H), 7.51 (br. s., 1 H), 7.34 (t, J = 7.47 Hz, 1 H), 4.71 (s, 2 H) | 99 |
| 133 | 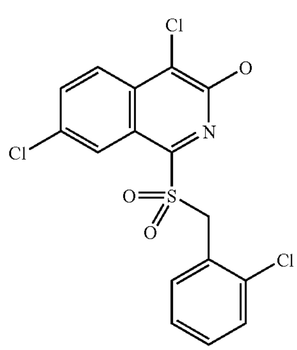 | 403.7 | 8.61 (s, 1 H), 8.12 (d, J = 8.79 Hz, 1 H), 7.66 (d, J = 8.35 Hz, 1 H), 7.61 (d, J = 7.03 Hz, 1 H), 7.19-7.36 (m, 3 H), 4.94 (s, 2 H) | 98 |

TABLE 3-continued

| Example | Structure | MS [M + H] | ¹H NMR | Purity |
|---|---|---|---|---|
| 134 | 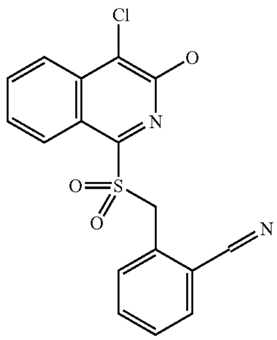 | 359.8 | δ 8.82 (d, J = 8.35 Hz, 1 H), 8.21 (d, J = 8.79 Hz, 1 H), 8.02 (br. s., 1 H), 7.93 (d, J = 7.91 Hz, 1 H), 7.75-7.82 (m, 1 H), 7.63-7.73 (m, 2 H), 7.53-7.59 (m, 1 H), 7.43-7.51 (m, 1 H), 5.22 (s, 2 H) | 99 |
| 135 | 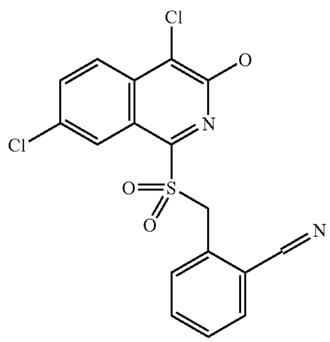 | 394.3 | 8.79 (d, J = 1.76 Hz, 1 H), 8.15 (d, J = 9.23 Hz, 1 H), 7.93 (d, J = 8.35 Hz, 1 H), 7.65-7.73 (m, 3 H), 7.47 (t, J = 7.69 Hz, 1 H), 5.20 (s, 2 H) | 99 |
| 136 | 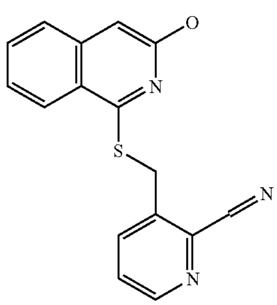 | 294 | (DMSO-d₆) 10.71 (s, 1 H), 8.55 (dd, J = 4.61, 1.54 Hz, 1 H), 8.28 (dd, J = 7.91, 0.88 Hz, 1 H), 7.85 (d, J = 8.79 Hz, 1 H), 7.65 (d, J = 8.35 Hz, 1 H), 7.61 (dd, J = 8.13, 4.61 Hz, 1 H), 7.53 (t, J = 7.47 Hz, 1 H), 7.27 (t, J = 7.69 Hz, 1 H), 6.65 (s, 1 H), 4.70 (s, 2 H) | 98 |
| 137 | 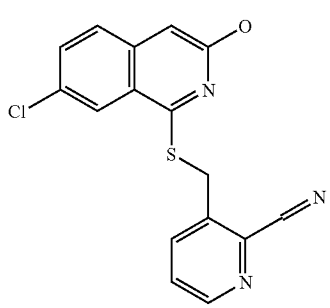 | 328 | (DMSO-d₆) 10.93 (s, 1 H), 8.62 (dd, J = 4.83, 1.32 Hz, 1 H), 8.30 (dd, J = 8.35, 1.32 Hz, 1 H), 7.88 (d, J = 1.76 Hz, 1 H), 7.78 (d, J = 8.79 Hz, 1 H), 7.66 (dd, J = 7.91, 4.83 Hz, 1 H), 7.61 (dd, J = 9.01, 1.98 Hz, 1 H), 6.75 (s, 1 H), 4.76 (s, 2 H) | 99 |

TABLE 3-continued

| Example | Structure | MS [M + H] | ¹H NMR | Purity |
|---|---|---|---|---|
| 138 | 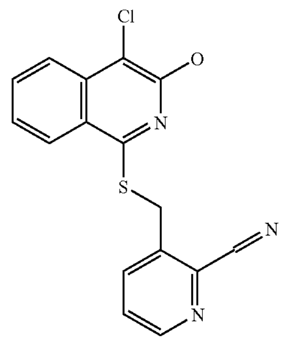 | 328 | (DMSO-d$_6$) 11.64 (s, 1 H), 8.62 (dd, J = 4.95, 1.65 Hz, 1 H), 8.35 (dd, J = 7.97, 1.37 Hz, 1 H), 8.02 (d, J = 8.24 Hz, 1 H), 7.96 (d, J = 8.79 Hz, 1 H), 7.76-7.85 (m, 1 H), 7.67 (dd, J = 7.97, 4.67 Hz, 1 H), 7.43-7.50 (m, 1 H), 4.79 (s, 2 H) | 99 |
| 139 | 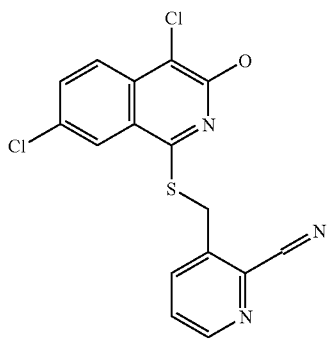 | 363 | (DMSO-d$_6$) 11.82 (br. s., 1 H), 8.57 (dd, J = 4.67, 1.37 Hz, 1 H), 8.27 (dd, J = 7.97, 1.37 Hz, 1 H), 7.89-7.94 (m, 2 H), 7.74 (dd, J = 9.07, 1.92 Hz, 1 H), 7.61 (dd, J = 7.97, 4.67 Hz, 1 H), 4.74 (s, 2 H) | 99 |

Example 140

1-(2-Chlorobenzylthio)-4-nitroisoquinolin-3-ol

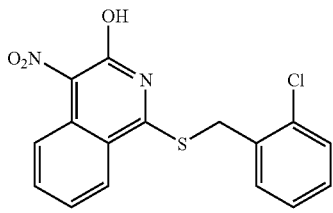

To an ice cooled solution of Et$_2$O (10 mL) was slowly added nitric acid (1 mL, 90% v/v aq.). Upon completion of addition, a solution of 1-(2-chlorobenzylsulfanyl)isoquinolin-3-ol (0.120 g, 0.398 mmol) in Et$_2$O (2 mL) was added in one portion. The reaction mixture was warmed to RT over a period of 1 h, during which time the colored changed from a pale yellow to an amber color. Once at the prescribed temperature, the reaction mixture was diluted with water (100 mL), extracted with Et$_2$O (75 mL), washed with brine (75 mL) and dried over Na$_2$SO$_4$ to provide Example 140 as a bright yellow solid (5.95 mg, 0.0172 mmol, 4%). ¹H NMR (400 MHz, CDCl$_3$): δ ppm 13.61 (s, 1H), 9.03 (d, J=8.79 Hz, 1H), 8.24 (dd, J=8.35, 0.88 Hz, 1H), 7.88 (ddd, J=8.68, 7.14, 1.32 Hz, 1H), 7.72 (dd, J=5.93, 3.73 Hz, 1H), 7.51 (ddd, J=8.24, 7.14, 0.88 Hz, 1H), 7.38-7.45 (m, 1H), 7.22-7.27 (m, 2H), 4.82 (s, 2H). LC/MS m/z 347 [M+H].

Example 141

1-(2-Chlorobenzylthio)-3-hydroxyisoquinoline-4-carbonitrile

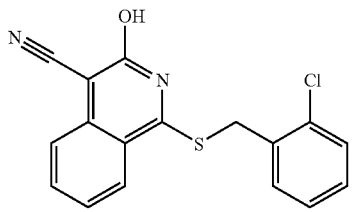

Step 1: 3-Hydroxy-2-oxy-isoquinoline-4-carbonitrile

To a 250 mL round bottom flask was added 2-bromobenzaldehyde oxime (2.50 g, 12.5 mmol), ethylcyanoacetate (1.41 g, 12.5 mmol), CuBr (179 mg, 1.25 mmol), and toluene (30 mL) followed by the portion-wise addition of NaH (1.20 g, 60% dispersion in mineral oil, 30 mmol). Upon completion of addition, the resulting slurry was stirred at 80° C. for 4 h under Ar, during which time an additional amount of toluene (20 mL) was added to facilitate stirring. At the conclusion of this period, the reaction mixture was cooled to RT and then diluted with HCl (250 mL, 1N aq.). The resulting solids were collected by vacuum filtration to provide crude product. The crude product was purified via recrystallization from EtOH to yield the title compound as a beige solid (1.2 g, 6.41 mmol, 51%). ¹H NMR (400 MHz, CDCl₃): δ ppm 9.60 (s, 1H), 7.89 (d, J=8.35 Hz, 1H), 7.74 (t, J=7.69 Hz, 1H), 7.54 (d, J=9.23 Hz, 1H), 7.27 (t, J=7.47 Hz, 1H). LC/MS m/z 187 [M+H].

Step 2: Example 141

A suspension of 3-hydroxy-2-oxy-isoquinoline-4-carbonitrile (300 mg, 1.61 mmol) in dry MeCN (10 mL) was stirred at 80° C. under Ar and acetic anhydride (986 mg, 9.66 mmol) followed by (2-chlorophenyl)-methanethiol (307 mg, 1.93 mmol) were added. Upon completion of addition, the reaction mixture was stirred at 80° C. for 2 h under Ar. At the conclusion of this period, the reaction mixture was poured into a suspension of K₂CO₃ (5 g) in MeOH (50 mL), and the resulting mixture was stirred for 1 h and then neutralized with a solution of citric acid (250 mL, 10% w/v aq.). The aqueous phase was extracted with EtOAc and the organic layer was washed with brine. The combined organics were dried over Na₂SO₄. and then the solvent was removed to yield a residue. The residue was purified by preparative HPLC (Gradient Solvent System: From 50% A: 50% B to 0% A: 100% B; [A=10% MeOH/90% H₂O+0.1% TFA]; [B=90% MeOH/10% H₂O+0.1% TFA]; detection at 220 nm: 10 min gradient; Phenomenex Luna AXIA 30×100 mm) to provide Example 141 as a tan solid (18 mg, 0.055 mmol, 3%). ¹H NMR (400 MHz, CDCl₃): δ ppm 12.82 (br. s., 1H), 8.08 (d, J=8.35 Hz, 1H), 7.74-7.90 (m, 3H), 7.45-7.54 (m, 2H), 7.26-7.37 (m, 2H), 4.75 (s, 2H). LC/MS m/z 327 [M+H].

Example 142

4-Chloro-1-(2-phenylpropan-2-ylthio)isoquinolin-3-ol

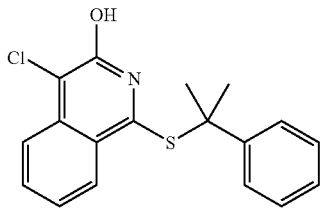

Step 1: 1-(2-Phenylpropan-2-ylthio)isoquinolin-3-ol

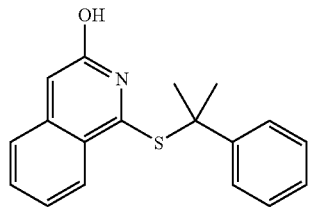

To a 50 mL round bottom flask was added 1-thioxo-1,4-dihydro-2H-isoquinolin-3-one (250 mg, 1.41 mmol), and 2-phenylpropan-2-thiol (192 mg, 1.41) followed by a solution of TFA (10 mL, 20% v/v in DCM). The reaction mixture was stirred under Ar for 1 h, neutralized with NaHCO₃ (100 mL, sat. aq.), and then extracted with EtOAc. The organic phase was washed with brine, dried over Na₂SO₄, and then the solvent was removed by rotary evaporation to yield a crude residue. The crude residue was purified via silica gel chromatography to provide the title compound as an orange solid (188 mg, 0.636 mmol, 45%). ¹H NMR (400 MHz, CDCl₃): δ ppm 8.11 (d, J=8.79 Hz, 1H), 7.55 (t, J=7.47 Hz, 3H), 7.42-7.50 (m, 1H), 7.14-7.29 (m, 5H), 6.74 (s, 1H), 1.95 (s, 6H). LC/MS m/z 296 [M+H].

Step 2: Example 142

Example 142 was synthesized in a similar manner as described in Step 4, Example 106, utilizing 1-(1-methyl-1-phenylethylsulfanyl)isoquinolin-3-ol and the N-chlorosuccinimide. ¹H NMR (400 MHz, CDCl₃): δ ppm 8.13 (d, J=8.35 Hz, 1H), 7.97 (d, J=8.79 Hz, 1H), 7.63 (d, J=7.91 Hz, 1H), 7.59 (d, J=7.47 Hz, 2H), 7.25-7.35 (m, 3H), 7.16-7.24 (m, 1H), 1.98 (s, 6H). LC/MS m/z 371 [M+H].

Examples 143 to 214

Examples 143 to 214 in Table 4 were prepared in a similar manner as described in Example 141 or other similar methods used by one skilled in the art, utilizing other appropriate reagents. NMR spectra data are reported in δ ppm using a 400 MHz spectrometer and CD₄OD as the solvent. In the structures set forth in Table 4, the "—O" attached to the carbon adjacent to the nitrogen in the bicyclic core is used to denote an "—OH" group as indicated in Formula I.

TABLE 4

| Example | Structure | MS [M + H] | ¹H NMR | Purity |
| --- | --- | --- | --- | --- |
| 143 | 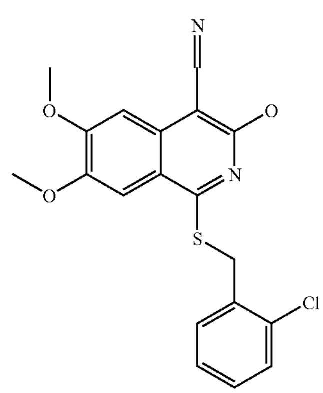 | 388 | 12.31 (s, 1 H), 7.75 (dd, J = 6.59, 2.64 Hz, 1 H), 7.38-7.50 (m, 1 H), 7.18-7.34 (m, 2 H), 7.11 (s, 1 H), 6.97 (s, 1 H), 4.68 (s, 2 H), 3.90 (s, 3 H), 3.80 (s, 3 H) | 98 |

TABLE 4-continued

| Example | Structure | MS [M + H] | ¹H NMR | Purity |
|---|---|---|---|---|
| 144 | 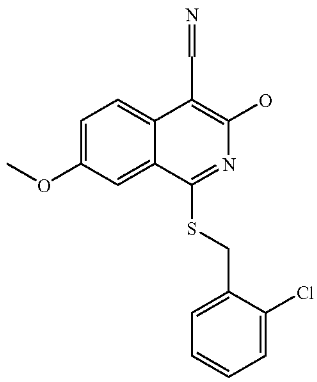 | 358 | 12.52 (br. s., 1 H), 7.82 (dd, J = 6.81, 2.42 Hz, 1 H), 7.74 (d, J = 9.23 Hz, 1 H), 7.45-7.58 (m, 2 H), 7.27-7.39 (m, 2 H), 7.25 (d, J = 2.64 Hz, 1 H), 4.76 (s, 2 H), 3.85 (s, 3 H) | 99 |
| 145 | 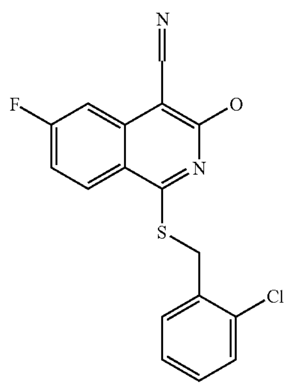 | 346 | 13.01 (br. s., 1 H), 8.13 (dd, J = 9.23, 5.27 Hz, 1 H), 7.76 (dd, J = 6.81, 2.42 Hz, 1 H), 7.41-7.47 (m, 1 H), 7.37 (dd, J = 9.67, 2.64 Hz, 1 H), 7.21-7.33 (m, 3 H), 4.69 (s, 2 H) | 99 |
| 146 | 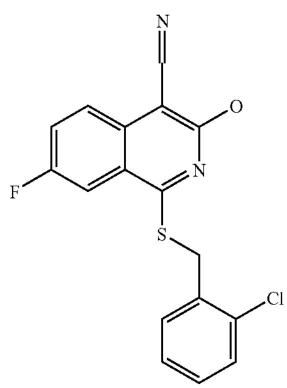 | 346 | 12.82 (br. s., 1 H), 7.66-7.86 (m, 4 H), 7.40-7.49 (m, 1 H), 7.19-7.32 (m, 2 H), 4.70 (s, 2 H) | 97 |
| 147 | 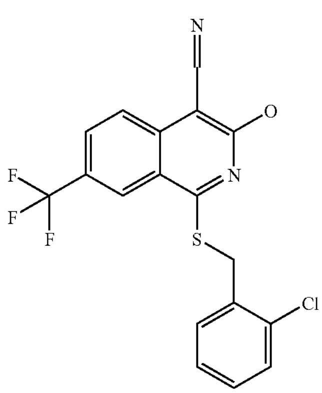 | 396 | 13.33 (br. s., 1 H), 8.23 (s, 1 H), 8.03 (d, J = 8.80 Hz, 1 H), 7.91 (d, J = 8.80 Hz, 1 H), 7.76 (dd, J = 7.15, 2.20 Hz, 1 H), 7.39-7.49 (m, 1 H), 7.18-7.32 (m, 2 H), 4.73 (s, 2 H) | 99 |

TABLE 4-continued

| Example | Structure | MS [M + H] | ¹H NMR | Purity |
|---|---|---|---|---|
| 148 | 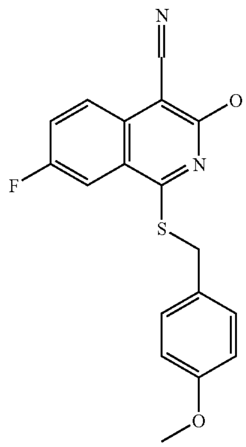 | 341 | 12.81 (br. s., 1 H), 7.81-7.88 (m, 1 H), 7.79 (d, J = 8.79 Hz, 2 H), 7.44 (d, J = 8.35 Hz, 2 H), 6.87 (d, J = 8.79 Hz, 2 H), 4.60 (s, 2 H), 3.71 (s, 3 H) | 99 |
| 149 | 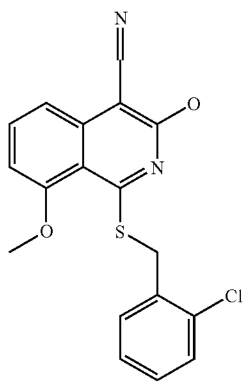 | 358 | 7.61 (t, J = 8.13 Hz, 1 H), 7.47-7.57 (m, 2 H), 7.37-7.45 (m, 1 H), 7.19-7.25 (m, 2 H), 6.78 (d, J = 7.91 Hz, 1 H), 6.62 (br. s., 1 H), 4.48 (s, 2 H), 4.00 (s, 3 H) | 99 |
| 150 | 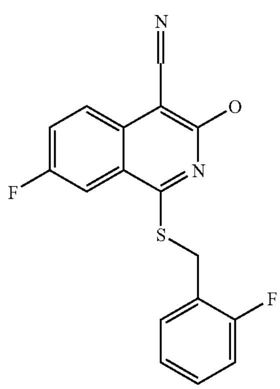 | 329 | 7.98 (dd, J = 9.23, 4.83 Hz, 1 H), 7.73 (dd, J = 9.23, 2.64 Hz, 1 H), 7.50-7.60 (m, 1 H), 7.45 (t, J = 7.03 Hz, 1 H), 7.26-7.33 (m, 1 H), 7.03-7.16 (m, 2 H), 6.65 (br. s., 1 H), 4.59 (s, 2 H) | 99 |
| 151 | 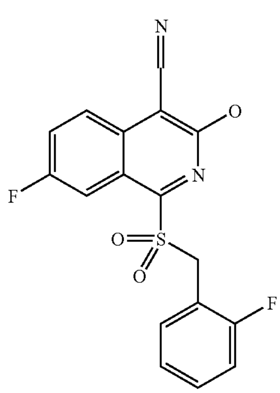 | 361 | 8.47 (dd, J = 9.67, 2.64 Hz, 1 H), 8.16 (dd, J = 9.45, 5.05 Hz, 1 H), 7.62-7.73 (m, 1 H), 7.46-7.54 (m, 1 H), 7.29-7.38 (m, 1 H), 7.16 (t, J = 7.47 Hz, 1 H), 6.98 (t, J = 9.23 Hz, 1 H), 4.89 (s, 2 H) | 99 |

TABLE 4-continued

| Example | Structure | MS [M + H] | ¹H NMR | Purity |
|---|---|---|---|---|
| 152 | 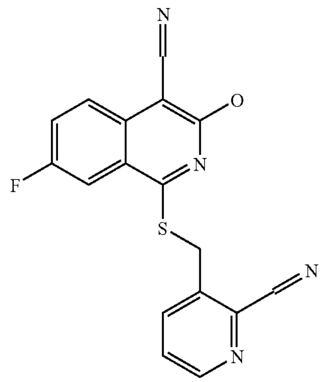 | 337 | 12.88 (br. s., 1 H), 8.64 (d, J = 4.83 Hz, 1 H), 8.35 (d, J = 6.59 Hz, 1 H), 7.75-7.91 (m, 3 H), 7.69 (dd, J = 7.91, 4.83 Hz, 1 H), 4.84 (s, 2 H) | 94 |
| 153 | 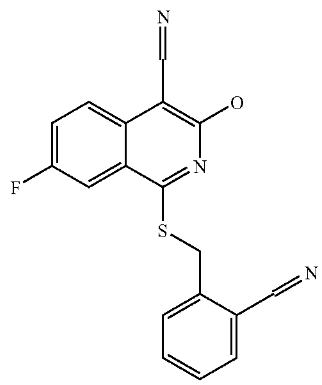 | 336 | 12.85 (br. s., 1 H), 7.69-7.90 (m, 5 H), 7.56-7.66 (m, 1 H), 7.43 (t, J = 7.69 Hz, 1 H), 4.77 (s, 2 H) | 99 |
| 154 | 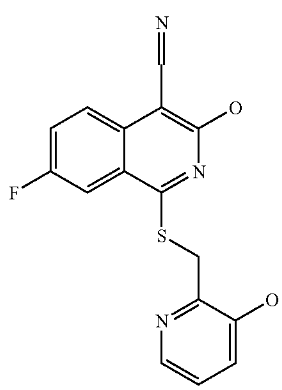 | 328 | 10.75 (br. s., 1 H), 8.02 (d, J = 4.83 Hz, 1 H), 7.78-7.85 (m, 2 H), 7.70-7.78 (m, 1 H), 7.23-7.38 (m, 2 H), 4.72 (s, 2 H) | 95 |
| 155 | 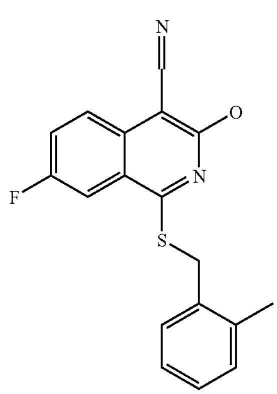 | 325 | 12.76 (br. s., 1 H), 7.63-7.85 (m, 3 H), 7.47 (d, J = 7.03 Hz, 1 H), 6.98-7.24 (m, 3 H), 4.61 (s, 2 H), 2.32 (s, 3 H) | 99 |

TABLE 4-continued

| Example | Structure | MS [M + H] | ¹H NMR | Purity |
|---|---|---|---|---|
| 156 | 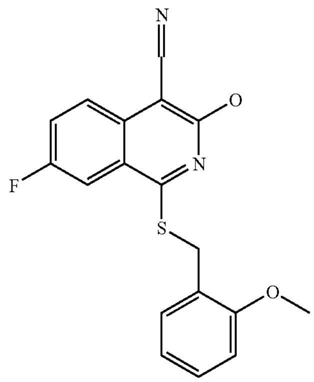 | 341 | 12.78 (br. s., 1 H), 7.81-7.88 (m, 1 H), 7.71-7.80 (m, 2 H), 7.58 (dd, J = 7.47, 1.76 Hz, 1 H), 7.23-7.32 (m, 1 H), 7.02 (d, J = 7.47 Hz, 1 H), 6.88 (t, J = 7.47 Hz, 1 H), 4.60 (s, 2 H), 3.83 (s, 3 H) | 99 |
| 157 | 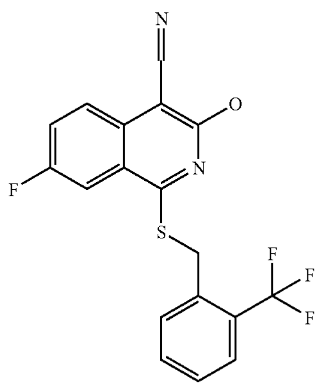 | 379 | 12.90 (br. s., 1 H), 7.83-7.93 (m, 2 H), 7.72-7.83 (m, 3 H), 7.65 (t, J = 7.47 Hz, 1 H), 7.53 (t, J = 7.69 Hz, 1 H), 4.82 (s, 2 H) | 99 |
| 158 | 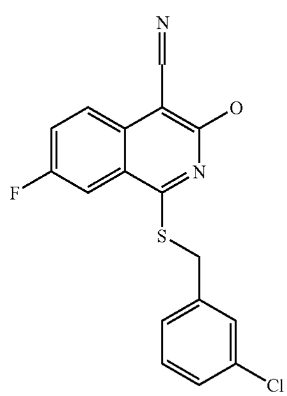 | 346 | 7.99 (dd, J = 9.01, 5.05 Hz, 1 H), 7.74 (dd, J = 9.23, 2.20 Hz, 1 H), 7.50-7.61 (m, 1 H), 7.42 (s, 1 H), 7.26-7.35 (m, 3 H), 6.87 (br. S., 1 H), 4.53 (s, 2 H) | 99 |
| 159 | 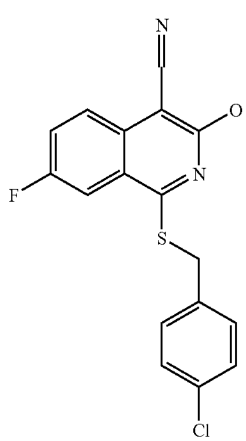 | 346 | 12.76 (br. s., 1 H), 7.66-7.88 (m, 3 H), 7.51 (d, J = 8.35 Hz, 2 H), 7.31 (d, J = 8.35 Hz, 2 H), 4.59 (s, 2 H) | 99 |

TABLE 4-continued

| Example | Structure | MS [M + H] | ¹H NMR | Purity |
|---|---|---|---|---|
| 160 | 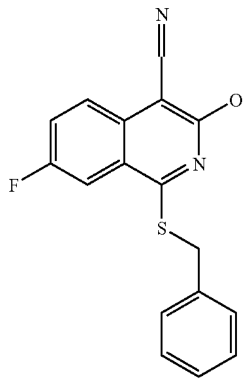 | 311 | 12.75 (br. s., 1 H), 7.64-7.87 (m, 3 H), 7.46 (d, J = 7.03 Hz, 2 H), 7.07-7.35 (m, 3 H), 4.60 (s, 2 H) | 99 |
| 161 | 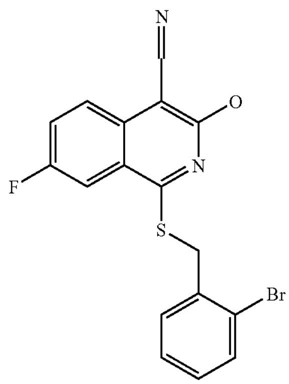 | 390 | 12.88 (br. s., 1 H), 7.71-7.94 (m, 4 H), 7.66 (d, J = 7.91 Hz, 1 H), 7.35 (t, J = 7.03 Hz, 1 H), 7.18-7.28 (m, 1 H), 4.75 (s, 2 H) | 99 |
| 162 | 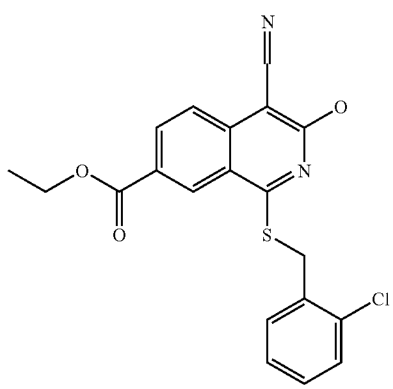 | 400 | 13.32 (br. s., 1 H), 8.52 (s, 1 H), 8.19 (d, J = 8.80 Hz, 1 H), 7.69-7.87 (m, 2 H), 7.45 (d, J = 7.70 Hz, 1 H), 7.18-7.35 (m, 2 H), 4.72 (s, 2 H), 4.30 (q, J = 7.15 Hz, 2 H), 1.28 (t, J = 7.15 Hz, 3 H) | 99 |
| 163 | 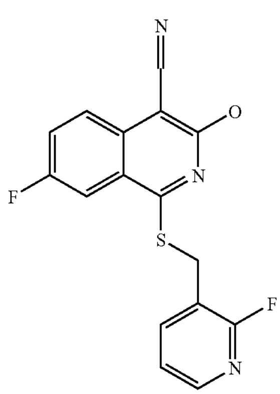 | 330 | 12.79 (br. s., 1 H), 8.17-8.33 (m, 1 H), 8.08 (d, J = 4.39 Hz, 1 H), 7.65-7.87 (m, 3 H), 7.17-7.34 (m, 1 H), 4.60 (s, 2 H) | 99 |

TABLE 4-continued

| Example | Structure | MS [M + H] | ¹H NMR | Purity |
|---|---|---|---|---|
| 164 | 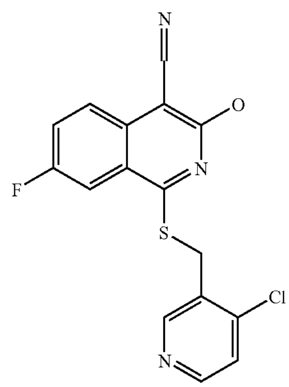 | 347 | 12.86 (br. s., 1 H), 9.01 (s, 1 H), 8.43 (d, J = 5.71 Hz, 1 H), 7.67-7.86 (m, 3 H), 7.59 (d, J = 5.71 Hz, 1 H), 4.70 (s, 2 H) | 99 |
| 165 | 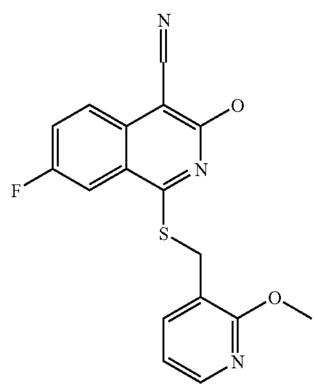 | 342 | 12.72 (br. s., 1 H), 8.03 (d, J = 3.30 Hz, 1 H), 7.95 (d, J = 5.50 Hz, 1 H), 7.62-7.85 (m, 3 H), 6.88 (dd, J = 7.15, 4.95 Hz, 1 H), 4.51 (s, 2 H), 3.87 (s, 3 H) | 99 |
| 166 | 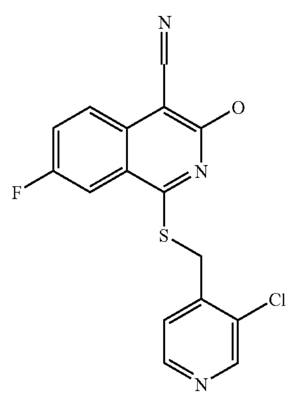 | 347 | 12.91 (br. s., 1 H), 8.65 (s, 1 H), 8.46 (d, J = 4.83 Hz, 1 H), 7.70-7.94 (m, 4 H), 4.74 (s, 2 H) | 99 |
| 167 | 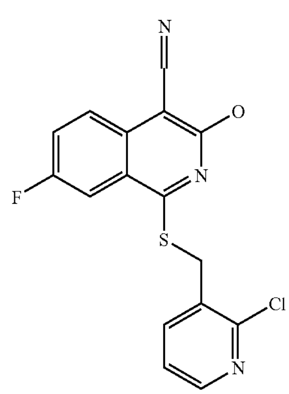 | 347 | 12.80 (br. s., 1 H), 8.27 (dd, J = 4.61, 1.98 Hz, 1 H), 8.22 (dd, J = 7.69, 1.98 Hz, 1 H), 7.71-7.84 (m, 3 H), 7.34 (dd, J = 7.69, 4.61 Hz, 1 H), 4.66 (s, 2 H) | 99 |

TABLE 4-continued

| Example | Structure | MS [M + H] | ¹H NMR | Purity |
|---|---|---|---|---|
| 168 | 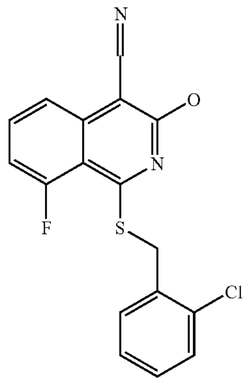 | 346 | 13.02 (br. s., 1 H), 7.68-7.90 (m, 2 H), 7.59 (d, J = 7.91 Hz, 1 H), 7.40-7.54 (m, 1 H), 7.18-7.41 (m, 3 H), 4.69 (s, 2 H) | 99 |
| 169 | 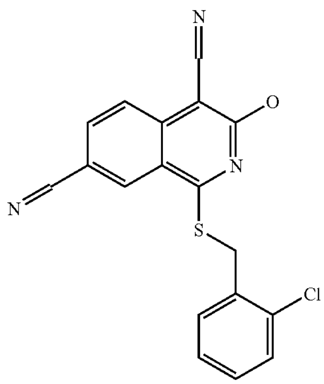 | 353 | 8.54 (s, 1 H), 8.02 (d, J = 8.79 Hz, 1 H), 7.81 (d, J = 8.79 Hz, 1 H), 7.76 (dd, J = 7.25, 2.42 Hz, 1 H), 7.41-7.48 (m, 1 H), 7.20-7.32 (m, 2 H), 4.71 (s, 2 H) | 99 |
| 170 | 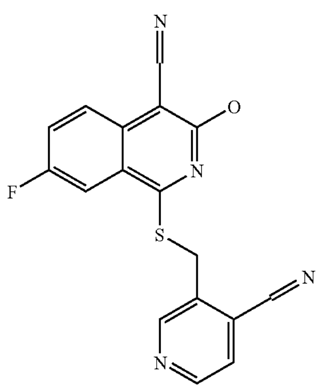 | 337 | 12.91 (br. s., 1 H), 9.17 (s, 1 H), 8.66 (d, J = 4.83 Hz, 1 H), 7.65-7.91 (m, 4 H), 4.76 (s, 2 H) | 97 |
| 171 | 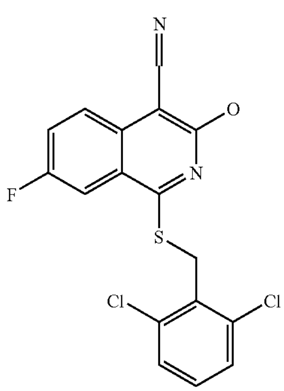 | 380 | 12.88 (br. s., 1 H), 7.79-7.87 (m, 1 H), 7.70-7.79 (m, 2 H), 7.51 (d, J = 8.25 Hz, 2 H), 7.37 (t, J = 8.25 Hz, 1 H), 4.85 (s, 2 H) | 98 |

TABLE 4-continued

| Example | Structure | MS [M + H] | ¹H NMR | Purity |
|---|---|---|---|---|
| 172 | 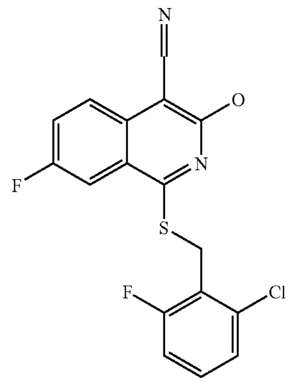 | 364 | 12.87 (br. s., 1 H), 7.78-7.85 (m, 1 H), 7.69-7.78 (m, 2 H), 7.33-7.44 (m, 2 H), 7.27 (t, J = 8.25 Hz, 1 H), 4.75 (s, 2 H) | 99 |
| 173 | 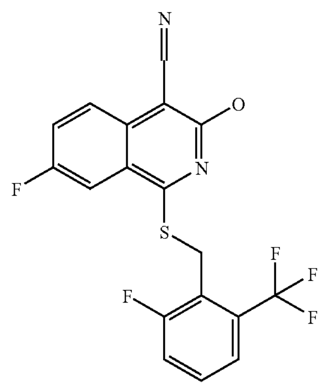 | 397 | 12.94 (br. s., 1 H), 7.84-7.92 (m, 1 H), 7.76-7.83 (m, 2 H), 7.63-7.71 (m, 3 H), 4.81 (s, 2 H) | 99 |
| 174 | 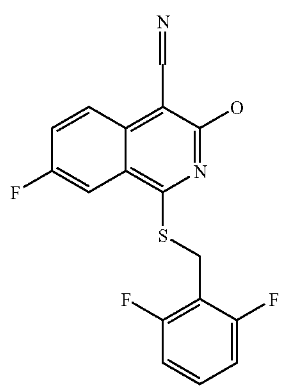 | 347 | 12.92 (br. s., 1 H), 7.84-7.91 (m, 1 H), 7.75-7.83 (m, 2 H), 7.42-7.51 (m, 1 H), 7.19 (t, J = 7.70 Hz, 2 H), 4.74 (d, J = 5.50 Hz, 2 H) | 99 |
| 175 | 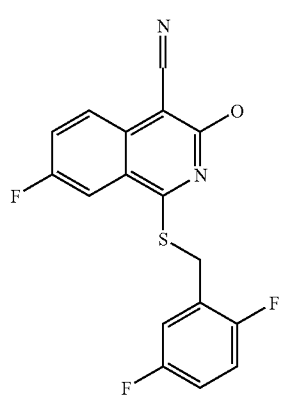 | 347 | 12.87 (br. s., 1 H), 7.82-7.88 (m, 1 H), 7.75-7.82 (m, 2 H), 7.67 (dd, J = 8.80, 6.05 Hz, 1 H), 7.22-7.31 (m, 1 H), 7.11-7.21 (m, 1 H), 4.64 (s, 2 H) | 99 |

TABLE 4-continued

| Example | Structure | MS [M + H] | ¹H NMR | Purity |
|---|---|---|---|---|
| 176 | 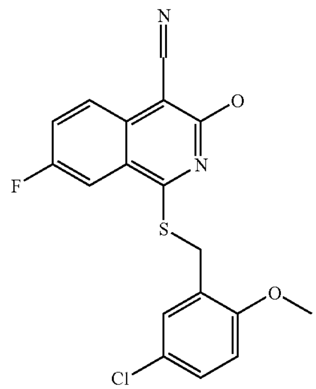 | 376 | 12.82 (br. s., 1 H), 7.76-7.82 (m, 1 H), 7.69-7.76 (m, 2 H), 7.67 (d, J = 2.64 Hz, 1 H), 7.26 (dd, J = 8.79, 3.08 Hz, 1 H), 6.99 (d, J = 9.23 Hz, 1 H), 4.51 (s, 2 H), 3.78 (s, 3 H) | 99 |
| 177 | 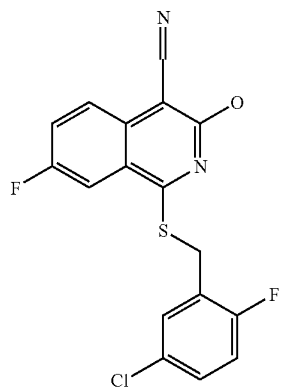 | 364 | 12.92 (br. s., 1 H), 7.69-7.99 (m, 4 H), 7.34-7.47 (m, 1 H), 7.28 (t, J = 9.23 Hz, 1 H), 4.65 (s, 2 H) | 99 |
| 178 | 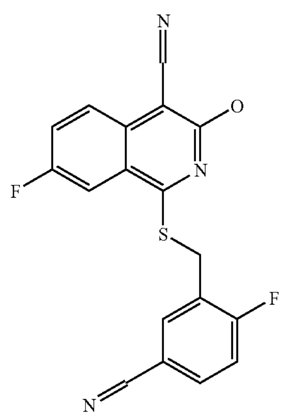 | 354 | 12.84 (br. s., 1 H), 8.33 (d, J = 7.03 Hz, 1 H), 7.67-7.87 (m, 4 H), 7.42 (t, J = 9.23 Hz, 1 H), 4.62 (s, 2 H) | 99 |
| 179 | 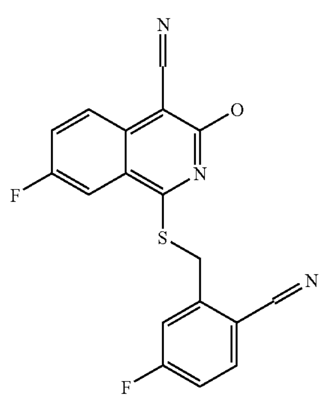 | 354 | 12.96 (br. s., 1 H), 7.99 (dd, J = 8.79, 5.71 Hz, 1 H), 7.70-7.91 (m, 4 H), 7.33-7.44 (m, 1 H), 4.79 (s, 2 H) | 99 |

TABLE 4-continued

| Example | Structure | MS [M + H] | ¹H NMR | Purity |
|---|---|---|---|---|
| 180 | 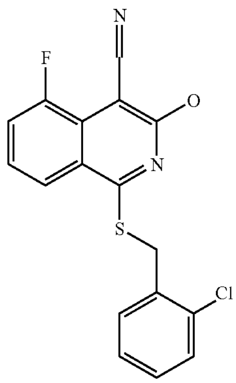 | 346 | 13.07 (br. s., 1 H), 7.90 (d, J = 7.91 Hz, 1 H), 7.79-7.84 (m, 1 H), 7.64 (dd, J = 11.86, 7.03 Hz, 1 H), 7.40-7.51 (m, 2 H), 7.27-7.36 (m, 2 H), 4.74 (s, 2 H) | 99 |
| 181 | 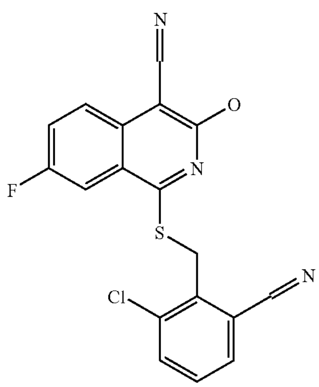 | 371 | 12.95 (br. s., 1 H), 7.80-7.93 (m, 3 H), 7.72-7.80 (m, 2 H), 7.55 (t, J = 7.91 Hz, 1 H), 4.87 (s, 2 H) | 99 |
| 182 | 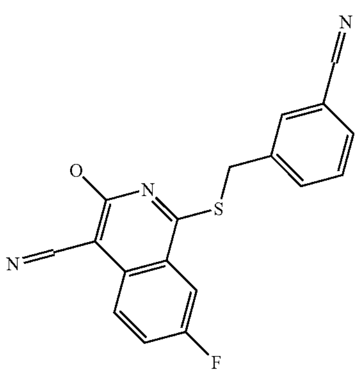 | 336 | | 98 |
| 183 | 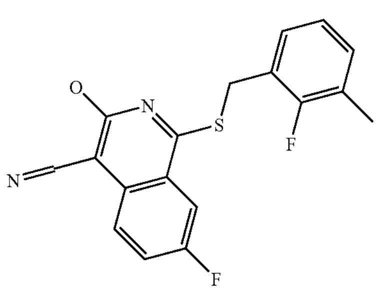 | 343 | | 97 |

TABLE 4-continued

| Example | Structure | MS [M + H]  ¹H NMR | Purity |
| --- | --- | --- | --- |
| 184 | 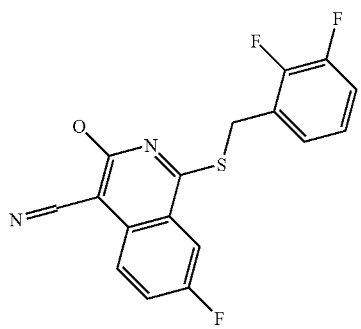 | 347 | 99 |
| 185 | 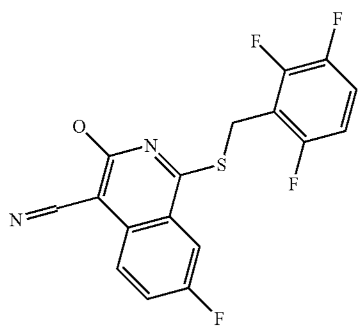 | 365 | 92 |
| 186 | 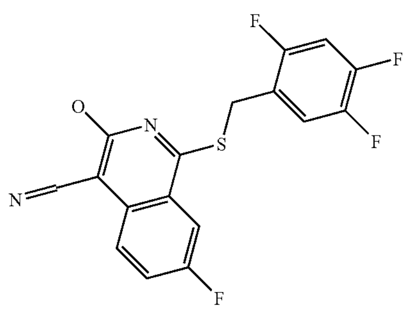 | 365 | 99 |
| 187 | 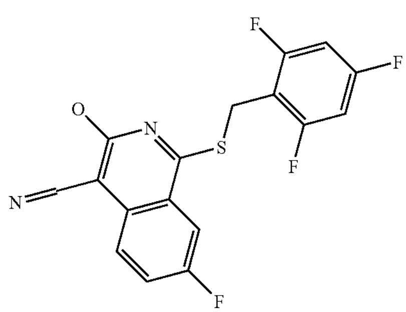 | 365 | 94 |
| 188 | 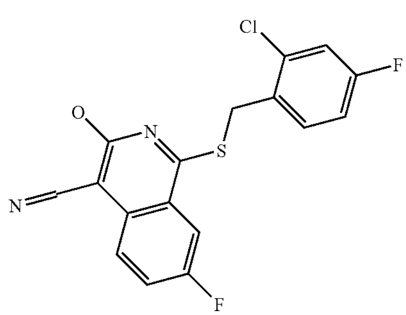 | 364 | 98 |

TABLE 4-continued

| Example | Structure | MS [M + H] $^1$H NMR | Purity |
|---|---|---|---|
| 189 | 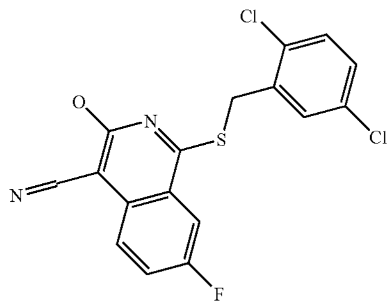 | 380 | 95 |
| 190 | 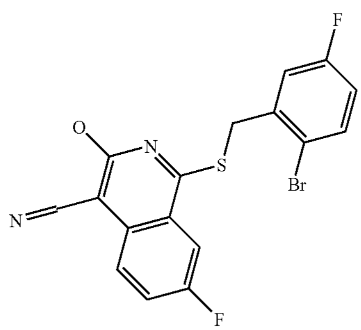 | 408 | 97 |
| 191 | 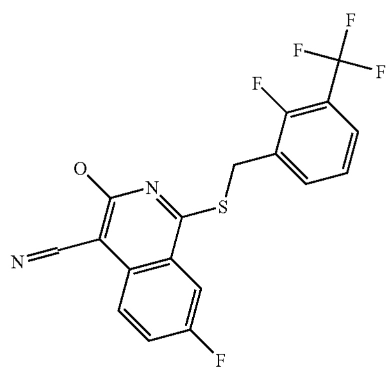 | 397 | 94 |
| 192 | 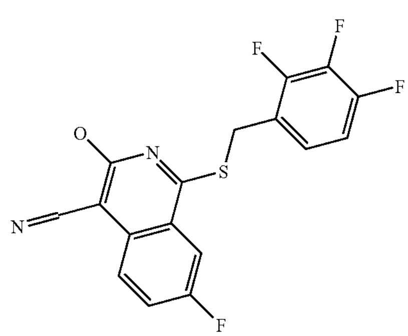 | 365 | 95 |

TABLE 4-continued

| Example | Structure | MS [M + H] $^1$H NMR | Purity |
|---------|-----------|----------------------|--------|
| 193 | 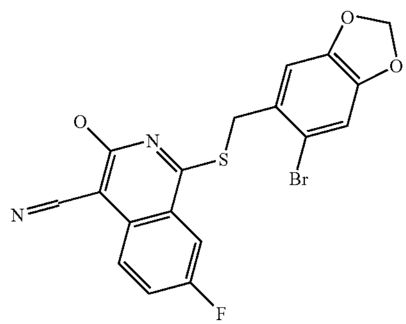 | 434 | 93 |
| 194 | 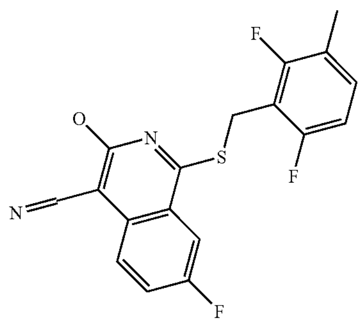 | 361 | 93 |
| 195 | 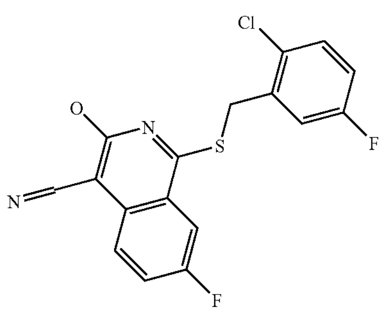 | 364 | 90 |
| 196 | 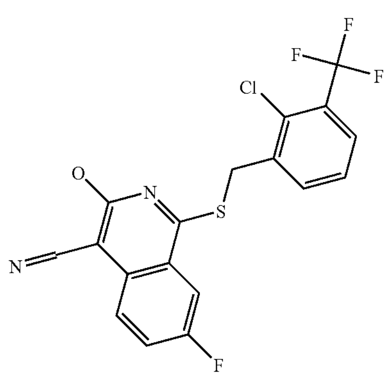 | 414 | 90 |
| 197 | 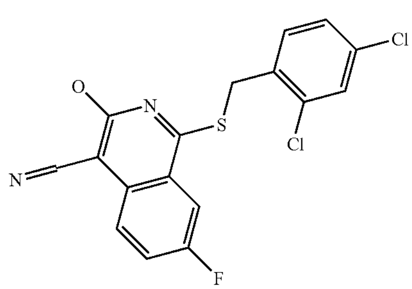 | 380 | 93 |

TABLE 4-continued

| Example | Structure | MS [M + H] ¹H NMR | Purity |
|---|---|---|---|
| 198 | 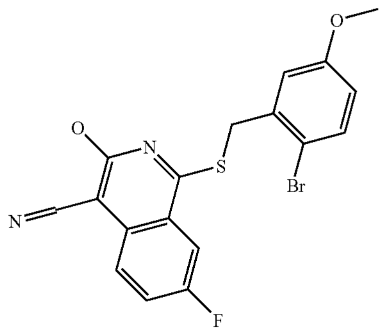 | 420 | 95 |
| 199 | 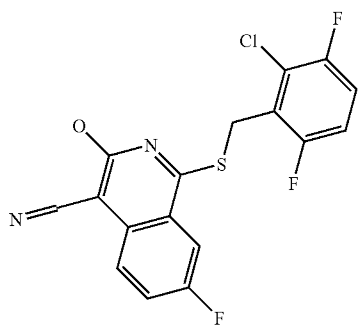 | 382 | 87 |
| 200 | 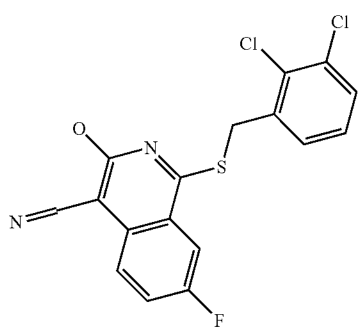 | 380 | 92 |
| 201 | 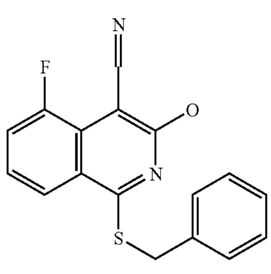 | 311 | 92 |

TABLE 4-continued
| Example | Structure | MS [M + H] ¹H NMR | Purity |
|---|---|---|---|
| 202 | 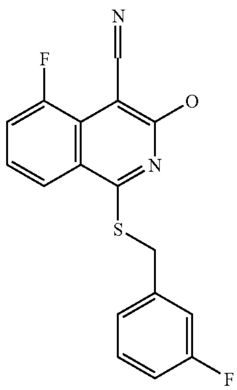 | 329 | 96 |
| 203 | 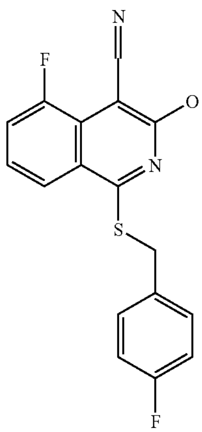 | 329 | 92 |
| 204 | 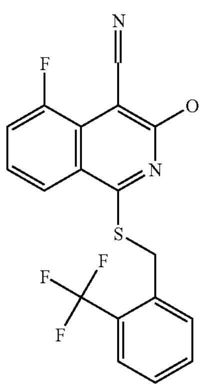 | 379 | 91 |
| 205 | 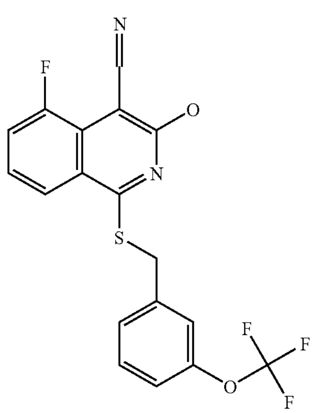 | 395 | 91 |
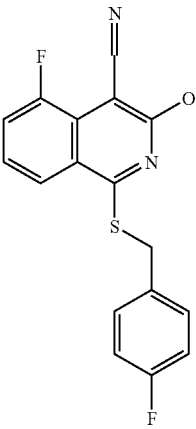

TABLE 4-continued
| Example | Structure | MS [M + H]   ¹H NMR | Purity |
|---|---|---|---|
| 206 | 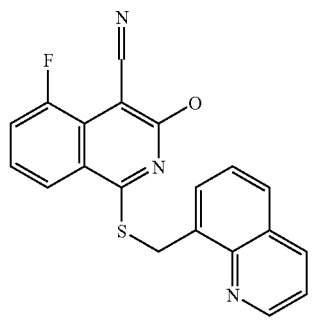 | 362 | 96 |
| 207 | 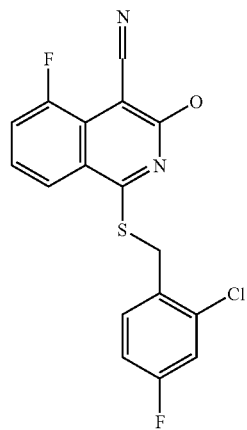 | 364 | 91 |
| 208 | 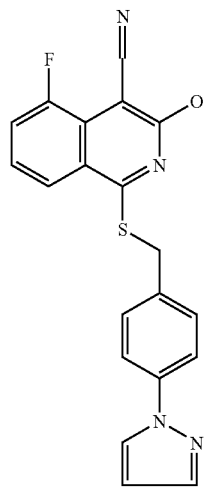 | 377 | 90 |

TABLE 4-continued
| Example | Structure | MS [M + H]  ¹H NMR | Purity |
|---------|-----------|--------------------|--------|
| 209 | 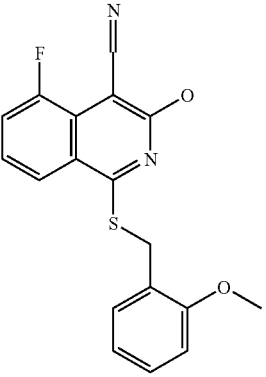 | 341 | 91 |
| 210 | 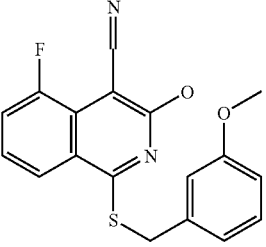 | 341 | 93 |
| 211 | 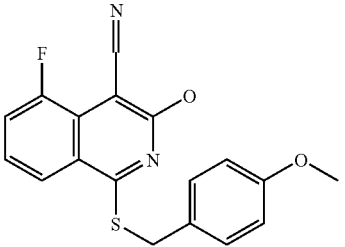 | 341 | 95 |
| 212 | 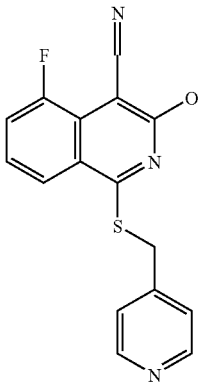 | 312 | 91 |

TABLE 4-continued

| Example | Structure | MS [M + H] | ¹H NMR | Purity |
|---------|-----------|------------|--------|--------|
| 213 | 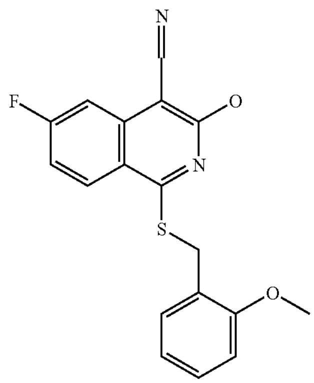 | 341 | | 95 |
| 214 | 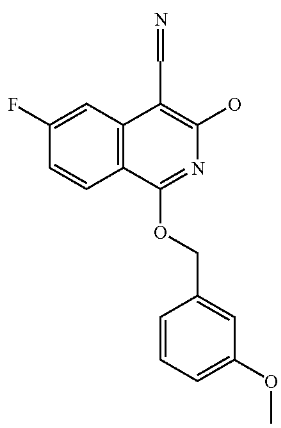 | 341 | | 93 |

Examples 215 to 241

Examples 215 to 241 in Table 5 were prepared according to the procedures described in Examples 1 to 6 or by other similar methods known to one skilled in the art, with other appropriate reagent. NMR Spectra data are reported in δ ppm using a 400 MHz spectrometer and $CD_4OD$ as the solvent. In the structures set forth in Table 5, the "—O" attached to the carbon adjacent to the nitrogen in the bicyclic core is used to denote an "—OH" group as indicated in Formula I.

TABLE 5

| Example | Structure | MS (M + H) | NMR | Purity |
|---------|-----------|------------|-----|--------|
| 215 | 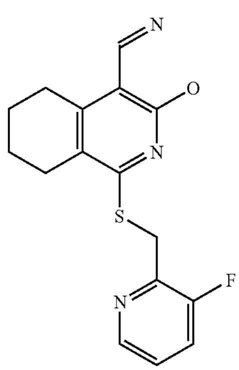 | 316 | 8.35(1 H, d, J = 4.95 Hz), 7.65(1 H, t, J = 8.52 Hz), 7.43(1 H, dd, J = 8.52, 4.12 Hz), 4.64(2 H, d, J = 2.20 Hz), 2.80(2 H, br. s.), 2.44(2 H, br. s.), 1.79(4 H, br. s.) | 97.0 |

TABLE 5-continued

| Example | Structure | MS (M + H) | NMR | Purity |
|---|---|---|---|---|
| 216 | 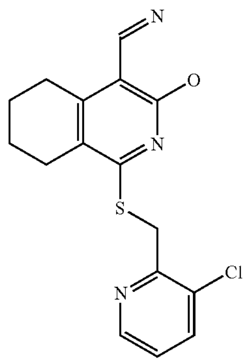 | 332 | 8.01(1 H, d, J = 7.70 Hz), 7.78(1 H, d, J = 7.70 Hz), 7.61(1 H, t, J = 7.70 Hz), 7.51(1 H, t, J = 7.15 Hz), 4.97(2 H, s), 2.79(2 H, br. s.), 2.43(2 H, br. s.), 1.78(4 H, br. s.) | 97.0 |
| 217 | 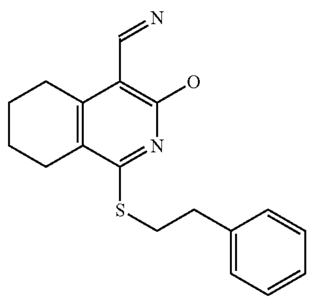 | 331 | 7.13-7.34(5 H, m), 3.44(1 H, t, J = 7.91 Hz), 2.96(2 H, t, J = 7.91 Hz), 2.78(2 H, br. s.), 2.43(2 H, br. s.), 1.78(4 H, br. s.) | 97.0 |
| 218 | 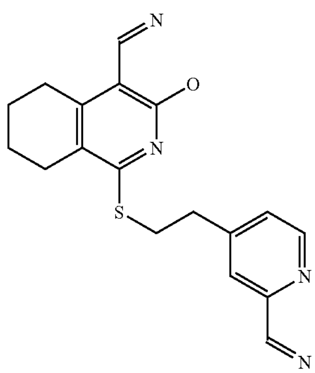 | 323 | 8.56(1 H, d, J = 3.52 Hz), 8.18(1 H, d, J = 7.91 Hz), 7.57(1 H, dd, J = 8.13, 5.05 Hz), 7.21-7.27(1 H, m), 4.66(2 H, s), 2.81 (2 H, br. s.), 2.45(2 H, br. s.), 1.80(4 H, br. s.) | 96.0 |
| 219 | 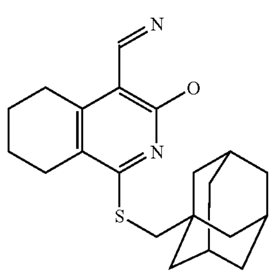 | 355 | 2.95(2 H, s), 2.76(2 H, t, J = 5.94 Hz), 1.93(4 H, br. s.), 1.47-1.77(16 H, m) | 98.0 |
| 220 | 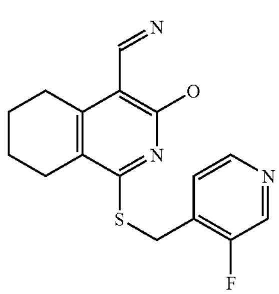 | 316 | 8.75(1 H, br. s.), 8.50(1 H, d, J = 5.05 Hz), 8.05(1 H, br. s.), 4.67(2 H, s), 2.82(2 H, t, J = 5.43 Hz), 2.50(2 H, t, J = 5.43 Hz), 1.76-1.90(4 H, m) | 95.0 |

TABLE 5-continued

| Example | Structure | MS (M + H) | NMR | Purity |
|---|---|---|---|---|
| 221 | 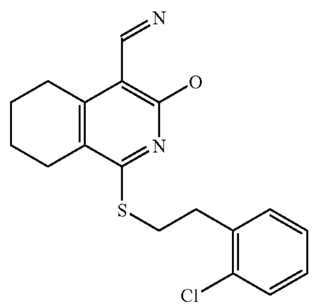 | 345 | 7.37(2 H, dd, J = 7.58, 1.77 Hz), 7.17-7.29(2 H, m), 3.51(2 H, t, J = 7.45 Hz), 3.14(2 H, t, J = 7.33 Hz), 2.81(2 H, t, J = 5.68 Hz), 2.84(2 H, t, J = 5.31 Hz), 1.73-1.89 (4 H, m) | 98.0 |
| 222 | 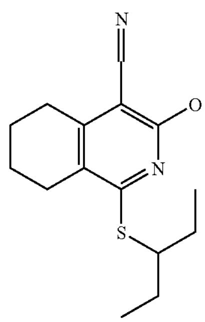 | 277 | 2.79(2 H, t, J = 6.32 Hz), 2.72(2 H, t, J = 6.05 Hz), 1.61-1.81(8 H, m), 1.02(6 H, t, J = 7.42 Hz) | 97.0 |
| 223 | 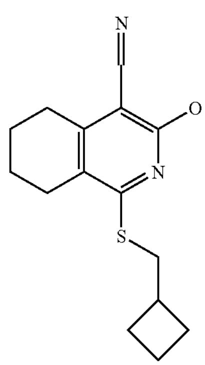 | 275 | 2.78(2 H, t, J = 5.50 Hz), 2.53-2.68(1 H, m), 2.04-2.16(2 H, m), 1.66-1.93(8 H, m) | 96.0 |
| 224 | 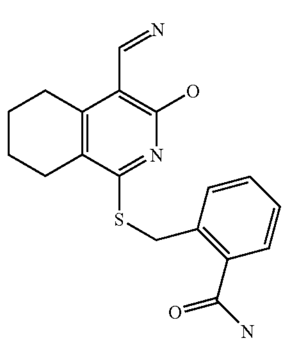 | 340 | 7.55(2 H, d, J = 33.85 Hz), 7.36(2 H, d, J = 17.68 Hz), 5.44(2 H, br. s.), 2.77(2 H, br. s.), 2.46(2 H, br. s.). 1.78(4 H, br. s.) | 94.0 |

TABLE 5-continued

| Example | MS (M + H) | NMR | Purity |
|---|---|---|---|
| 225 | 305 | 3.89-4.00(2 H, m), 3.35-3.45(2 H, m), 3.19(2 H, d, J = 6.57 Hz), 2.81(2 H, t, J = 5.56 Hz), 2.51(2 H, t, J = 5.68 Hz), 1.73-1.91(7 H, m), 1.32-1.45(2 H, m) | 96.0 |
| 226 | 380 | 7.95(1 H, d, J = 8.24 Hz), 7.59(1 H, dd, J = 10.99, 7.70 Hz), 7.41-7.47(1 H, m), 7.34(1 H, d, J = 7.15 Hz), 4.85(2 H, s), 4.15(1 H, t, J = 7.70 Hz), 4.00(1 H, t, J = 7.70 Hz), 2.77(2 H, br. s.), 2.42-2.47(1 H, m), 2.38(2 H, br. s.), 2.25-2.34(1 H, m), 1.70-1.81(6 H, m) | 95.0 |
| 227 | 345 | 7.55(1 H, d, J = 6.05 Hz), 7.34(1 H, d, J = 8.24 Hz), 7.27(1 H, d, J = 7.70 Hz), 7.22(1 H, d, J = 6.05 Hz), 5.56(1 H, br. s., J = 7.10 Hz), 2.75(2 H, br. s.), 2.35(2 H, br. s.), 1.65-1.77(7 H, m) | 93.0 |
| 228 | 325 | | 95.9 |

TABLE 5-continued

| Example | Structure | MS (M + H) | NMR | Purity |
|---|---|---|---|---|
| 229 | 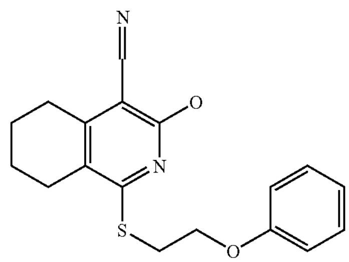 | 327 | | 98.5 |
| 230 | 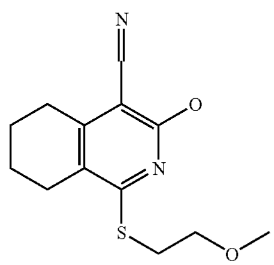 | 265 | | 100.0 |
| 231 | 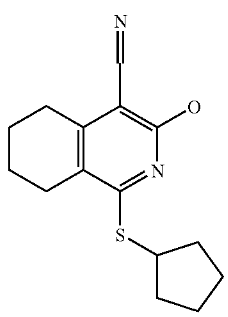 | 275 | | 98.0 |
| 232 | 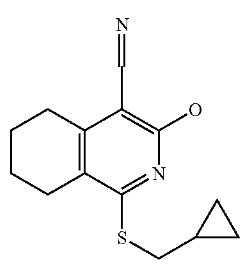 | 261 | | 100.0 |
| 233 | 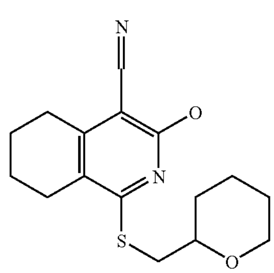 | 305 | | 100.0 |

TABLE 5-continued
| Example | Structure | MS (M + H) | NMR | Purity |
|---------|-----------|------------|-----|--------|
| 234 | 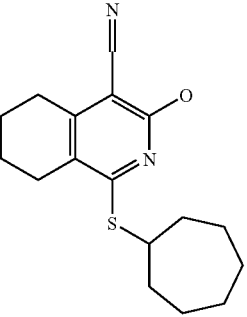 | 303 | | 99.2 |
| 235 | 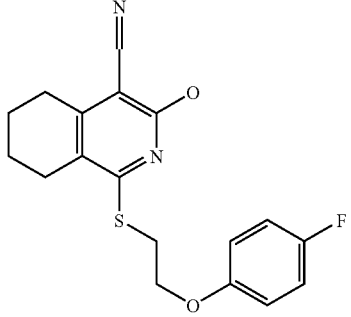 | 345 | | 98.2 |
| 236 | 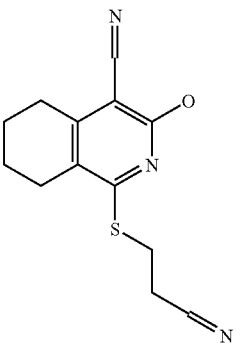 | 260 | | 100.0 |
| 237 | 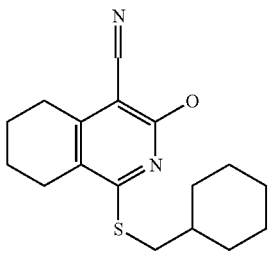 | 303 | | 100.0 |

TABLE 5-continued

| Example | Structure | MS (M + H) | NMR | Purity |
|---|---|---|---|---|
| 238 | 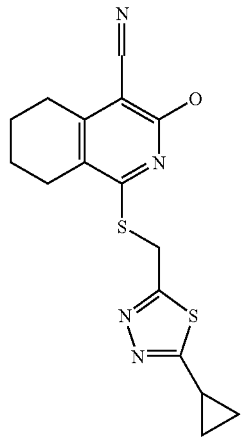 | 345 | | 100.0 |
| 239 | 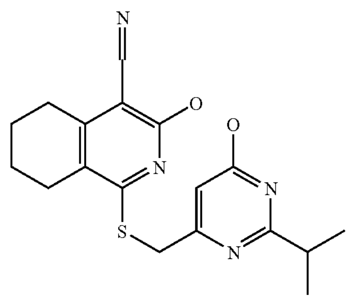 | 357 | | 100.0 |
| 240 | 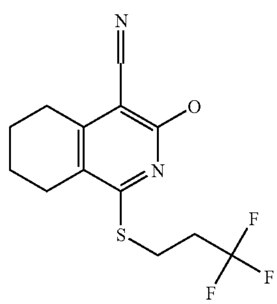 | 303 | | 96.8 |
| 241 | 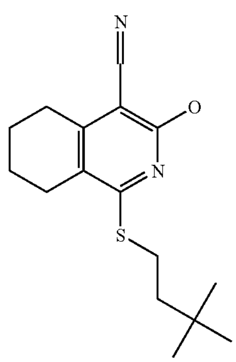 | 291 | | 100.0 |

Example 242

8-(2-Chlorobenzylthio)-6-ethoxy-1,7-naphthyridine-5-carbonitrile

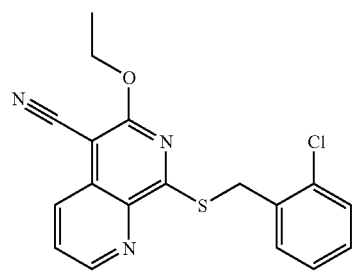

Step 1: 6-Ethoxy-1,7-naphthyridin-8-amine

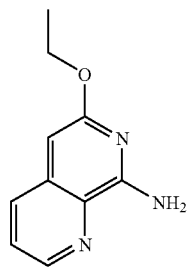

To a 1 L round bottom flask was added 3-(cyanomethyl)picolinonitrile (3.56 g, 24.9 mmol), absolute ethanol (400 mL), followed by sodium ethoxide (11.1 mL, 21% solution w/v, 29.9 mmol). The mixture was stirred at reflux for 3 h. The solvent was then concentrated and the resultant residue was dissolved in ethyl acetate (200 mL), washed with brine, dried over $Na_2SO_4$ and concentrated. The residue was purified by silica gel to yield 6-ethoxy-1,7-naphthyridin-8-amine as a pale yellow solid (0.66 g, 3.49 mmol, 14%). $^1$H NMR (400 MHz, CDCl$_3$): δ ppm 8.53 (dd, J=3.95, 1.76 Hz, 1H), 7.83 (dd, J=8.35, 1.76 Hz, 1H), 7.39 (dd, J=8.35, 4.39 Hz, 1H), 6.15 (s, 1H), 5.87 (br. s., 2H), 4.22 (q, J=7.03 Hz, 2H), 1.45 (t, J=7.03 Hz, 3H). LC/MS m/z 190 [M+H].

Step 2: 5-Bromo-6-ethoxy-1,7-naphthyridin-8-amine

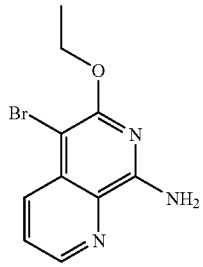

To a 250 mL round bottom flask was added 6-ethoxy-1,7-naphthyridin-8-amine (0.65 g, 3.43 mmol), glacial acetic acid (20 mL), followed by the dropwise addition of bromine (0.60 g, 3.78 mmol) dissolved in carbontetrachloride (40 mL). After addition was complete, the mixture was stirred for 2 h then neutralized with saturated $NaHCO_3$ and extracted with ethyl acetate. The organic layer was washed with brine, dried over $Na_2SO_4$ and concentrated. The resultant residue was purified by silica gel to yield 5-bromo-6-ethoxy-1,7-naphthyridin-8-amine as a pale yellow solid (0.6 g, 2.24 mmol, 65%). $^1$H NMR (400 MHz, CDCl$_3$): δ ppm 8.53 (d, J=3.95 Hz, 1H), 8.22 (d, J=8.79 Hz, 1H), 7.50 (dd, J=8.57, 4.17 Hz, 1H), 5.87 (br. s., 2H), 4.48 (q, J=7.03 Hz, 2H), 1.44 (t, J=7.03 Hz, 3H). LC/MS m/z 270 [M+H].

Step 3: 5-Bromo-6-ethoxy-8-fluoro-1,7-naphthyridine

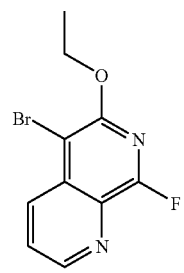

To a 100 mL round bottom flask was added 5-bromo-6-ethoxy-1,7-naphthyridin-8-amine (500 mg, 1.86 mmol), followed by pyridine hydrogen fluoride (10 mL). The mixture was cooled to 0° C. and sodium nitrite (0.154 mg, 2.24 mmol) was added in portions. The mixture was slowly warmed to room temperature over a period of 3 h. The reaction was neutralized with saturated $NaHCO_3$ and extracted with ethyl acetate. The organic layer was washed with brine, dried over $Na_2SO_4$ and concentrated. The resultant residue was purified by silica gel to yield 5-bromo-6-ethoxy-8-fluoro-1,7-naphthyridine as a pale yellow solid (430 mg, 1.59 mmol, 85%). $^1$H NMR (400 MHz, CDCl$_3$): δ ppm 8.87 (d, J=3.52 Hz, 1H), 8.42 (d, J=8.79 Hz, 1H), 7.65 (dd, J=8.13, 3.30 Hz, 1H), 4.55 (q, J=7.03 Hz, 2H), 1.49 (t, J=7.03 Hz, 3H). LC/MS m/z 273 [M+H].

Step 4: 5-Bromo-8-(2-chlorobenzylthio)-6-ethoxy-1,7-naphthyridine

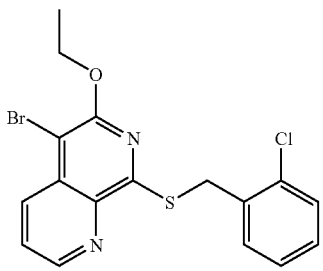

To a 5 mL microwave reactor vial was added 5-bromo-6-ethoxy-8-fluoro-1,7-naphthyridine (100 mg, 0.37 mmol), a large excess of $K_2CO_3$, followed by DMF (5 mL). (2-chlorophenyl)methanethiol (70 mg, 0.44 mmol) was then added to the mixture, the vessel was capped and heated under microwave irradiation for 20 min at 100° C. The reaction was diluted with water and extracted with ethyl acetate. The organic layer was washed with brine, dried over Na$_2$SO$_4$ and concentrated. The resultant residue was purified by silica gel to yield 5-bromo-8-(2-chlorobenzylthio)-6-ethoxy-1,7-naphthyridine as a pale yellow solid (100 mg, 0.24 mmol, 66%). $^1$H NMR (400 MHz, CDCl$_3$): δ ppm 8.74 (d, J=2.64 Hz, 1H), 8.34 (d, J=7.47 Hz, 1H), 7.50-7.68 (m, 2H), 7.35-7.48 (m, 1H), 7.11-7.22 (m, 2H), 4.67 (s, 2H), 4.53 (q, J=7.03 Hz, 2H), 1.41 (t, J=7.03 Hz, 3H). LC/MS m/z 411 [M+H].

Step 5: Example 242

To a 5 mL microwave reactor vial was added 5-bromo-8-(2-chlorobenzylthio)-6-ethoxy-1,7-naphthyridine (100 mg, 0.23 mmol), NMP (5 mL), followed by CuCN (52 mg, 0.59 mmol). The vessel was capped and heated under microwave irradiation for 45 min at 180° C. The reaction was diluted with water and extracted with ethyl acetate. The organic layer was washed with brine, dried over Na$_2$SO$_4$ and concentrated. The resultant residue was purified by silica gel to yield Example 242 as a pale yellow solid (15 mg, 0.042 mmol, 18%). $^1$H NMR (400 MHz, CD$_2$Cl$_2$): δ ppm 8.68 (d, J=3.85 Hz, 1H), 8.15 (d, J=8.80 Hz, 1H), 7.58 (dd, J=8.52, 4.12 Hz, 1H), 7.42-7.52 (m, 1H), 7.28-7.41 (m, 1H), 7.10-7.23 (m, 2H), 4.61 (s, 2H), 4.55 (q, J=7.15 Hz, 2H), 1.36 (t, J=7.15 Hz, 3H). LC/MS m/z 356 [M+H].

Example 243

5-Chloro-8-(2-chlorobenzylthio)-1,7-naphthyridin-6-ol

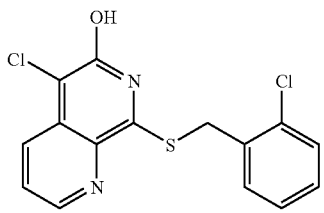

Step 1: 6-Methoxy-1,7-naphthyridin-8-amine

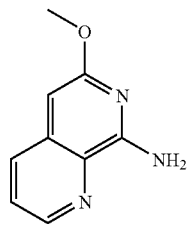

To a 1 L round bottom flask was added 3-(cyanomethyl)picolinonitrile (63.6 mmol), MeOH (500 mL), followed by sodium methoxide (76.3 mmol). The mixture was heated at reflux for 18 h, after which time the solvent was removed. The residue was diluted with water (400 mL) and extracted with ethyl acetate (2×200 mL). The combined organic layers were washed with brine, dried over Na$_2$SO$_4$ and concentrated. The resultant crude residue was purified by silica gel to yield 6-methoxy-1,7-naphthyridin-8-amine (1.05 g, 5.99 mmol, 9.4%) as an off-white solid. $^1$H NMR (400 MHz, DMSO-d$_6$): δ ppm 8.50 (d, J=2.75 Hz, 1H), 7.95 (d, J=8.24 Hz, 1H), 7.48 (dd, J=8.25, 4.40 Hz, 1H), 7.05 (s, 2H), 6.16 (s, 1H), 3.79 (s, 3H).

Step 2: 5-Chloro-6-methoxy-1,7-naphthyridin-8-amine

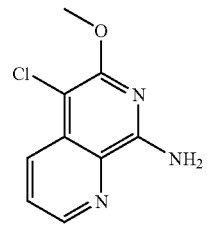

To a 200 mL round bottom flask was added 6-ethoxy-1,7-naphthyridin-8-amine (3.42 mmol), DCM (75 mL), followed by N-chlorosuccinimide (3.77 mmol). The mixture was heated at reflux for 18 h under Ar. The mixture was then cooled, the solvent evaporated and the resultant crude residue purified by silica gel to yield 5-chloro-6-ethoxy-1,7-naphthyridin-8-amine (480 mg, 63%) as a pale yellow solid. $^1$H NMR (400 MHz, CDCl$_3$): δ ppm 8.89 (d, J=3.95 Hz, 1H), 8.43 (d, J=8.79 Hz, 1H), 7.66 (dd, J=8.79, 3.95 Hz, 1H), 4.13 (s, 3H).

Step 2: 5-Chloro-8-fluoro-1,7-naphthyridin-6-ol

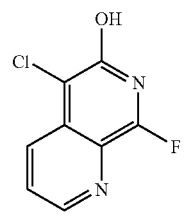

To a 25 mL round bottom flask was added 5-chloro-6-ethoxy-1,7-naphthyridin-8-amine (1.03 mmol), followed by hydrogen fluoride pyridine (5 mL). The solution was cooled to 0° C., then sodium nitrite (1.23 mmol) was added in portions. The mixture was warmed to room temperature over a period of 1 h. The reaction was then neutralized with saturated NaHCO$_3$ and extracted with ethyl acetate. The organic layer was washed with brine, dried over Na$_2$SO$_4$ and concentrated. The resultant crude residue was dissolved in dichloroethane (50 mL), then AlCl$_3$ (820 mg, 6.18 mmol) was added in one portion. The mixture was refluxed for 2 h under Ar. The solution was allowed to cool to room temperature, then diluted with water. The aqueous phase was extracted with ethyl acetate, the organic layer was washed with brine then dried over Na$_2$SO$_4$. The solvent was concentrated to yield 5-chloro-8-fluoro-1,7-naphthyridin-6-ol (180 mg, 88%) as a pale yellow solid. LC/MS m/z 199 [M+H].

Step 3: Example 243

To a 5 mL microwave reactor vial was added 5-chloro-8-fluoro-1,7-naphthyridin-6-ol (0.252 mmol), DMF (5 mL), followed by a large excess of solid K$_2$CO$_3$. To the mixture was added (2-chlorophenyl)methanethiol (48 mg, 0.302 mmol), the vial was capped and the reaction heated by microwave irradiation for 20 min at 100° C. The solution was then diluted with a solution of citric acid (50 mL, 10% w/v), and extracted with ethyl acetate. The organic phase was washed with brine, dried over Na$_2$SO$_4$, filtered and concentrated. The resultant crude residue was purified by preparative HPLC (Gradient Solvent System: From 50% A: 50% B to 0% A: 100% B; [A=10% MeOH/90% H₂O+0.1% TFA]; [B=90% MeOH/10% H₂O+0.1% TFA]; detection at 220 nm: 10 min gradient; Phenomenex Luna AXIA 30×100 mm) to provide Example 243 (15.2 mg, 18%) as a yellow solid. ¹H NMR (400 MHz, CDCl₃): δ ppm 8.77 (d, J=3.95 Hz, 1H), 8.34 (d, J=8.79 Hz, 1H), 7.50-7.69 (m, 2H), 7.33-7.41 (m, 1H), 7.12-7.22 (m, 2H), 4.58 (s, 2H). LC/MS m/z 337 [M+H].

Example 244

8-(2-Chlorobenzylthio)-6-hydroxy-3,4-dihydro-1H-pyrano[3,4-c]pyridine-5-carbonitrile

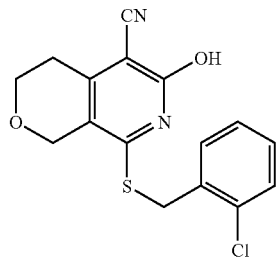

Step 1: Mixture of 6-hydroxy-8-mercapto-3,4-dihydro-1H-pyrano[3,4-c]pyridine-5-carbonitrile and 8-mercapto-3,4-dihydro-1H-pyrano[3,4-c]pyridin-6-ol

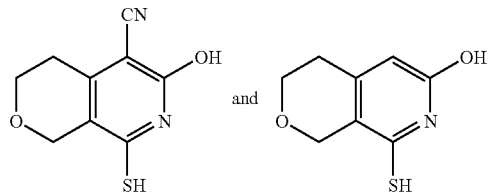

To a stirred solution of dihydro-2H-pyran-4(3H)-one (33 mmol) and malononitrile (33 mmol) in 10 mL of MeOH and 2 mL of DMF was added 6.6 mL carbon disulfide followed by the slow addition of 2 mL of Et₃N. Upon completion of addition, the solution was stirred at RT for 36 h. At the conclusion of this period, the resulting red precipitate was collected by filtration and then washed with MeOH. The red solid filter cake was then taken up in 50 mL of 1N NaOH. The resulting mixture was stirred at 150° C. for 5 h and then cooled to RT. Once at the prescribed temperature, the resulting red solution was acidified with 6 N HCl. The resulting yellow precipitate was collected by filtration, washed with water and then dried in vacuum to provide the title mixture (0.85 g, 5:1 mixture of 6-hydroxy-8-mercapto-3,4-dihydro-1H-pyrano[3,4-c]pyridine-5-carbonitrile (28%) and 8-mercapto-3,4-dihydro-1H-pyrano[3,4-c]pyridin-6-ol (6%). 6-hydroxy-8-mercapto-3,4-dihydro-1H-pyrano[3,4-c]pyridine-5-carbonitrile. LC/MS m/z 208 (M+H). 8-mercapto-3,4-dihydro-1H-pyrano[3,4-c]pyridin-6-ol. LC/MS m/z 184 (M+H).

Step 2: Example 244

To a mixture of the crude mixture of Step 1 above (6-hydroxy-8-mercapto-3,4-dihydro-1H-pyrano[3,4-c]pyridine-5-carbonitrile (0.40 mmol) and 8-mercapto-3,4-dihydro-1H-pyrano[3,4-c]pyridin-6-ol, (0.08 mmol)) and K₂CO₃ (0.57 mmol) in 10 mL of EtOH was added 2-chlorobenzyl bromide (0.57 mmol). Upon completion of addition, the reaction mixture was stirred at RT for 1 h. After this time, the reaction mixture was filtered, and the filtrate was concentrated under reduced pressure to yield a residue. The residue was purified by preparative HPLC (Gradient Solvent System: From 30% A: 70% B to 0% A: 100% B; [A=10% MeOH/90% H₂O+ 0.1% TFA]; [B=90% MeOH/10% H₂O+0.1% TFA]; detection at 220 nm: 10 min gradient; Phenomenex Luna AXIA 30×100 mm) to provide Example 244 (40 mg, 25%) as a yellow solid. Example 1: ¹H NMR (400 MHz, CD₃OD) δ ppm 7.55 (1H, d, J=6.05 Hz), 7.36-7.41 (1H, m), 7.19-7.26 (2H, m), 4.60 (2H, s), 4.42 (2H, s), 3.88 (2H, t, J=5.50 Hz), 2.85 (2H, t, J=5.50 Hz) LC/MS m/z 333 (M+H).

Examples 245 to 251

Examples 245 to 251 in Table 6 were prepared according to the procedures described in Example 244 or by other similar methods known to one skilled in the art, with other appropriate reagent. NMR Spectra data are reported in δ ppm using a 400 MHz spectrometer and CD₄OD as the solvent. In the structures set forth in Table 6, the "—O" attached to the carbon adjacent to the nitrogen in the bicyclic core is used to denote an "—OH" group as indicated in Formula I.

TABLE 6

| Example | Structure | MS (M + H) | NMR | Purity |
|---|---|---|---|---|
| 245 | 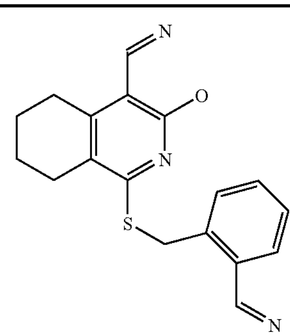 | 324 | 7.57-7.64(2 H, m), 7.46-7.52(1 H, m), 7.29-7.36(1 H, m), 4.59(2 H, s), 4.36(2 H, s), 3.80(2 H, t, J = 5.81 Hz), 2.77(2 H, t, J = 5.68 Hz) | 99 |

TABLE 6-continued

| Example | Structure | MS (M + H) | NMR | Purity |
|---|---|---|---|---|
| 246 | 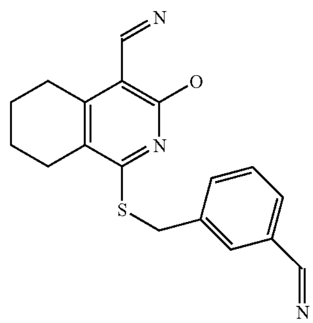 | 324 | 7.82(1 H, br. s.), 7.74 (1 H, d, J = 8.25 Hz), 7.59(1 H, d, J = 7.70 Hz), 7.46(1 H, t, J = 7.97 Hz), 4.53(2 H, s), 4.46(2 H, s), 3.90 (2 H, t, J = 5.77 Hz), 2.85(2 H, t, J = 5.50 Hz) | 97 |
| 247 | 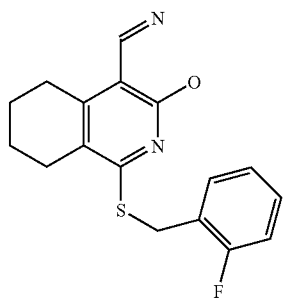 | 317 | 7.45-7.55(1 H, m), 7.24-7.33(1 H, m), 7.03-7.15(2 H, m), 4.54(2 H, s), 4.45(2 H, s), 3.91(2 H, t, J = 5.68 Hz), 2.87(2 H, t, J = 5.68 Hz) | 99 |
| 248 | 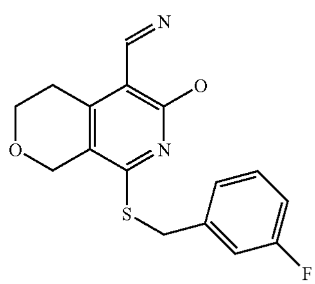 | 317 | 7.27-7.37(1 H, m), 4.52(2 H, s), 3.92(2 H, t, J = 5.50 Hz), 2.88 (2 H, t, J = 5.50 Hz) | 99 |
| 249 | 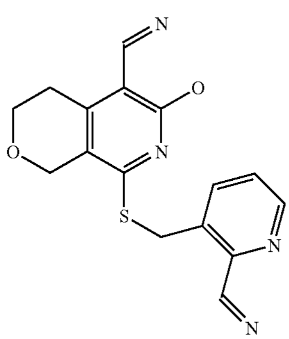 | 325 | 8.57(1 H, t, J = 3.85 Hz), 8.16(1 H, d, J = 8.25 Hz), 7.58(1 H, dd, J = 8.25, 4.95 Hz), 4.70(2 H, s), 4.48(2 H, s), 3.91(2 H, t, J = 5.50 Hz), 2.86(2 H, t, J = 5.50 Hz) | 99 |
| 250 | 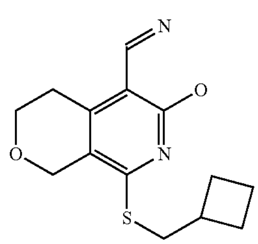 | 277 | 4.39(2 H, s), 3.82(2 H, t, J = 5.68 Hz), 3.22 (2 H, s), 2.77(2 H, t, J = 5.68 Hz), 2.52(1 H, ddd, J = 15.54, 7.96, 7.83 Hz), 1.93-2.07 (2 H, m), 1.78(4 H, dq, J = 16.93, 8.34 Hz) | 98 |

TABLE 6-continued

| Example | Structure | MS (M + H) | NMR | Purity |
|---|---|---|---|---|
| 251 | 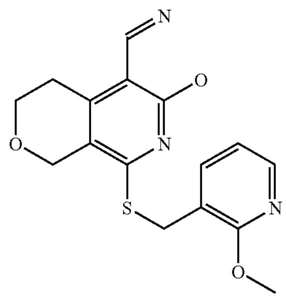 | 330 | 8.01(1 H, d, J = 4.95 Hz), 7.74-7.83(1 H, m), 6.83-6.89(1 H, m), 4.42(3 H, br. s.), 3.95(2 H, s), 3.88(2 H, t, J = 5.77 Hz), 2.84 (2 H, t, J = 5.77 Hz). One 2 H singlet is hidden under solvent peak | 98 |

Example 252

1-(2-Chlorophenylthio)-3-hydroxy-5,6,7,8-tetrahydroisoquinoline-4-carbonitrile

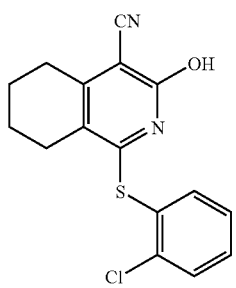

Step 1: 1-(2-Chlorobenzylsulfonyl)-3-hydroxy-5,6,7,8-tetrahydroisoquinoline-4-carbonitrile

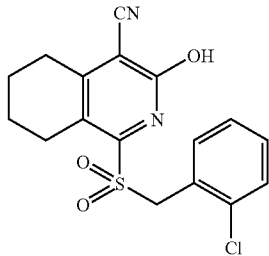

To a solution of Example 1 (150 mg, 0.45 mmol) was added MCPBA (230 mg, 1.36 mmol) in DCM (20 mL) was stirred for 5 h. After this time, the solvent was removed under vacuum to yield a residue. The residue was purified by preparative HPLC (Gradient Solvent System: From 30% A: 70% B to 0% A: 100% B; [A=10% MeOH/90% H$_2$O+0.1% TFA]; [B=90% MeOH/10% H$_2$O+0.1% TFA]; detection at 220 nm: 10 min gradient; Phenomenex Luna AXIA 30×100 mm) to provide the title compound as yellow oil (0.12 g, 73%). LC/MS m/z 363 (M+H).

Step 2: Example 252

A mixture of the product above 1-(2-chlorobenzylsulfonyl)-3-hydroxy-5,6,7,8-tetrahydroisoquinoline-4-carbonitrile (10 mg, 0.027 mmol), thiophenol (8 mg, 0.055 mmol), and K$_2$CO$_3$ (8 mg, 0.055 mmol) was heated to 150° C. for 30 min with microwave irradiation. The mixture was filtered. The filtrate was purified by preparative HPLC (Gradient Solvent System: From 40% A: 60% B to 0% A: 100% B; [A=10% MeOH/90% H$_2$O+0.1% TFA]; [B=90% MeOH/10% H$_2$O+ 0.1% TFA]; detection at 220 nm: 10 min gradient; Phenomenex Luna AXIA 30×100 mm) to provide Example 252 as a yellow oil (4 mg, 51%). $^1$H NMR (400 MHz, CD$_3$OD) δ ppm 7.24-7.49 (5H, m), 2.77 (2H, s), 2.41-2.59 (2H, m), 1.72 (4H, d, J=3.30 Hz). LC/MS m/z 283 (M+H).

Example 253

1-(Benzylamino)-7-fluoro-3-hydroxyisoquinoline-4-carbonitrile

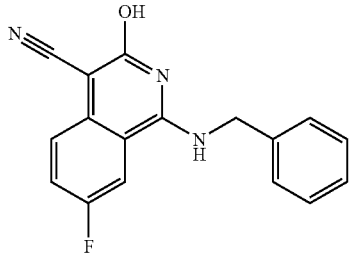

Step 1: 7-Fluoro-3-hydroxy-1-(methylthio)isoquinoline-4-carbonitrile

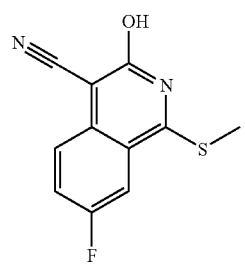

To a 50 mL round bottom flask was added 7-fluoro-3-hydroxy-1-mercaptoisoquinoline-4-carbonitrile (400 mg, 2.27 mmol), DMF (10 mL), NaOH (10 mL, 2 N), followed by iodomethane (322 mg, 2.27 mmol). After stirring for 2 h, the solution was diluted with a solution of citric acid (200 mL, 10% w/v) and extracted with ethyl acetate. The organic layer was washed with brine, dried over Na$_2$SO$_4$ and filtered. The solvent was concentrated to yield 7-fluoro-3-hydroxy-1-(methylthio)isoquinoline-4-carbonitrile (420 mg, 1.79 mmol, 79%) as a pale yellow solid which was suitably clean for the next step. LC/MS m/z 235 [M+H].

Step 2: 7-Fluoro-3-hydroxy-1-(methylsulfonyl)isoquinoline-4-carbonitrile

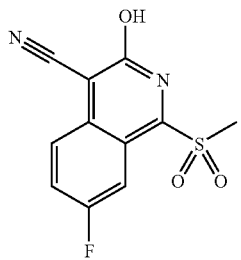

To a 50 mL round bottom flask was added 7-fluoro-3-hydroxy-1-(methylthio)isoquinoline-4-carbonitrile (400 mg, 1.71 mmol), MCPBA (648 mg, 3.76 mmol) and DCM (20 mL). After stirring the solution for 18 h, the mixture was diluted with a solution of citric acid (100 mL, 10% w/v), and extracted with ethyl acetate (2×100 mL). The combined organic layers were washed with brine, dried over $Na_2SO_4$ and filtered. The solvent was concentrated to yield 7-fluoro-3-hydroxy-1-(methylsulfonyl) isoquinoline-4-carbonitrile (364 mg, 1.37 mmol, 80%) as a pale yellow solid. $^1$H NMR (400 MHz, DMSO-$d_6$): δ ppm 8.43 (dd, J=10.11, 2.20 Hz, 1H), 8.09 (dd, J=9.23, 5.27 Hz, 1H), 7.91-8.03 (m, 1H), 3.56 (s, 3H). LC/MS m/z 267 [M+H].

Step 3: Example 253

To a 5 mL microwave reactor vial was added 7-fluoro-3-hydroxy-1-(methylsulfonyl) isoquinoline-4-carbonitrile (110 mg, 0.41 mmol), NMP (5 mL), followed by a large excess of $K_2CO_3$. To the mixture was added benzylamine (133 mg, 1.24 mmol), then capped and heated by microwave irradiation at 160° C. for 30 min. The reaction was then diluted with a solution of citric acid (50 mL, 10% w/v) and extracted with ethyl acetate. The organic layer was washed with brine, dried over $Na_2SO_4$, filtered and concentrated. The resultant crude residue was purified by preparative HPLC (Gradient Solvent System: From 50% A: 50% B to 0% A: 100% B; [A=10% MeOH/90% $H_2O$+0.1% TFA]; [B=90% MeOH/10% $H_2O$+0.1% TFA]; detection at 220 nm: 10 min gradient; Phenomenex Luna AXIA 30×100 mm) to provide Example 253 (17.8 mg, 0.061 mmol, 15%) as a yellow solid. $^1$H NMR (400 MHz, DMSO-$d_6$): δ ppm 11.63 (br. s., 1H), 8.83 (br. s., 1H), 8.10 (d, J=10.55 Hz, 1H), 7.55 (d, J=6.15 Hz, 2H), 7.13-7.39 (m, 5H), 4.73 (d, J=4.83 Hz, 2H). LC/MS m/z 294 [M+H].

Example 254

1-Benzyl-7-fluoro-3-hydroxyisoquinoline-4-carbonitrile

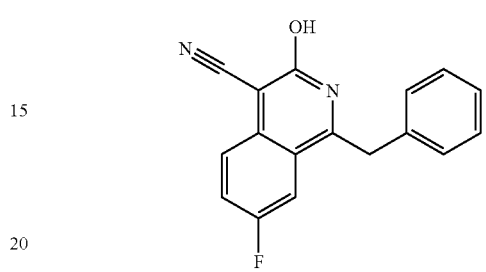

To a 25 mL round bottom flask was added 7-fluoro-3-hydroxy-1-(methylsulfonyl) isoquinoline-4-carbonitrile (150 mg, 0.57 mmol), anhydrous THF (10 mL), then benzylmagnesium chloride (1.71 mL, 1M, 1.71 mmol). The mixture was stirred at room temperature under Ar for 30 min. The reaction was then diluted with a solution of citric acid (75 mL, 10% w/v), and extracted with ethyl acetate. The organic layer was washed with brine, dried over $Na_2SO_4$, filtered and concentrated. The resultant crude residue was purified by preparative HPLC (Gradient Solvent System: From 50% A: 50% B to 0% A: 100% B; [A=10% MeOH/90% $H_2O$+0.1% TFA]; [B=90% MeOH/10% $H_2O$+0.1% TFA]; detection at 220 nm: 10 min gradient; Phenomenex Luna AXIA 30×100 mm) to provide Example 254 (2 mg, 0.0072 mmol, 1.3%) as a yellow solid. $^1$H NMR (400 MHz, methanol-$d_4$): δ 9.25 (dd, J=10.11, 2.20 Hz, 1H), 9.20 (dd, J=9.01, 5.05 Hz, 1H), 8.91-8.97 (m, 1H), 8.55-8.60 (m, 2H), 8.51 (t, J=7.47 Hz, 2H), 8.44 (d, J=7.47 Hz, 1H), 5.85 (s, 2H). LC/MS m/z 279 [M+H].

Examples 255 to 285

Examples 255 to 285 in Table 7 were prepared according to the procedures described in Examples 252 to 254 or by other similar methods known to one skilled in the art, with other appropriate reagent. NMR Spectra data are reported in δ ppm using a 400 MHz spectrometer and $CD_4OD$ as the solvent. In the structures set forth in Table 7, the "—O" attached to the carbon adjacent to the nitrogen in the bicyclic core is used to denote an "—OH" group as indicated in Formula I.

TABLE 7

| Example | Structure | MS (M + H) | NMR | Purity |
|---|---|---|---|---|
| 255 | ![structure] | 317 | 7.18-7.54(4 H, m), 2.77 (2 H, s), 2.53(2 H, br. s.), 1.74(4 H, br. s.) | 98 |

TABLE 7-continued

| Example | Structure | MS (M + H) | NMR | Purity |
|---|---|---|---|---|
| 256 | 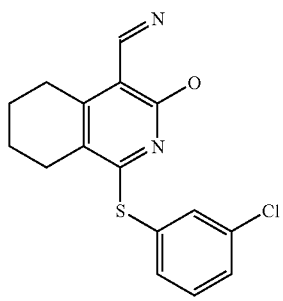 | 317 | 7.40(1 H, s), 7.28-7.34 (3 H, m), 2.77(8 H, d, J = 5.77 Hz), 2.52(2 H, t, J = 5.77 Hz), 1.70-1.77(4 H, m) | 98 |
| 257 | 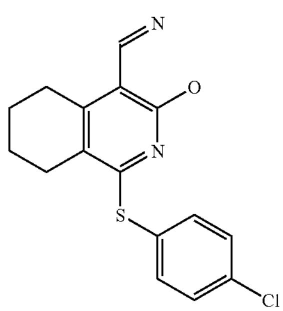 | 317 | 7.33-7.49(4 H, m), 2.81-2.91(2 H, m), 2.52-2.65(2 H, m), 1.73-1.91 (4 H, m) | 98 |
| 258 | 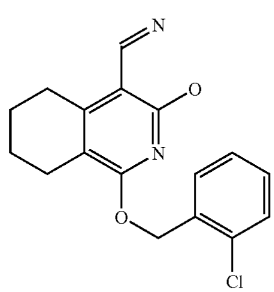 | 315 | 7.50-7.56(1 H, m), 7.39-7.44(1 H, m), 7.28-7.34(2 H, m), 5.47(2 H, s), 2.76(2 H, t, J = 5.22 Hz), 2.54(2 H, t, J = 5.50 Hz), 1.73-1.84(4 H, m) | 96 |
| 259 | 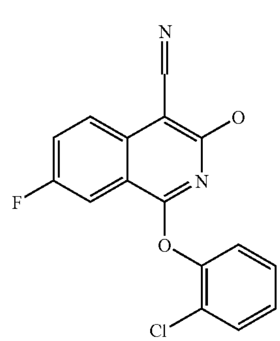 | 316 | 12.66(br. s., 1 H), 8.04 (d, J = 8.25 Hz, 1 H), 7.82 (d, J = 6.60 Hz, 2 H), 7.60 (d, J = 6.60 Hz, 1 H), 7.48-7.52(m, 1 H), 7.44(t, J = 7.15 Hz, 1 H), 7.32(t, J = 7.70 Hz, 1 H) | 99 |

TABLE 7-continued
| Example | Structure | MS (M + H) | NMR | Purity |
|---|---|---|---|---|
| 260 | 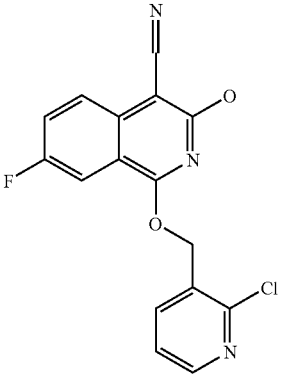 | 331 | 12.75(br. s., 1 H), 8.38 (dd, J = 4.83, 1.76 Hz, 1 H), 8.19(dd, J = 7.69, 1.98 Hz, 1 H), 7.84-7.95(m, 1 H), 7.67-7.81(m, 2 H), 7.46(dd, J = 7.69, 4.61 Hz, 1 H), 5.60(s, 2 H) | 99 |
| 261 | 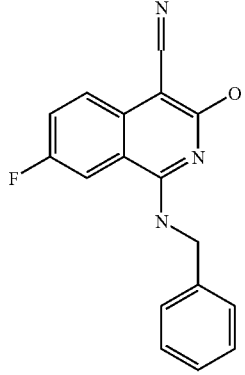 | 294 | 11.63(br. s., 1 H), 8.83 (br. s., 1 H), 8.10(d, J = 10.55 Hz, 1 H), 7.55(d, J = 6.15 Hz, 2 H), 7.13-7.39(m, 5 H), 4.73(d, J = 4.83 Hz, 2 H) | 98 |
| 262 | 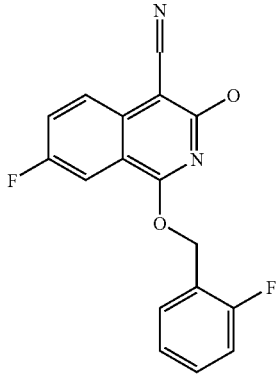 | 313 | 7.94(dd, J = 9.23, 4.83 Hz, 1 H), 7.82(dd, J = 9.01, 2.42 Hz, 1 H), 7.47-7.58 (m, 2 H), 7.34-7.45(m, 1 H), 7.20(t, J = 7.47 Hz, 1 H), 7.15(t, J = 9.23 Hz, 1 H), 5.62(s, 2 H) | 99 |
| 263 | 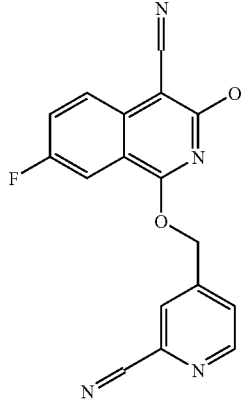 | 307 | 12.84(br. s., 1 H), 8.69 (d, J = 3.08 Hz, 1 H), 8.24 (d, J = 7.47 Hz, 1 H), 8.10 (d, J = 8.35 Hz, 1 H), 7.83-7.97(m, 3 H) | 99 |

TABLE 7-continued

| Example | Structure | MS (M + H) | NMR | Purity |
|---|---|---|---|---|
| 264 | 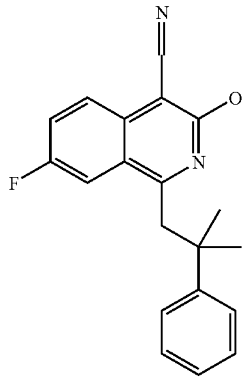 | 321 | 7.82(dd, J = 9.23, 5.27 Hz, 1 H), 7.35-7.46(m, 3 H), 7.25-7.33(m, 2 H), 7.12-7.22(m, 1 H), 6.94 (dd, J = 9.67, 2.20 Hz, 1 H), 3.49(s, 2 H), 1.55(s, 6 H) | 99 |
| 265 | 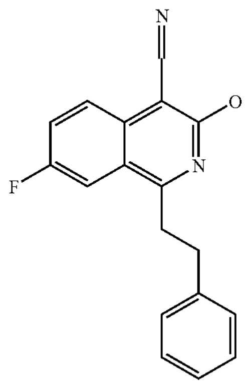 | 293 | 7.93(dd, J = 9.23, 4.83 Hz, 1 H), 7.46-7.60(m, 2 H), 7.25-7.41(m, 4 H), 7.18(t, J = 7.03 Hz, 1 H), 3.45-3.56(m, 2 H), 3.08-3.19(m, 2 H) | 99 |
| 266 | 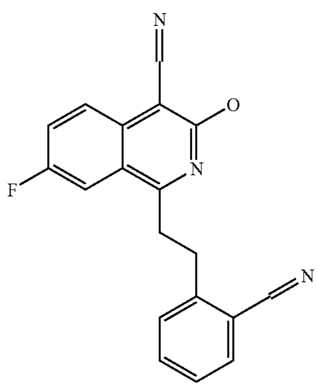 | 320 | 12.82(br. s., 1 H), 7.87-7.93(m, 1 H), 7.86(d, J = 7.47 Hz, 1 H), 7.78-7.82(m, 1 H), 7.69-7.76 (m, 3 H), 7.54(t, J = 7.69 Hz, 1 H), 5.71(s, 2H) | 96 |
| 267 | 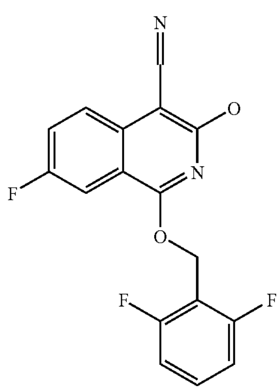 | 331 | | 97 |

TABLE 7-continued

| Example | Structure | MS (M + H) | NMR | Purity |
|---------|-----------|------------|-----|--------|
| 268 | 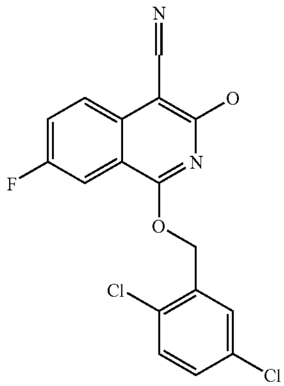 | 364 | | 100 |
| 269 | 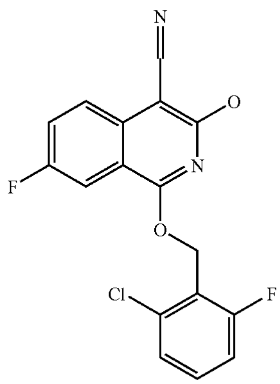 | 348 | | 100 |
| 270 | 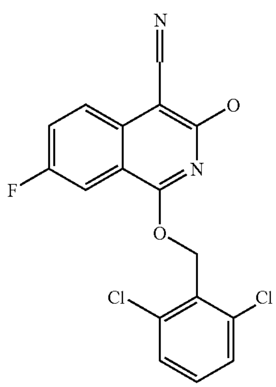 | 364 | | 98 |
| 271 | 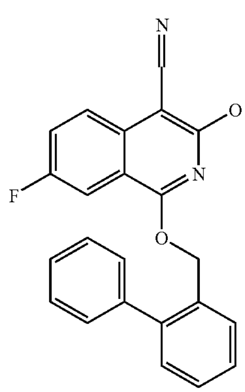 | 371 | | 100 |

TABLE 7-continued
| Example | Structure | MS (M + H) | NMR | Purity |
|---|---|---|---|---|
| 272 | 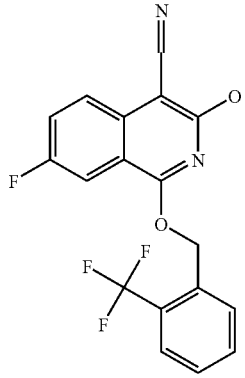 | 363 | | 100 |
| 274 | 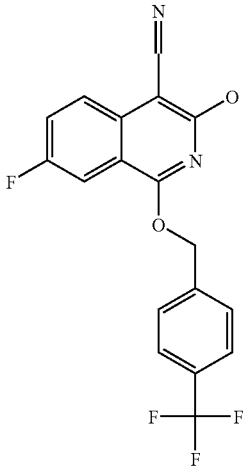 | 363 | | 100 |
| 275 | 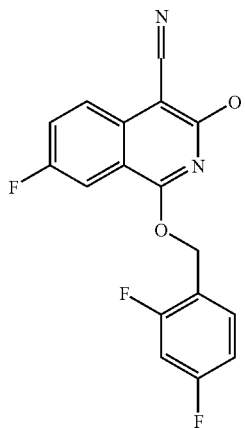 | 331 | | 100 |

TABLE 7-continued

| Example | Structure | MS (M + H) | NMR | Purity |
|---|---|---|---|---|
| 276 | 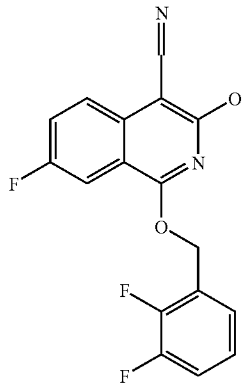 | 331 | | 100 |
| 277 | 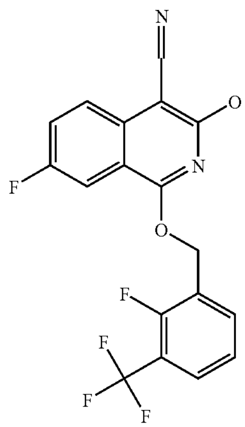 | 381 | | 100 |
| 278 | 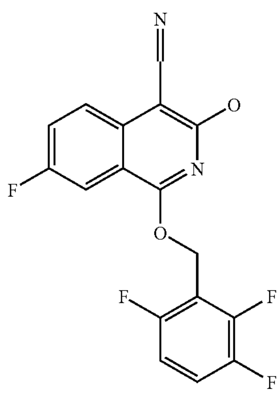 | 349 | | 100 |
| 279 | 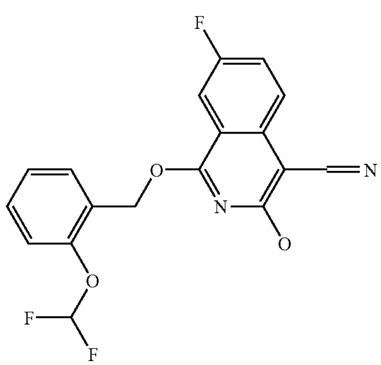 | 361 | | 100 |

TABLE 7-continued

| Example | Structure | MS (M + H) | NMR | Purity |
|---------|-----------|------------|-----|--------|
| 280 | 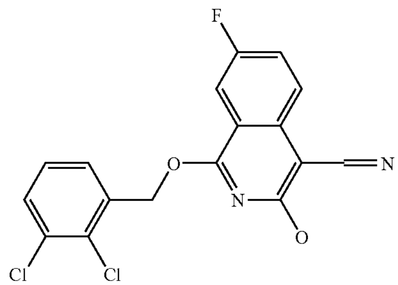 | 364 | | 100 |
| 281 | 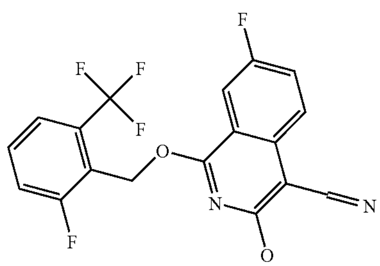 | 381 | | 96 |
| 282 | 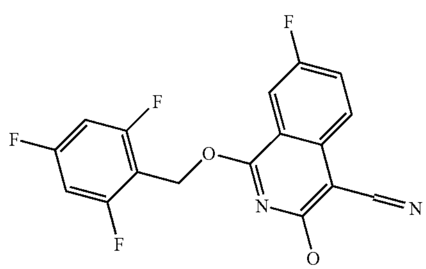 | 349 | | 98 |
| 283 | 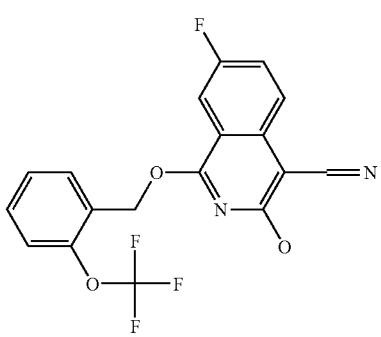 | 379 | | 100 |

TABLE 7-continued

| Example | Structure | MS (M + H) | NMR | Purity |
|---|---|---|---|---|
| 284 | 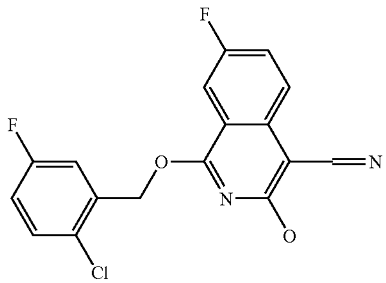 | 348 | | 100 |
| 285 | 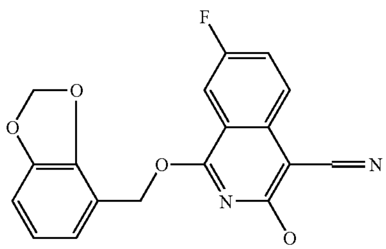 | 339 | | 85 |

Example 286

1-(2-Chlorobenzylthio)-3-methoxy-5,6,7,8-tetrahydroisoquinoline-4-carbonitrile

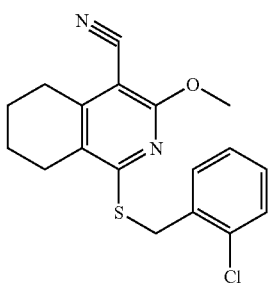

To a solution of Example 1 (18 mg, 0.054 mmol) in 5 mL of Et$_2$O was added 0.36 g of silica gel and trimethylsilyldiazomethane (54 uL, 0.11 mmol). The mixture was stirred for 14 h at rt and filtered. The filtrate was concentrated. The residue was purified by preparative HPLC (Gradient Solvent System: From 20% A: 80% B to 0% A: 100% B; [A=10% MeOH/90% H$_2$O+0.1% TFA]; [B=90% MeOH/10% H$_2$O+ 0.1% TFA]; detection at 220 nm: 10 min gradient; Phenomenex Luna AXIA 30×100 mm) to provide Example 286 (11 mg, 55%) as a white solid. $^1$H NMR (400 MHz, CD$_3$OD) δ ppm 7.49-7.55 (1H, m), 7.40 (1H, d, J=9.34 Hz), 7.24 (2H, d, J=4.95 Hz), 4.64 (2H, s), 3.98 (3H, s), 2.81 (2H, t, J=5.50 Hz), 2.49 (2H, t, J=5.77 Hz), 1.81 (4H, d, J=5.50 Hz). LC/MS m/z 345 (M+H).

Example 287

1-(2-Chlorobenzylthio)-2-methyl-3-oxo-2,3,5,6,7,8-hexahydroisoquinoline-4-carbonitrile

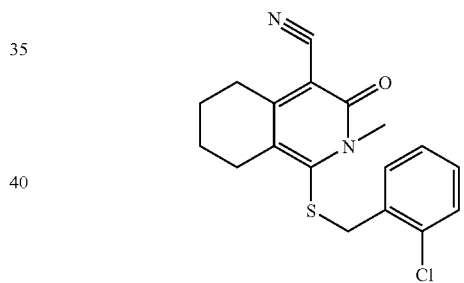

To a solution of Example 1 (20 mg, 0.060 mmol) in 3 mL of THF was added bromomethyl)chlorodimethylsilane (24 mg, 0.13 mmol) and Et$_3$N (13 mg, 0.13 mmol). The solution was stirred at 100° C. with microwave irradiation. To the resulting solution was added CsF (16 mg, 0.11 mmol) and 2 mL of CH$_3$CN followed by 5 drops of water. The mixture was stirred for 24 h at rt. The mixture was extracted with ethyl acetate. The organic layers were dried and concentrated. The residue was purified silica gel (EtOAc/Hex, 3/7) provided Example 287. $^1$H NMR (500 MHz, CD$_3$OD) δ ppm 7.31 (1H, d, J=7.15 Hz), 7.19 (1H, d, J=7.42 Hz), 7.11 (1H, t, J=7.42 Hz), 7.01 (1H, d, J=7.70 Hz), 4.12 (2H, s), 3.22 (3H, s), 2.72 (2H, t, J=6.60 Hz), 2.43 (2H, t, J=6.32 Hz), 1.52-1.62 (2H, m), 1.39-1.49 (2H, m).
LC/MS m/z 345 (M+H).

Examples 288 and 289

Examples 288 and 289 in Table 8 were prepared according to the procedures described in Example 287 or by other similar methods known to one skilled in the art, with other appropriate reagent. NMR Spectra data are reported in δ ppm using a 400 MHz spectrometer and CD$_3$OD as the solvent.

TABLE 8

| Example | Structure | MS (M + H) | NMR | Purity |
|---|---|---|---|---|
| 288 | 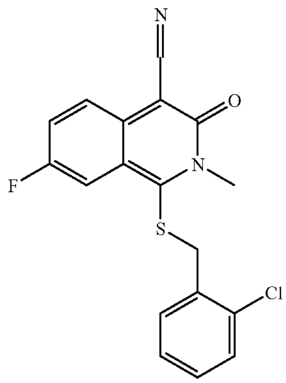 | 360 | 7.68-7.79(m, 2 H), 7.29-7.39(m, 2 H), 7.20(t, J = 7.15 Hz, 1 H), 7.08(t, J = 7.42 Hz, 1 H), 6.82(d, J = 6.05 Hz, 1 H), 4.27(s, 2 H), 3.99(s, 3 H) | 99 |
| 289 | 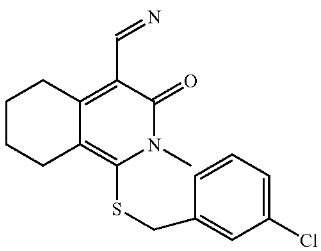 | 345.00 | 7.04-7.09(2 H, m), 6.91 (1 H, s), 6.84-6.89(1 H, m), 3.88(2 H, s), 3.59(3 H, s), 2.63(2 H, t, J = 6.57 Hz), 2.33(2 H, t, J = 6.44 Hz), 1.45-1.54(3 H, m), 1.34-1.44(3 H, m) | 97 |

Example 290

1-(2-Chlorobenzylthio)-4-phenyl-5,6,7,8-tetrahydroisoquinolin-3-ol

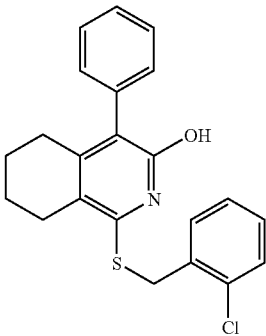

Step 1: 1-(2-Chlorobenzylthio)-4-iodo-5,6,7,8-tetrahydroisoquinolin-3-ol

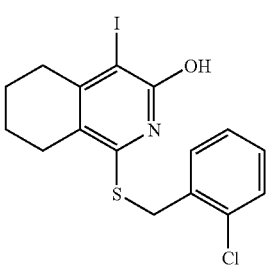

To a solution of Example 2 (0.5 g, 1.6 mmol) in 5 mL of DCM and 1 mL of methanol was added N-iodosuccinimide (0.44 g, 1.9 mmol). The solution was stirred for 1 h at rt and concentrated. The residue was purified by silica gel (EtOAc/Hex, ¼) to provide title compound (0.18 g, 25%). LC/MS m/z 432 (M+H).

Step 2: Example 290

To a solution of 1-(2-chlorobenzylthio)-4-iodo-5,6,7,8-tetrahydroisoquinolin-3-ol (30 mg, 0.069 mmol) in 10 mL of ethanol was added phenyl boronic acid (13 mg, 0.1 mmol), (PPh$_3$)$_4$Pd (60 mg, 0.052 mmol), and K$_2$CO$_3$ (14 mg, 0.1 mmol). The mixture was stirred for 8 h at 110° C. and cooled to rt, filtered. The filtrate was concentrate. The residue was purified by preparative HPLC (Gradient Solvent System: From 30% A: 70% B to 0% A: 100% B; [A=10% MeOH/90% H$_2$O+0.1% TFA]; [B=90% MeOH/10% H$_2$O+0.1% TFA]; detection at 220 nm: 10 min gradient; Phenomenex Luna AXIA 30×100 mm) to provide Example 290 (15 mg, 57%) as a white solid. $^1$H NMR (400 MHz, CDCl$_3$) δ ppm 7.03-7.42 (9H, m), 4.32 (2H, s), 2.47 (2H, t, J=6.32 Hz), 2.32 (2H, t, J=6.32 Hz), 1.52-1.61 (2H, m), 1.40-1.53 (2H, m). LC/MS m/z 382 (M+H).

Examples 291 to 293

Examples 291 to 293 in Table 9 were prepared according to the procedures described in Example 290 or by other similar methods known to one skilled in the art, with other appropriate reagent. NMR Spectra data are reported in δ ppm using a 400 MHz spectrometer and CDCl$_3$ as the solvent. In the structures set forth in Table 9, the "—O" attached to the carbon adjacent to the nitrogen in the bicyclic core is used to denote an "—OH" group as indicated in Formula I.

TABLE 9

| Example | Structure | MS (M + H) | NMR | Purity |
|---|---|---|---|---|
| 291 | *(structure)* | 406.94 | 7.55(2 H, d, J = 8.34 Hz), 7.23-7.35(3 H, m), 7.01-7.20(3 H, m), 4.27(2 H, s), 2.41(2 H, t, J = 6.44 Hz), 2.24(2 H, t, J = 6.32 Hz), 1.50-1.60(2 H, m), 1.38-1.49(2 H, m) | 95.0 |
| 292 | *(structure)* | 406.94 | 7.85(1 H, d, J = 7.83 Hz), 7.71-7.79(1 H, m), 7.51-7.59(1 H, m), 7.37-7.45(2 H, m), 7.32(1 H, d, J = 2.78 Hz), 7.19-7.28(2 H, m), 4.45(2 H, q, J = 13.31 Hz), 2.12-2.52(4 H, m), 1.50-1.65(4 H, m) | 97.0 |
| 293 | *(structure)* | 406.94 | 7.61(1 H, d, J = 7.70 Hz), 7.50(2 H, d, J = 7.70 Hz), 7.43(1 H, d, J = 8.24 Hz), 7.29(2 H, d, J = 7.15 Hz), 7.07-7.18(3 H, m), 4.35(2 H, br. s.), 2.34(2 H, t, J = 6.05 Hz), 2.23(2 H, t, J = 6.32 Hz), 1.47(4 H, br. s.) | 98.0 |

Assay(s) for 11-Beta-Hydroxysteroid Dehydrogenase Activity

The in vitro inhibition of recombinant human 11beta-HSD1 was determined as follows.

Recombinant human 11beta-HSD1 was expressed stably in HEK 293 EBNA cells. Cells were grown in DMEM (high glucose) containing MEM non-essential amino acids, L-glutamine, hygromycine B (200 ug/ml), and G418(200 ug/ml). The cell pellets were homogenized, and the microsomal fraction was obtained by differential centrifugation. 11beta-HSD1 over expressed microsomes were used as the enzyme source for the Scintillation Proximity Assay (SPA). The test compounds at the desired concentration were incubated at room temperature with 12.5 µg of microsomal enzyme, 250 nM [$^3$H]-cortisone, 500 µM NADPH, 50 mM MES, pH 6.5, and 5 mM EDTA in 96-well OptiPlates. The reaction was terminated with the addition of 1 mM 18β- glycerrhentic acid. SPA reagent mixture (YSi anti-rabbit IgG, anti-cortisol antibody in 50 mM Tris, pH 8.0 containing 1% CHAPS and 1% glycerol) was added and the reaction was further incubated at room temperature over night and counted in TopCount. The IC$_{50}$ (concentration of compound required for 50% inhibition of cortisol formation) was determined using XLfit.

Compounds of the present invention were tested in the assay described immediately above and the results shown in Table 10 below were obtained. In the structures set forth in Table 10, the "—O" attached to the carbon adjacent to the nitrogen in the bicyclic core is used to denote an "—OH" group as indicated in Formula I. Similarly, in the structures set forth in Table 10, the "N" adjacent to the carbon atom substituted with =O in the bicyclic or tricyclic core is used to denote an "NH" moiety as indicated in Formula I-t.

TABLE 10

| Example | Structure | IC$_{50}$ (nM) |
|---------|-----------|----------------|
| 1 | 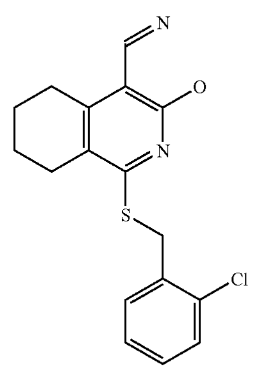 | 2.95 |
| 3 | 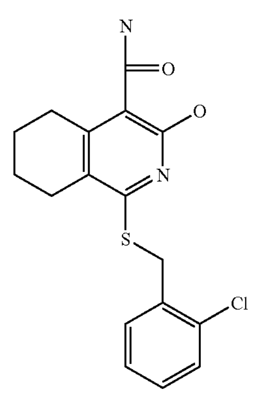 | >10000.00 |
| 6 | 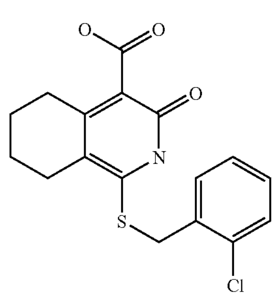 | 470.00 |

TABLE 10-continued

| Example | Structure | IC$_{50}$ (nM) |
|---------|-----------|----------------|
| 12 | 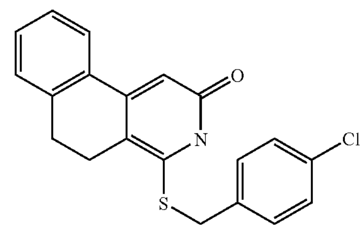 | 948.30 |
| 17 | 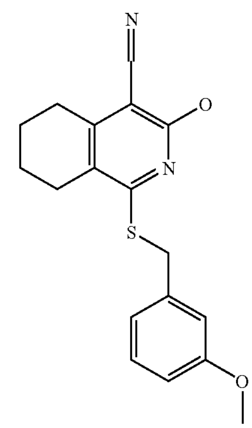 | 461.40 |
| 25 | 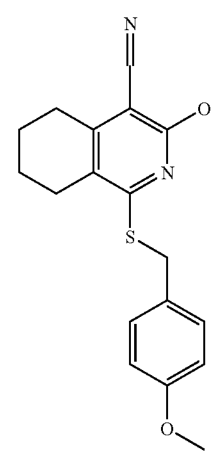 | 466.60 |
| 29 | 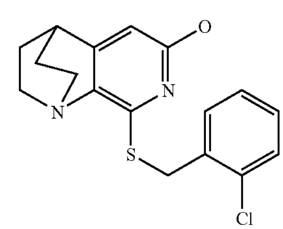 | >10000.00 |
| 32 | 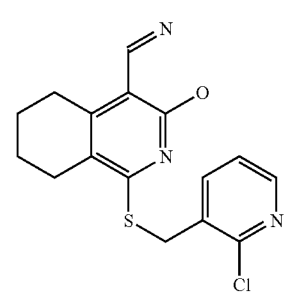 | 2.73 |

TABLE 10-continued

| Example | Structure | IC$_{50}$ (nM) |
|---------|-----------|----------------|
| 34 | 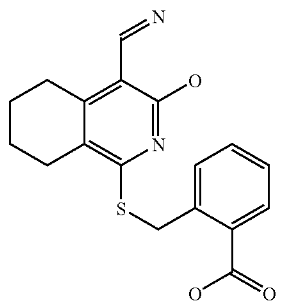 | >10000.00 |
| 35 | 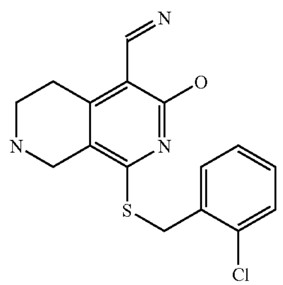 | 460.20 |
| 77 | 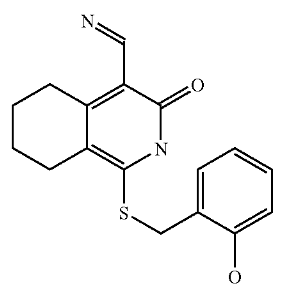 | 407.20 |
| 109 | 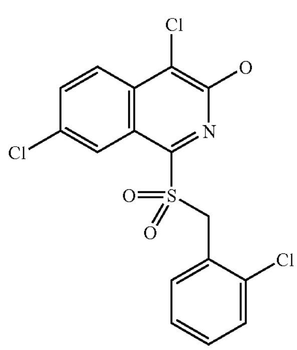 | 671.30 |
| 115 | 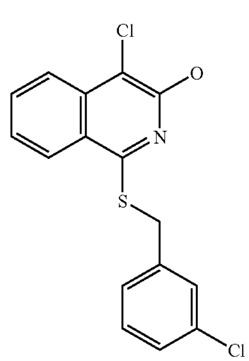 | 780.20 |

TABLE 10-continued

| Example | Structure | IC$_{50}$ (nM) |
|---------|-----------|----------------|
| 116 | 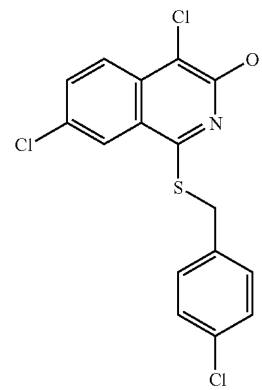 | 715.60 |
| 118 | 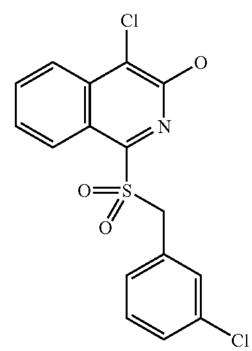 | 530.40 |
| 130 | 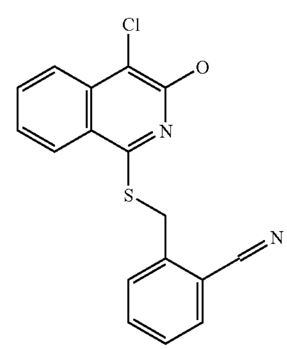 | 2.70 |
| 132 | 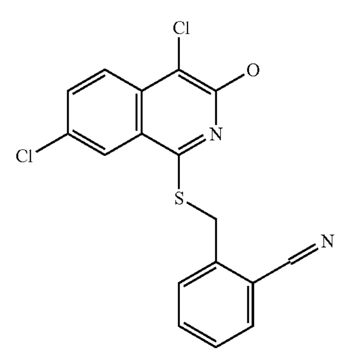 | 2.26 |

TABLE 10-continued

| Example | Structure | IC$_{50}$ (nM) |
|---|---|---|
| 138 | 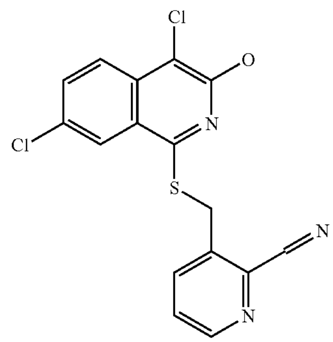 | 2.02 |
| 146 | 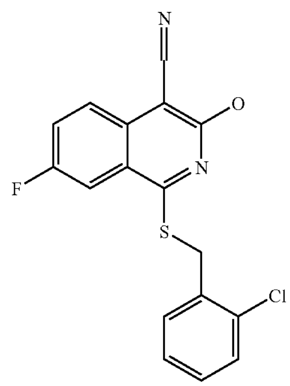 | 2.39 |
| 153 | 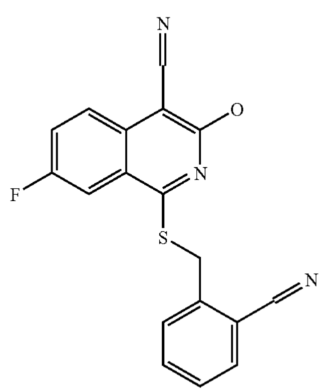 | 1.45 |
| 164 | 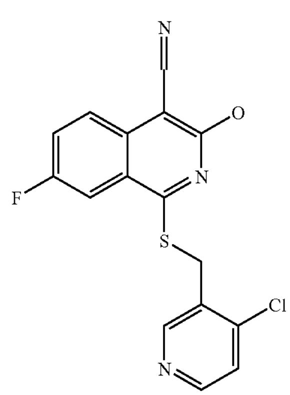 | 2.73 |
| 167 | | 2.87 |
| 167 | | 3.08 |
| 170 | | 1.49 |
| 175 | | 2.58 |

TABLE 10-continued

| Example | Structure | IC$_{50}$ (nM) |
|---|---|---|
| 181 | 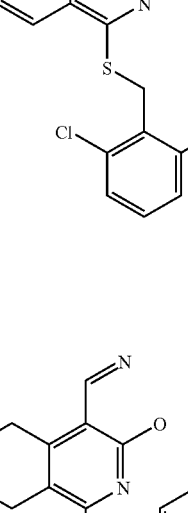 | 3.00 |
| 215 | 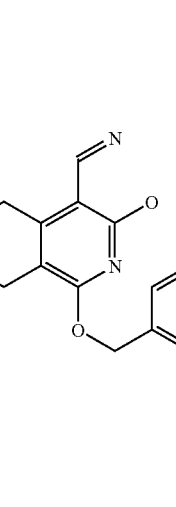 | 1.67 |
| 256 | 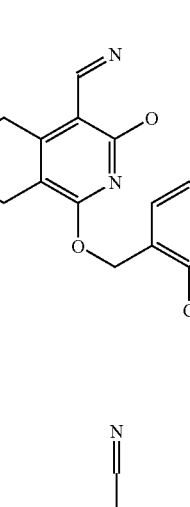 | 2.61 |
| 262 | 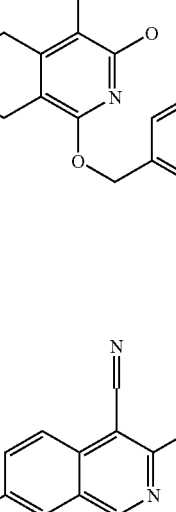 | 335.30 |
| 263 | 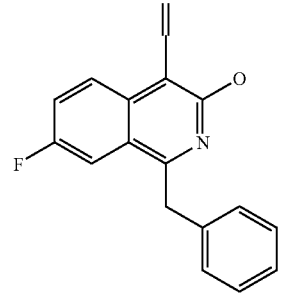 | 406.00 |
| 292 | 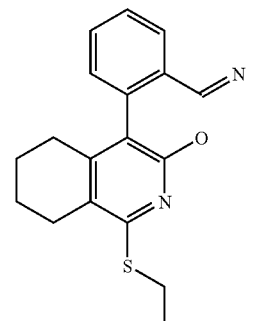 | 288.50 |

Utilities and Combinations

A. Utilities

The compounds of the present invention possess activity as inhibitors of the enzyme 11-beta-hydroxysteroid dehydrogenase type I, and, therefore, may be used in the treatment of diseases associated with 11-beta-hydroxysteroid dehydrogenase type I activity. Via the inhibition of 11-beta-hydroxysteroid dehydrogenase type I, the compounds of the present invention may preferably be employed to inhibit or modulate glucocorticoid production, thereby interrupting or modulating cortisone or cortisol production.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, insulin resistance, hyperinsulinemia, retinopathy, neuropathy, nephropathy, delayed wound healing, atherosclerosis and its sequelae (acute coronary syndrome, myocardial infarction, angina pectoris, peripheral vascular disease, intermitant claudication), abnormal heart function, myocardial ischemia, stroke, Metabolic Syndrome, hypertension, obesity, dislipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, glaucoma and inflammatory diseases, such as, rheumatoid arthritis, Cushing's Disease, Alzheimer's Disease and osteoarthritis.

Metabolic Syndrome or "Syndrome X" is described in Ford et al., *J. Am. Med. Assoc.*, 287:356-359 (2002) and Arbeeny et al., *Curr. Med. Chem.—Imm., Endoc. & Metab. Agents*, 1:1-24 (2001).

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other 11-beta-hydroxysteroid dehydrogenase type I inhibitors or one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dislipidemic agents, anti-dylsipidemic agents, anti-hyperlipidemic agents, anti-hypertriglyceridemic agents, anti-hypercholesterolemic agents, anti-restenotic agents, anti-pancreatic agents, lipid lowering agents, appetite suppressants, memory enhancing agents, cognition promoting agents and anti-inflammatory agents.

Examples of suitable anti-diabetic agents for use in combination with the compounds of the present invention include insulin and insulin analogs: LysPro insulin, inhaled formulations comprising insulin; glucagon-like peptides; sulfonylureas and analogs: chlorpropamide, glibenclamide, tolbutamide, tolazamide, acetohexamide, glypizide, glyburide, glimepiride, repaglinide, meglitinide; biguanides: metformin, phenformin, buformin; alpha2-antagonists and imidazolines: midaglizole, isaglidole, deriglidole, idazoxan, efaroxan, fluparoxan; other insulin secretagogues: linogliride, insulinotropin, exendin-4, BTS-67582, A-4166; thiazolidinediones: ciglitazone, pioglitazone, troglitazone, rosiglitazone; PPAR-gamma agonists; PPAR-alpha agonists; PPAR alpha/gamma dual agonists; SGLT2 inhibitors; dipeptidyl peptidase-IV (DPP4) inhibitors; glucagon-like peptide-1 (GLP-1) receptor agonists; aldose reductase inhibitors; RXR agonists: JTT-501, MCC-555, MX-6054, DRF2593, GI-262570, KRP-297, LG100268; fatty acid oxidation inhibitors: clomoxir, etomoxir; α-glucosidase inhibitors: precose, acarbose, miglitol, emiglitate, voglibose, MDL-25,637, camiglibose, MDL-73,945; beta-agonists: BRL 35135, BRL 37344, Ro 16-8714, ICI D7114, CL 316,243, TAK-667, AZ40140; phosphodiesterase inhibitors, both cAMP and cGMP type: sildenafil, L686398: L-386,398; amylin antagonists: pramlintide, AC-137; lipoxygenase inhibitors: masoprocal; somatostatin analogs: BM-23014, seglitide, octreotide; glucagon antagonists: BAY 276-9955; insulin signaling agonists, insulin mimetics, PTP1B inhibitors: L-783281, TER17411, TER17529; gluconeogenesis inhibitors: GP3034; somatostatin analogs and antagonists; antilipolytic agents: nicotinic acid, acipimox, WAG 994; glucose transport stimulating agents: BM-130795; glucose synthase kinase inhibitors: lithium chloride, CT98014, CT98023; and galanin receptor agonists.

Other suitable thiazolidinediones include Mitsubishi's MCC-555 (disclosed in U.S. Pat. No. 5,594,016), Glaxo-Wellcome's GL-262570, englitazone (CP-68722, Pfizer), or darglitazone (CP-86325, Pfizer, isaglitazone (MIT/J&J), JTT-501 (JPNT/P&U), L-895645 (Merck), R-119702 (Sankyo/W L), N,N-2344 (Dr. Reddy/N N), or YM-440 (Yamanouchi).

Suitable PPAR alpha/gamma dual agonists include AR-HO39242 (Astra/Zeneca), GW-409544 (Glaxo-Wellcome), KRP297 (Kyorin Merck), as well as those disclosed by Murakami et al, "A Novel Insulin Sensitizer Acts As a Coligand for Peroxisome Proliferation—Activated Receptor Alpha (PPAR alpha) and PPAR gamma; Effect of PPAR alpha Activation on Abnormal Lipid Metabolism in Liver of Zucker Fatty Rats", *Diabetes*, 47:1841-1847 (1998), and WO 01/21602, the disclosure of which is incorporated herein by reference, employing dosages as set out therein, which compounds designated as preferred are preferred for use herein.

Suitable alpha2 antagonists also include those disclosed in WO 00/59506, employing dosages as set out herein.

Suitable SGLT2 inhibitors include T-1095, phlorizin, WAY-123783, and those described in WO 01/27128.

Suitable DPP4 inhibitors include saxagliptan, sitagliptan, vildagliptan, and denagliptan.

Suitable aldose reductase inhibitors include those disclosed in WO 99/26659.

Suitable meglitinides include nateglinide (Novartis) or KAD1229 (PF/Kissei).

Examples of glucagon-like peptide-1 (GLP-1) receptor agonists include Exenatide (Byetta™), NN2211 (Liraglutide, Novo Nordisk), AVE0010 (Sanofi-Aventis), R1583 (Roche/Ipsen), SUN E7001 (Daiichi/Santory), GSK-716155 (GSK/Human Genome Sciences) and Exendin-4 (PC-DAC™).

Other anti-diabetic agents that can be used in combination with compounds of the invention include ergoset and D-chiroinositol.

Suitable anti-ischemic agents include, but are not limited to, those described in the Physician's Desk Reference and NHE inhibitors, including those disclosed in WO 99/43663.

Examples of suitable lipid lowering agents for use in combination with the compounds of the present invention include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal Na$^+$/bile acid cotransporter inhibitors, upregulators of LDL receptor activity, bile acid sequestrants, cholesterol ester transfer protein inhibitors (e.g., CP-529414 (Pfizer)), and/or nicotinic acid and derivatives thereof.

MTP inhibitors which may be employed as described above include those disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885, 983, and U.S. Pat. No. 5,962,440.

The HMG CoA reductase inhibitors which may be employed in combination with one or more compounds of formula I include mevastatin and related compounds, as disclosed in U.S. Pat. No. 3,983,140, lovastatin, (mevinolin) and related compounds, as disclosed in U.S. Pat. No. 4,231,938, pravastatin, and related compounds, such as disclosed in U.S. Pat. No. 4,346,227, simvastatin, and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772; cerivastatin, as disclosed in U.S. Pat. Nos. 5,006,530 and 5,177,080; atorvastatin, as disclosed in U.S. Pat. Nos. 4,681,893, 5,273,995, 5,385,929 and 5,686, 104; atavastatin (Nissan/Sankyo's nisvastatin (NK-104)), as disclosed in U.S. Pat. No. 5,011,930; visastatin (Shionogi-Astra/Zeneca (ZD-4522)) as disclosed in U.S. Pat. No. 5,260,440.

Preferred hypolipidemic agents are pravastatin, lovastatin, simvastatin, atorvastatin, fluvastatin, cerivastatin, atavastatin, and ZD-4522.

The fibric acid derivatives which may be employed in combination with one or more compounds of formula I include fenofibrate, gemfibrozil, clofibrate, bezafibrate, ciprofibrate, clinofibrate, and the like, probucol, and related compounds, as disclosed in U.S. Pat. No. 3,674,836, fenofibrate and gemfibrozil being preferred, bile acid sequestrants, such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents.

The ACAT inhibitor which may be employed in combination with one or more compounds of formula I include those disclosed in Drugs of the Future 24:9-15 (1999), (Avasimibe); "The ACAT inhibitor, C1-1011 is effective in the prevention and regression of aortic fatty streak area in hamsters", Nicolosi et al., Atherosclerosis (Shannon, Irel). (1998), 137(1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359-62, or TS-962 (Taisho Pharmaceutical Co. Ltd.).

The hypolipidemic agent may be an upregulator of LDL receptor activity, such as MD-700 (Taisho Pharmaceutical Co. Ltd) and LY295427 (Eli Lilly).

Examples of suitable cholesterol absorption inhibitors for use in combination with the compounds of the invention include ezetimibe (ZetiaoR)

Examples of suitable ileal $Na^+$/bile acid cotransporter inhibitors for use in combination with the compounds of the invention include compounds as disclosed in Drugs of the Future, 24, 425-430 (1999).

The lipoxygenase inhibitors which may be employed in combination with one or more compounds of formula I include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199-1206, and Comicelli et al, "15-Lipoxygenase and its Inhibition: A Novel Therapeutic Target for Vascular Disease", Current Pharmaceutical Design (1999), 5, 11-20.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors (e.g., aliskiren), ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-obesity agents for use in combination with the compounds of the present invention include a cannabinoid receptor 1 antagonist or inverse agonist, a beta 3 adrenergic agonist, a lipase inhibitor, a serotonin (and dopamine) reuptake inhibitor, a thyroid receptor beta drug, and/or an anorectic agent.

Cannabinoid receptor 1 antagonists and inverse agonists which may be optionally employed in combination with compounds of the present invention include rimonabant, SLV 319, CP-945598 (Pfizer), SR-147778 (Sanofi-Aventis), MK0364 (Merck) and those discussed in D. L. Hertzog, Expert Opin. Ther. Patents 2004, 14, 1435-1452.

The beta 3 adrenergic agonists which may be optionally employed in combination with compounds of the present invention include AJ9677 (Takeda/Dainippon), L750355 (Merck), or CP331648 (Pfizer) or other known beta δ agonists, as disclosed in U.S. Pat. Nos. 5,541,204, 5,770,615, 5,491,134, 5,776,983, and 5,488,064, with AJ9677, L750, 355, and CP331648 being preferred.

Examples of lipase inhibitors which may be optionally employed in combination with compounds of the present invention include orlistat or ATL-962 (Alizyme), with orlistat being preferred.

The serotonin (and dopoamine) reuptake inhibitor and/or modulator which may be optionally employed in combination with a compound of formula I may be sibutramine, topiramate (Johnson & Johnson), APD-356 (Arena) or axokine (Regeneron), with sibutramine and APD-356 being preferred.

Examples of thyroid receptor beta compounds which may be optionally employed in combination with compounds of the present invention include thyroid receptor ligands, such as those disclosed in WO 97/21993 (U. Cal SF), WO 99/00353 (KaroBio), and WO 00/039077 (KaroBio), with compounds of the KaroBio applications being preferred.

The anorectic agent which may be optionally employed in combination with compounds of the present invention include dexamphetamine, phentermine, phenylpropanolamine, or mazindol, with dexamphetamine being preferred.

Other compounds that can be used in combination with the compounds of the present invention include CCK receptor agonists (e.g., SR-27895B); MCHR1 antagonist (e.g., GSK 856464); galanin receptor antagonists; MCR-4 antagonists (e.g., HP-228); leptin or mimetics; urocortin mimetics, CRF antagonists, and CRF binding proteins (e.g., RU-486, urocortin).

Further, the compounds of the present invention may be used in combination with HIV protease inhibitors, including but not limited to Reyataz® and Kaletra®.

Examples of suitable memory enhancing agents, anti-dementia agents, or cognition promoting agents for use in combination with the compounds of the present invention include, but are not limited to, donepezil, rivastigmine, galantamine, memantine, tacrine, metrifonate, muscarine, xanomelline, deprenyl and physostigmine.

Examples of suitable anti-inflammatory agents for use in combination with the compounds of the present invention include, but are not limited to, prednisone, acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha, prednisolone, methylprednisolone, dexamethazone, flucatisone, betamethasone, hydrocortisone and beclomethasone.

The aforementioned patents and patent applications are incorporated herein by reference.

The above other therapeutic agents, when employed in combination with the compounds of the present invention may be used, for example, in those amounts indicated in the Physicians' Desk Reference, as in the patents set out above, or as otherwise determined by one of ordinary skill in the art.

The compounds of formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out the method of the invention for treating diabetes and related diseases, a pharmaceutical composition will be employed containing the compounds of formula I, with or without other antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders, and the like. The compounds can be administered to a mammalian patient, including humans, monkeys, dogs, etc. by an oral route, for example, in the form of tablets, capsules, beads, granules or powders. The dose for adults is preferably between 1 and 2,000 mg per day, which can be administered in a single dose or in the form of individual doses from 1-4 times per day.

A typical capsule for oral administration contains compounds of structure I (250 mg), lactose (75 mg), and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

It is noted that the proceeding examples, while illustrative of the present invention, are not in sequential order and some example numbers may be missing.

What is claimed is:
1. A compound of formula (I)

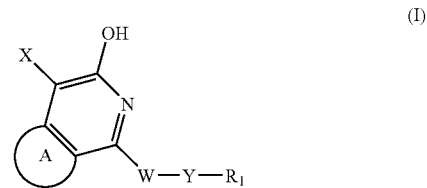

enantiomers, diastereomers, salts, or tautomers thereof wherein:
A is a phenyl, wherein said phenyl may be optionally substituted with one or more $R_4$'s;
X is Cl, cyano, haloalkyl or —$NO_2$;
W is O, S, SO, NH or $SO_2$;
Y is a bond or an alkylene;
$R_1$ is heteroaryl, aryl, or cycloalkyl, all of which may be optionally substituted with one or more $R_{4a}$'s;
$R_4$, at each occurrence, is independently selected from alkyl, aryl, halo, =O, —CN, —$NO_2$, —C(=O)OH, —C(=O)$OR_{10}$, —$OR_{10}$, —OH, —SH, —$SR_{10}$, —C(=O)$NR_9R_9$, —$NR_9R_9$, —S(O)$_2NR_9R_9$, —C(=O)$R_{10}$, —OC(=O)$R_{10}$, —S(=O)$R_{10}$, or —S(O)$_2R_{10}$, wherein the alkyl or aryl may be optionally substituted with one or more $R_5$'s;
$R_{4a}$, at each occurrence, is independently selected from alkyl, aryl, halo, =O, —CN, —$NO_2$, —C(=O)OH, —C(=O)$OR_{10}$, —$OR_{10}$, —OH, —$SR_{10}$, —C(=O)$NR_9R_9$, —$NR_9R_9$, —S(O)$_2NR_9R_9$, —C(=O)$R_{10}$, —OC(=O)$R_{10}$, —S(=O)$R_{10}$, or —S(O)$_2R_{10}$, wherein the alkyl or aryl may be optionally substituted with one or more $R_5$'s;
$R_5$, at each occurrence, is independently selected from alkyl, haloalkyl, aryl, halo, —CN, —C(=O)OH, —C(=O)$OR_{10}$, —$OR_{10}$, —$SR_{10}$, —C(=O)$NR_9R_9$, —$NR_9R_9$, —S(O)$_2NR_9R_9$, —C(=O)$R_{10}$, —OC(=O)$R_{10}$, —S(=O)$R_{10}$, or —S(O)$_2R_{10}$;
$R_9$, at each occurrence, is independently hydrogen, alkyl, aryl, heteroaryl, wherein the heteroaryl contains 1-4 heteroatoms selected from N, O, and S;
$R_{10}$, at each occurrence, is independently selected from alkyl or aryl, wherein the alkyl or aryl may be optionally substituted with 0-3 $R_{10a}$;
$R_{10a}$, at each occurrence, is independently selected from alkyl, aryl, heteroaryl, halo, —C(=O)OH, —C(=O)$OR_{14}$, —$OR_{14}$, —$SR_{14}$, —C(=O)$NR_{14}R_{14}$, —$NR_{14}R_{14}$, —S(O)$_2NR_{14}R_{14}$, —C(=O)$NR_{14}$S(O)$_2R_9$, —S(O)$_2NR_{14}$C(=O)$OR_9$, —S(O)$_2NR_{14}$C(=O)$NR_{14}R_{14}$, —C(=O)$NR_{14}$S(O)$_2CF_3$, —C(=O)$R_{14}$, —$NR_{14}$C(=O)H, —$NR_{14}$C(=O)$R_{14}$, —OC(=O)$R_{14}$, or —S(O)$_2R_{14}$; and
$R_{14}$, at each occurrence, is independently selected from hydrogen, alkyl, or aryl.

2. The compound of claim 1, wherein:

X is Cl or cyano;

W is O or S;

Y is a bond or an alkylene;

$R_1$ is aryl, heteroaryl or cycloalkyl, all of which may be optionally substituted with one or more $R_{4a}$'s;

$R_4$, at each occurrence, is independently selected from alkyl, aryl, halo, =O, —CN, —$NO_2$, —C(=O)OH, —C(=O)$OR_{10}$, —$OR_{10}$, —OH, —$SR_{10}$, —C(=O)$R_{10}$ or —S(O)$_2R_{10}$, wherein the alkyl or aryl may be optionally substituted with one or more $R_5$'s;

$R_{4a}$, at each occurrence, is independently selected from alkyl, aryl, halo, =O, —CN, —$NO_2$, —C(=O)OH, —C(=O)$OR_{10}$, —$OR_{10}$, —OH, —$SR_{10}$, —C(=O)$R_{10}$ or —S(O)$_2R_{10}$, wherein the alkyl or aryl may be optionally substituted with one or more $R_5$'s;

$R_5$, at each occurrence, is independently selected from alkyl, aryl, halo, —CN, —C(=O)OH, —C(=O)$OR_{10}$, —$OR_{10}$, —$SR_{10}$, —C(=O)$R_{10}$, or —S(O)$_2R_{10}$;

$R_{10}$, at each occurrence, is independently selected from alkyl or aryl, wherein the alkyl or aryl may be optionally substituted with 0-3 $R_{10a}$;

$R_{10a}$, at each occurrence, is independently selected from alkyl, aryl, halo, —C(=O)OH, —C(=O)$OR_{14}$, —$OR_{14}$, —$SR_{14}$ or —S(O)$_2R_{14}$; and $R_{14}$, at each occurrence, is independently selected from hydrogen or alkyl.

3. The compound, enantiomers, diastereomers, salts, or tautomers thereof of claim 1, wherein said compound is selected from the group consisting of:

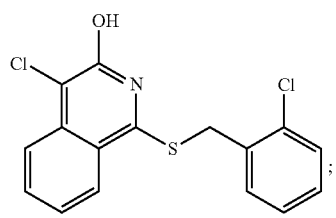

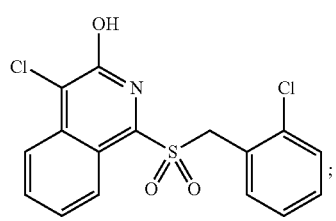

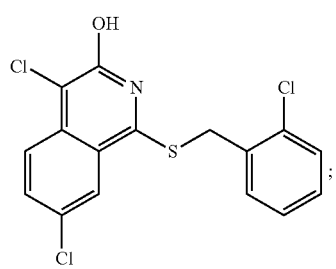

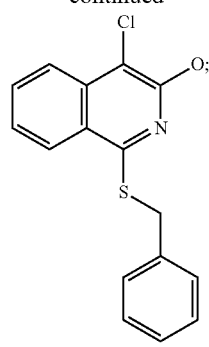

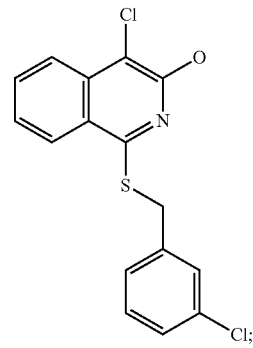

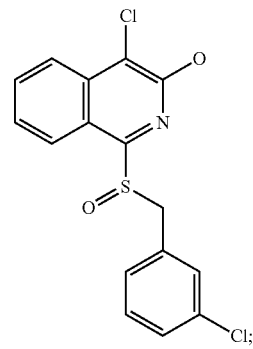

211
-continued
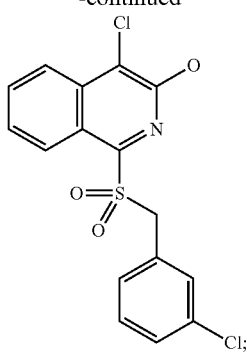
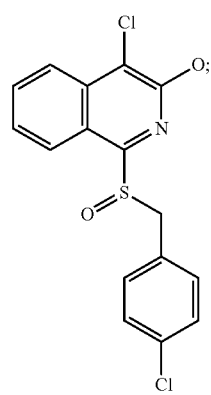
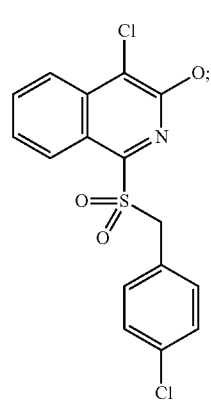
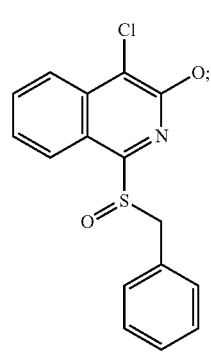
212
-continued
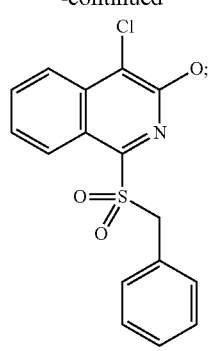
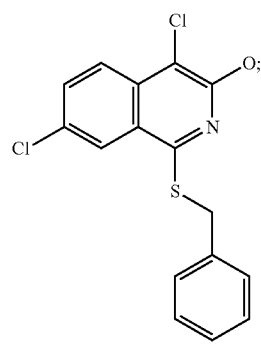
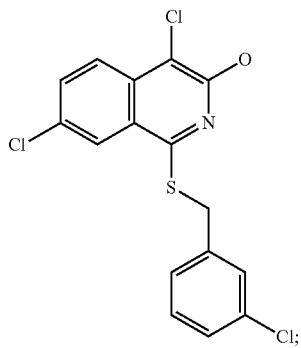
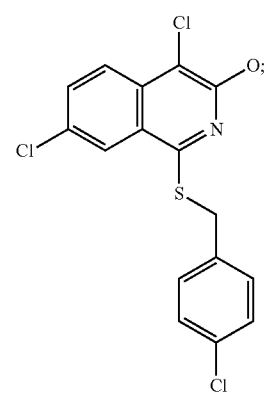

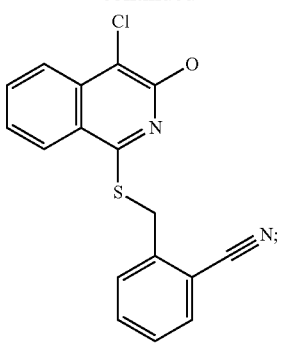
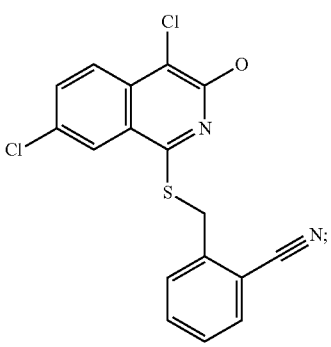
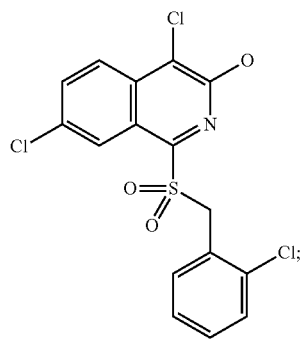
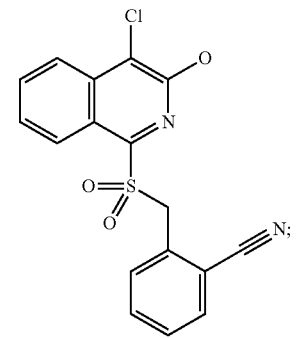
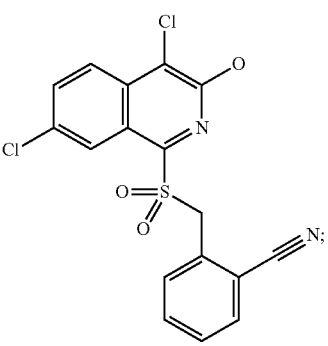
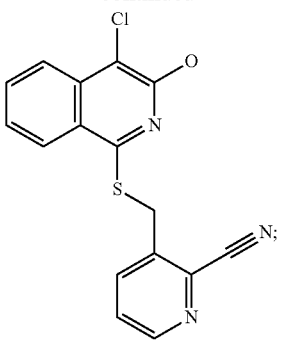
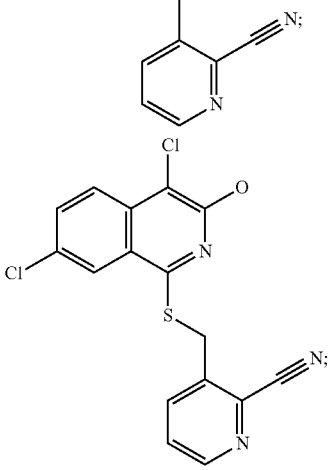
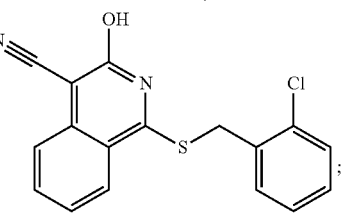
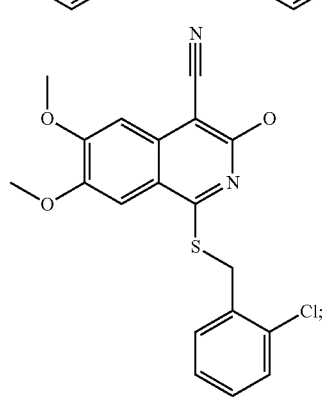
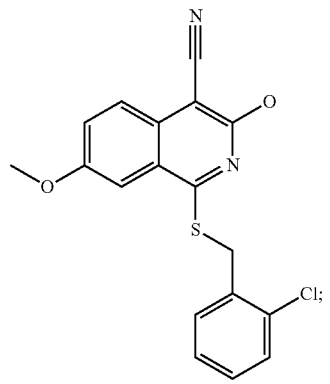

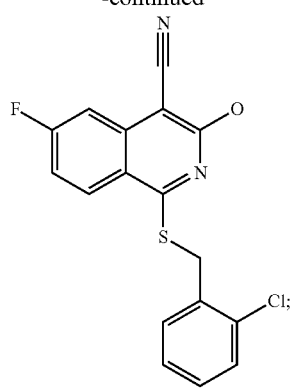
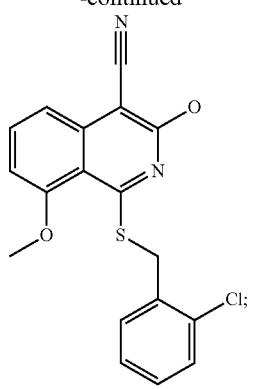
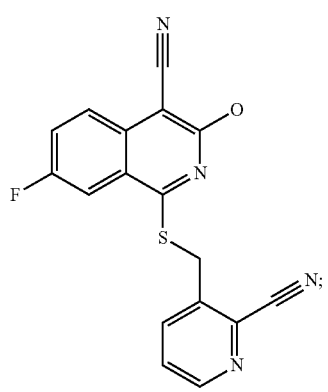

217
-continued
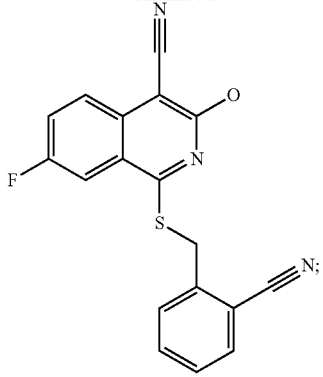
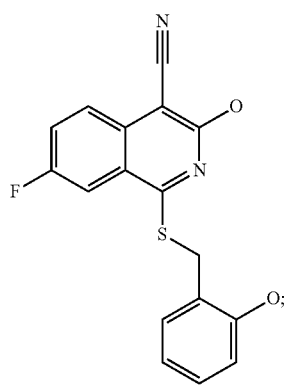
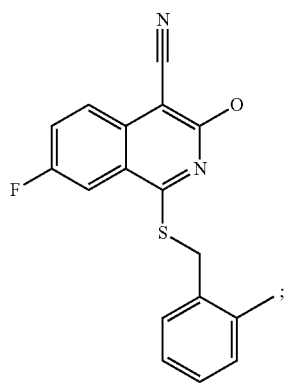
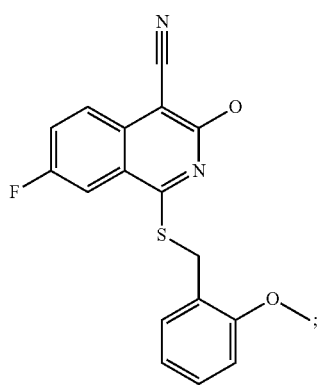
218
-continued
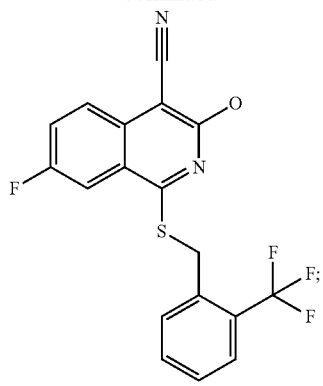
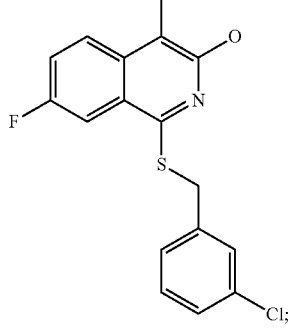
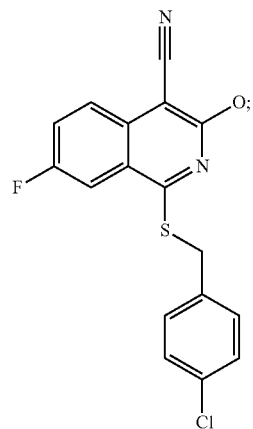
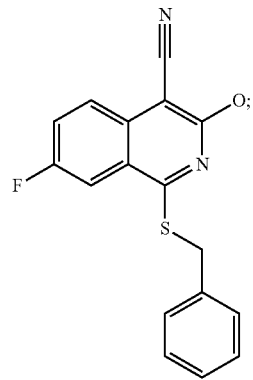

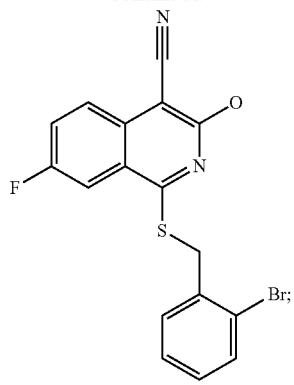
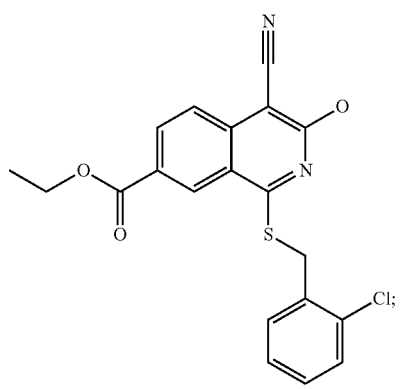
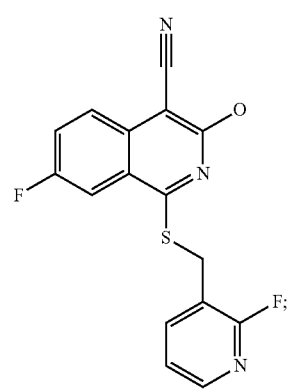
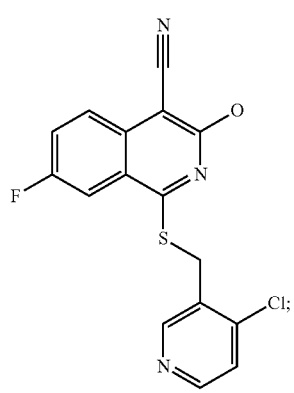
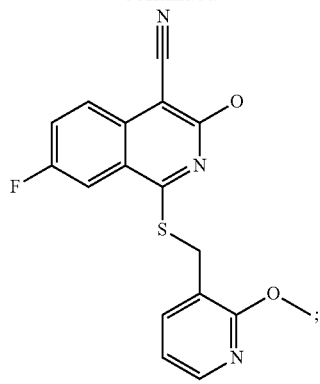
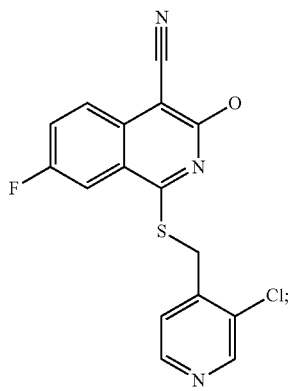
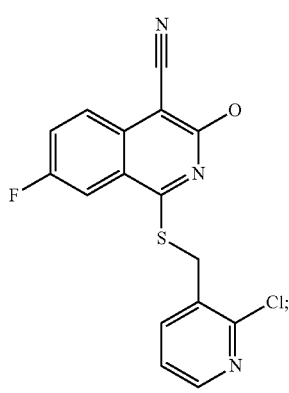
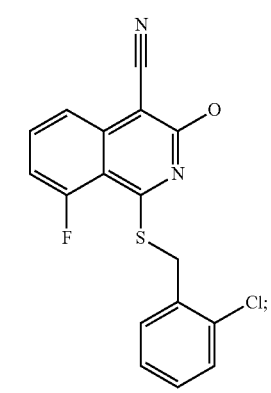

221
-continued
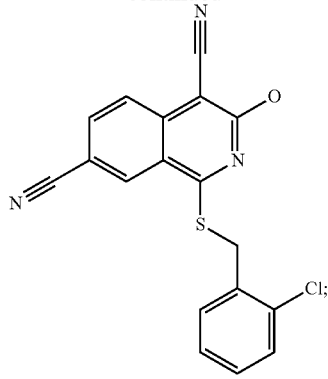
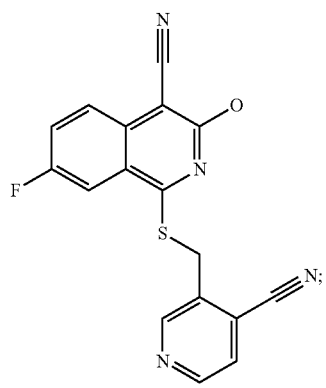
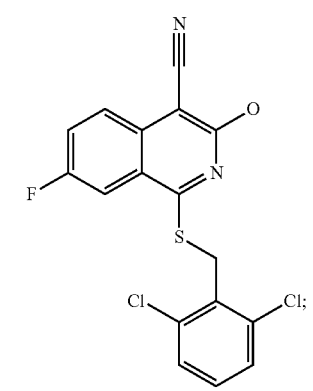
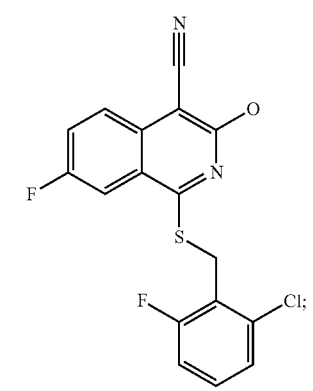
222
-continued
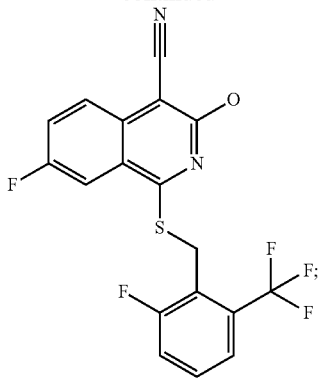
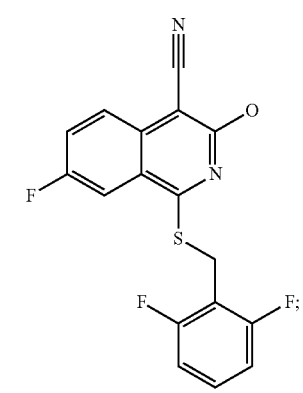
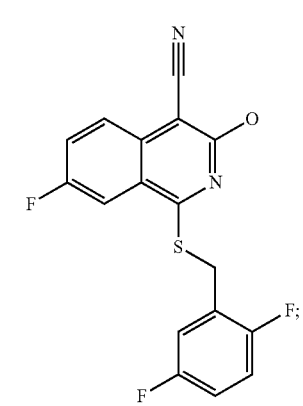
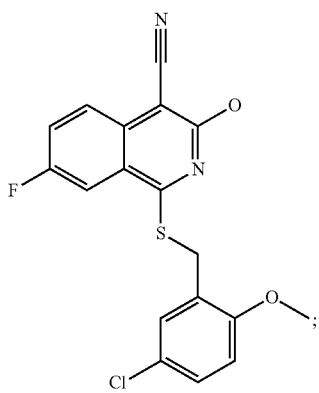

-continued
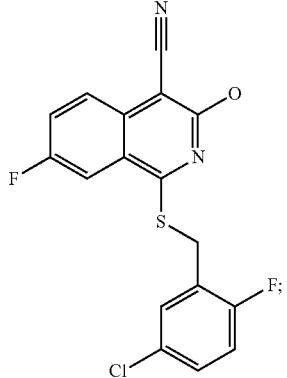
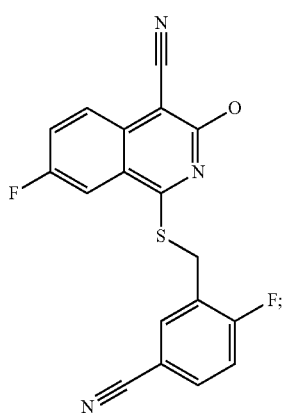
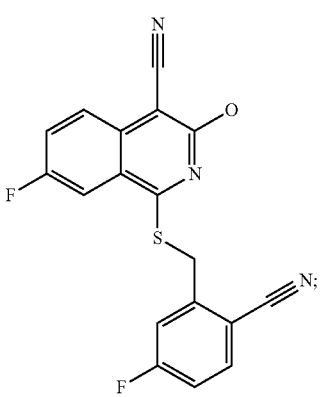
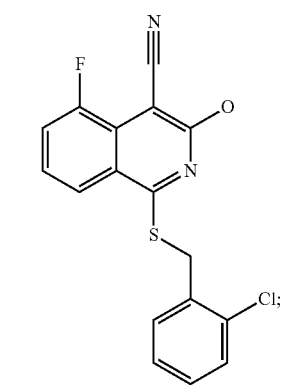
-continued
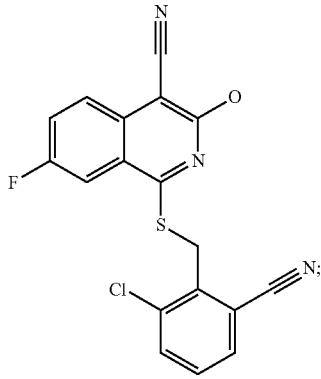
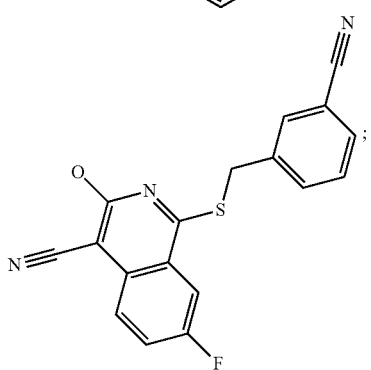
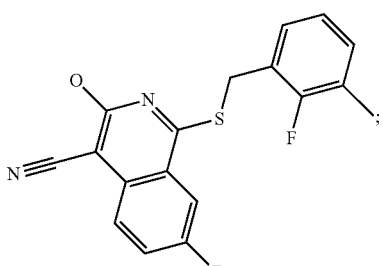
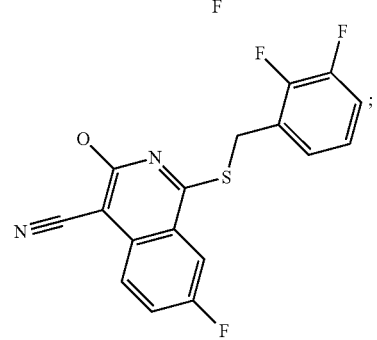
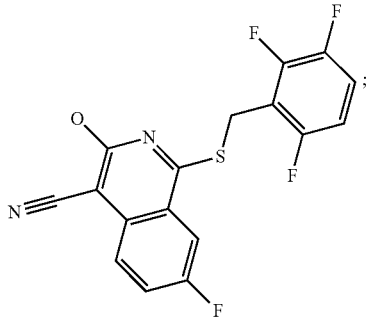

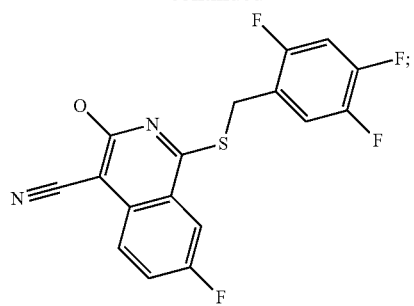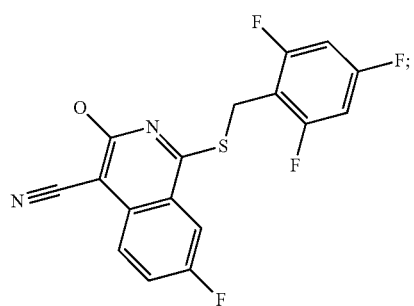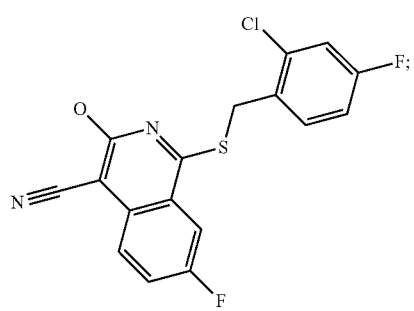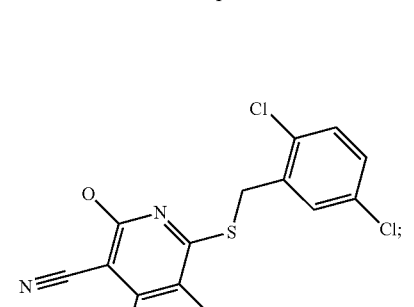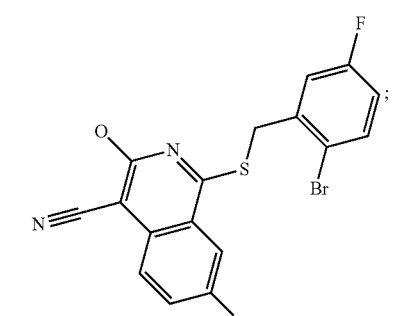
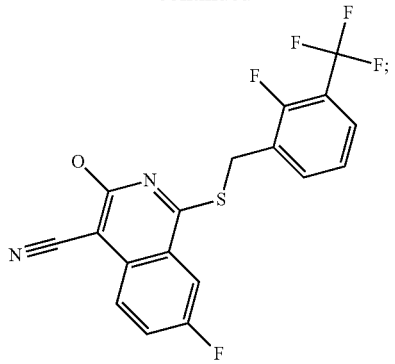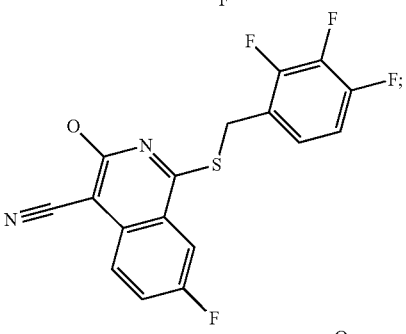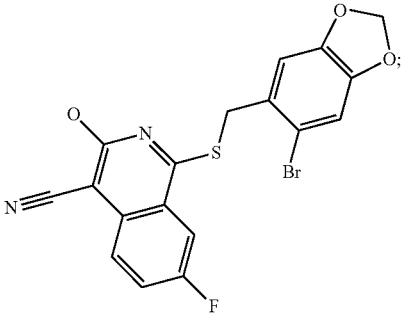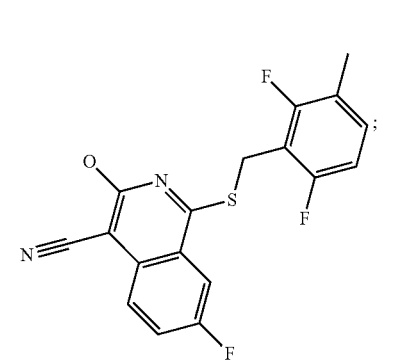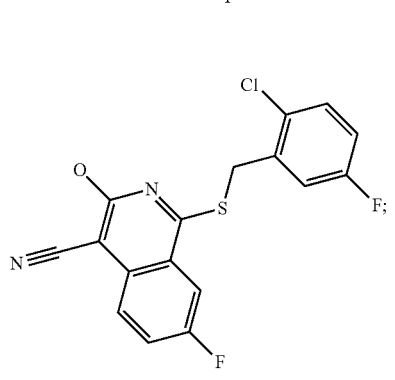

227
-continued
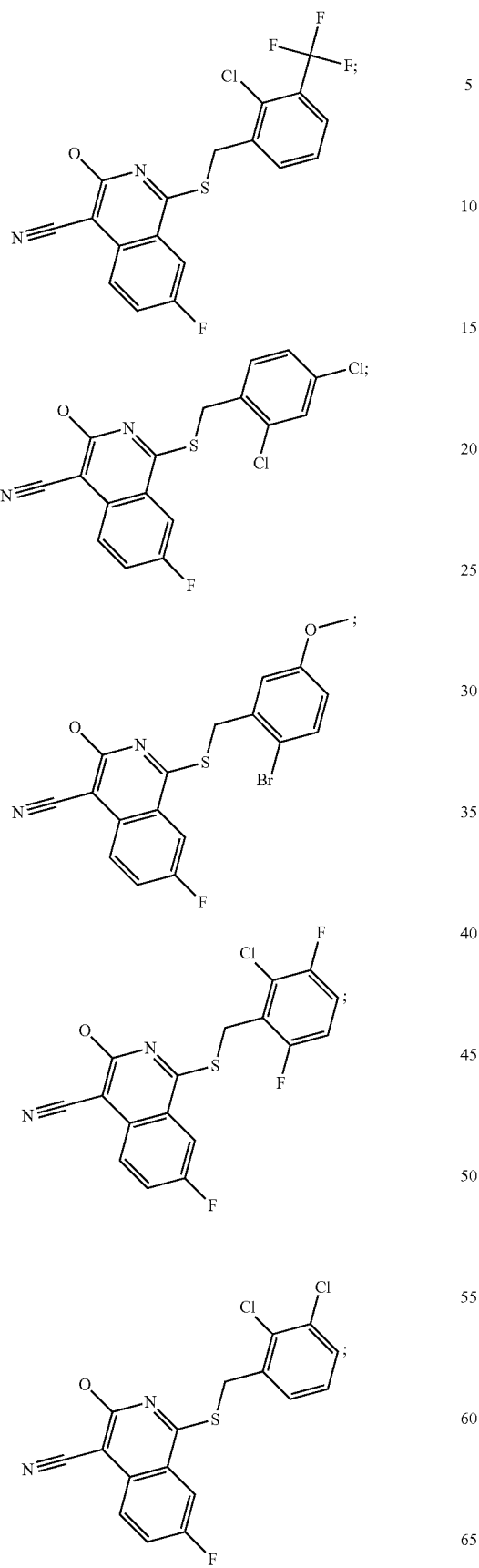
228
-continued
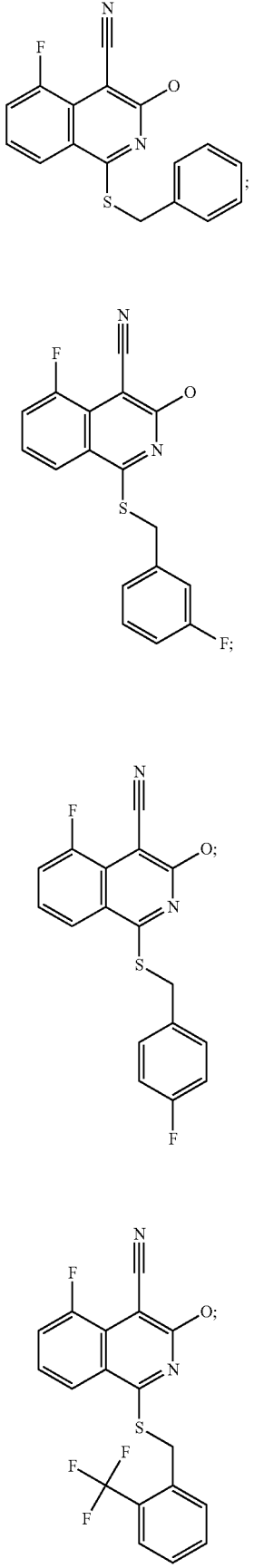

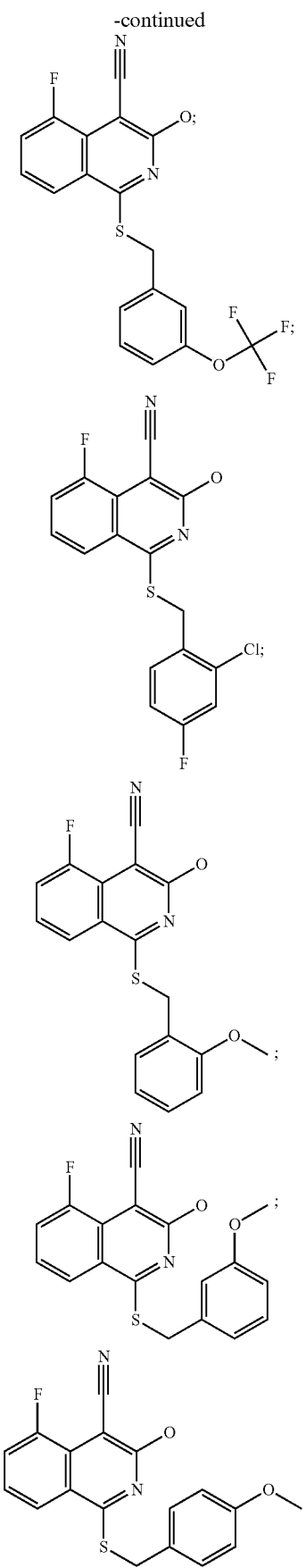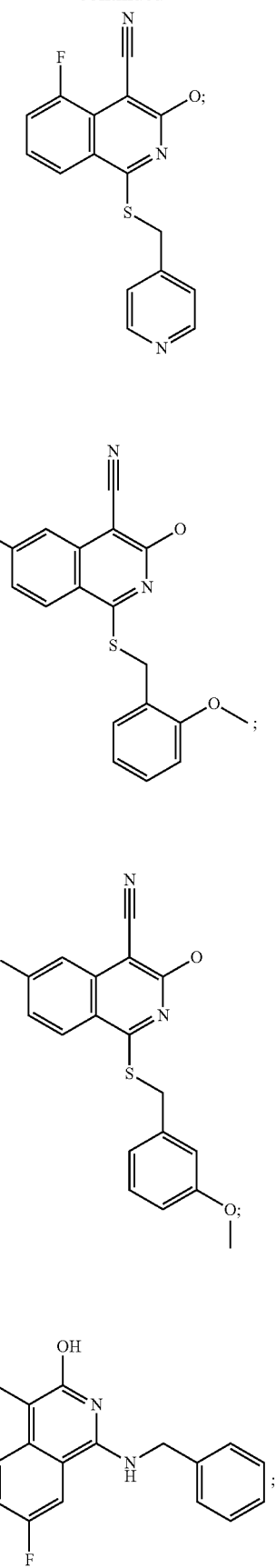

-continued

233
-continued
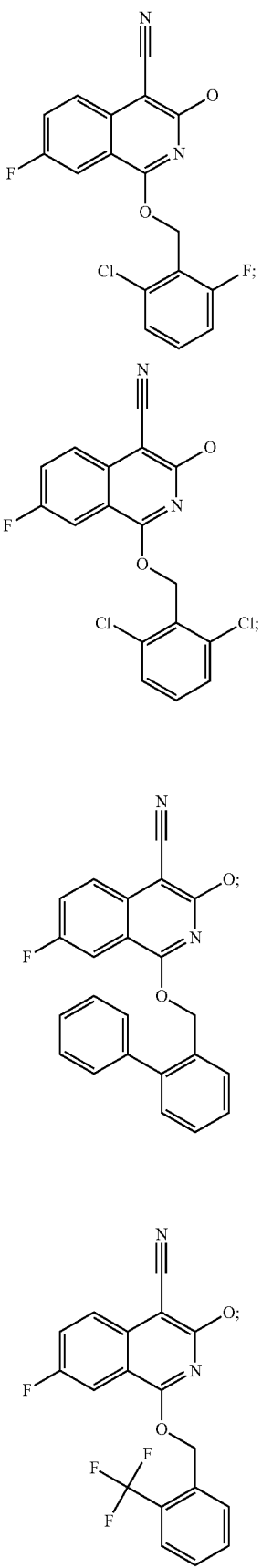
234
-continued
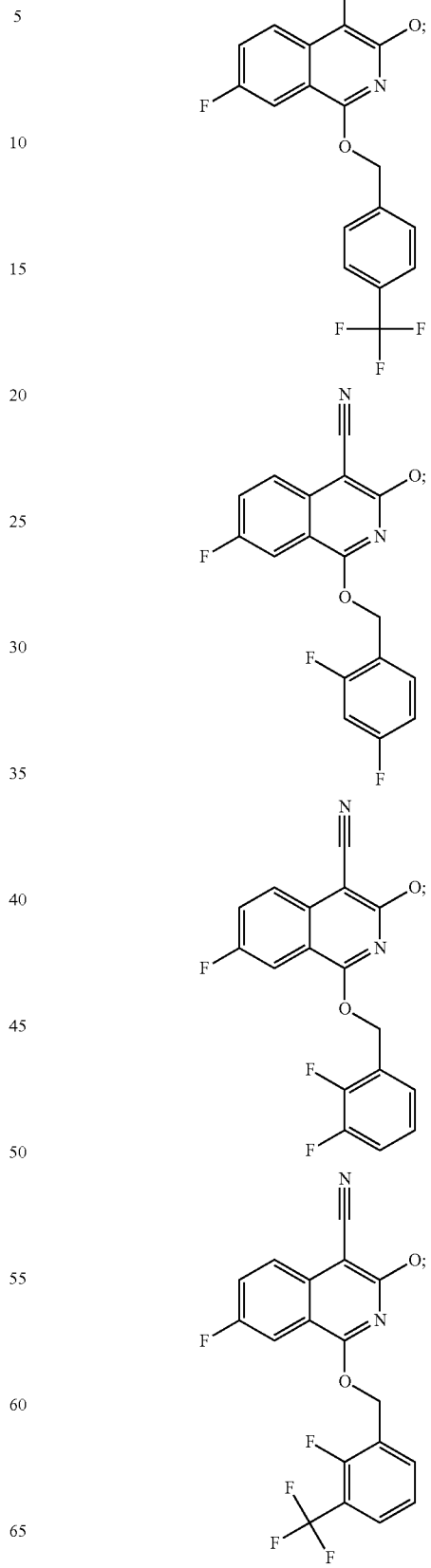

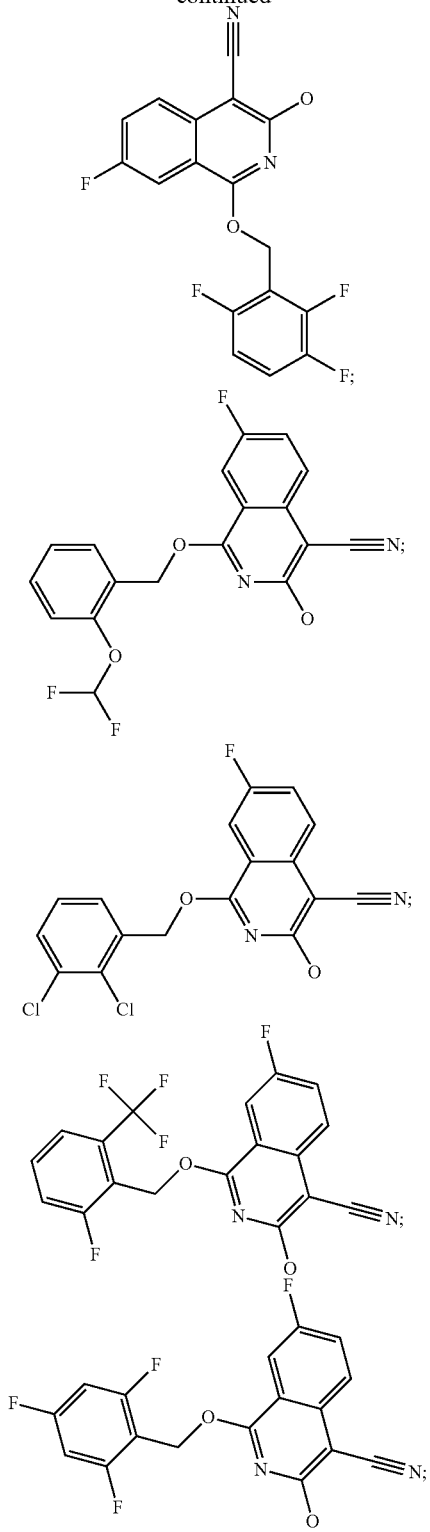
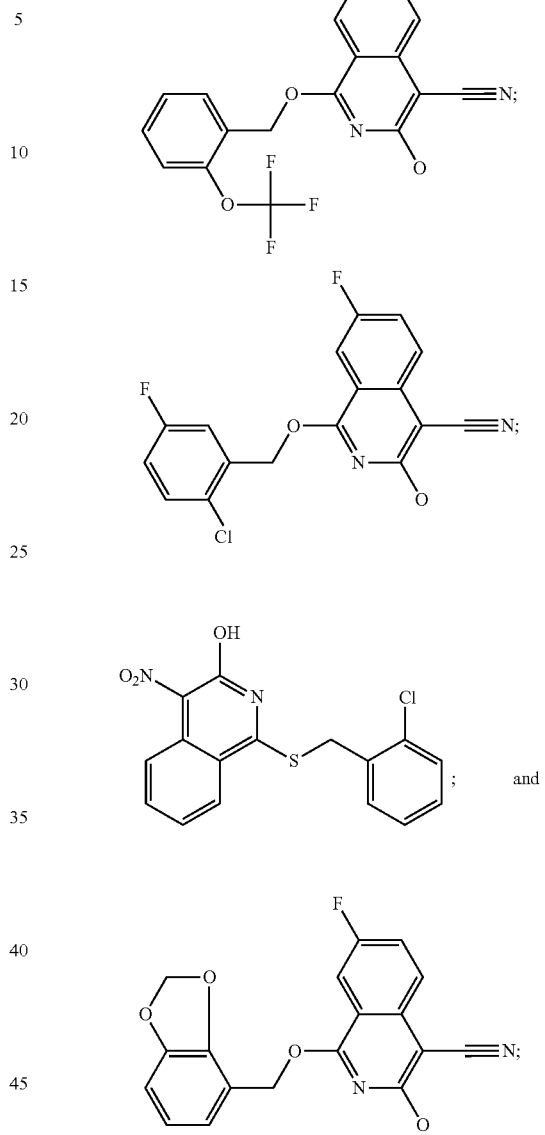
wherein the "—O" attached to the carbon adjacent to the nitrogen in the bicyclic core is used to denote an "—OH" group as indicated in Formula I.
4. A pharmaceutical composition comprising a compound of claim 1 and a pharmaceutically acceptable carrier.
5. A pharmaceutical composition comprising a compound of claim 3 and a pharmaceutically acceptable carrier.
* * * * *

UNITED STATES PATENT AND TRADEMARK OFFICE
CERTIFICATE OF CORRECTION

PATENT NO. : 8,318,941 B2
APPLICATION NO. : 12/307424
DATED : November 27, 2012
INVENTOR(S) : Jeffrey A. Robl et al.

It is certified that error appears in the above-identified patent and that said Letters Patent is hereby corrected as shown below:

On the Title Page:

Item (75), Inventors:

Change "Jeffrey A. Robl, Newton, PA (US)" to -- Jeffrey A. Robl, Newtown, PA (US) --.

Signed and Sealed this
First Day of April, 2014

Michelle K. Lee
*Deputy Director of the United States Patent and Trademark Office*